(12) United States Patent
Ahmad

(10) Patent No.: US 8,722,417 B2
(45) Date of Patent: May 13, 2014

(54) THERMOELECTRIC SENSOR FOR ANALYTES IN A FLUID AND RELATED METHOD

(75) Inventor: Lubna Ahmad, Chandler, AZ (US)

(73) Assignee: Invoy Technologies, L.L.C., Chandler, AZ (US)

( * ) Notice: Subject to any disclaimer, the term of this patent is extended or adjusted under 35 U.S.C. 154(b) by 724 days.

(21) Appl. No.: 11/656,338

(22) Filed: Jan. 20, 2007

(65) Prior Publication Data

US 2008/0056946 A1    Mar. 6, 2008

Related U.S. Application Data

(63) Continuation-in-part of application No. 11/607,829, filed on Dec. 2, 2006, now abandoned, which is a continuation-in-part of application No. 11/593,144, filed on Nov. 2, 2006, now abandoned, which is a continuation-in-part of application No. 11/273,625, filed on Nov. 14, 2005, now Pat. No. 8,088,333, which is a continuation-in-part of application No. 10/554,801, filed as application No. PCT/US2004/013364 on Apr. 28, 2004, now abandoned.

(60) Provisional application No. 60/465,949, filed on Apr. 28, 2003.

(51) Int. Cl.

| | | |
|---|---|---|
| *G01N 33/53* | (2006.01) | |
| *G01N 33/497* | (2006.01) | |
| *G01N 21/35* | (2014.01) | |
| *G01N 33/68* | (2006.01) | |
| *G01N 15/02* | (2006.01) | |
| *G01N 1/22* | (2006.01) | |
| *G01N 21/03* | (2006.01) | |
| *G01N 21/84* | (2006.01) | |
| *G01N 31/22* | (2006.01) | |
| *G01N 21/78* | (2006.01) | |
| *G01D 1/06* | (2006.01) | |

(52) U.S. Cl.
CPC ........ *G01N 33/4972* (2013.01); *G01N 21/3504* (2013.01); *G01N 2800/347* (2013.01); *G01N 33/6893* (2013.01); *G01N 15/0205* (2013.01); *G01N 2001/2223* (2013.01); *G01N 2800/50* (2013.01); *G01N 21/0332* (2013.01); *G01N 21/8483* (2013.01); *G01N 31/22* (2013.01); *G01N 21/783* (2013.01); *G01N 31/224* (2013.01); *G01D 1/06* (2013.01)
USPC ........... 436/149; 436/147; 436/157; 436/164; 436/167; 422/83; 422/84; 422/85; 422/86; 422/87; 422/88; 422/89; 422/90; 422/91; 422/92; 422/98; 422/400; 422/401; 422/420; 422/421; 422/422; 422/423; 422/424; 422/425; 422/426; 422/427; 422/428; 422/429

(58) Field of Classification Search
USPC ......... 422/51, 68.1, 82.12, 84, 95, 83, 85, 86, 422/87, 88, 89, 90, 91, 92, 98, 400, 401, 422/420, 421, 422, 423, 424, 425, 426, 427, 422/428, 429; 436/147, 157, 164, 167, 900
See application file for complete search history.

(56) References Cited

U.S. PATENT DOCUMENTS

| | | |
|---|---|---|
| 1,997,659 A | 7/1929 | Styer |
| 3,552,207 A | 1/1971 | Monk et al. |
| 3,578,405 A | 5/1971 | Woodle |
| 3,904,371 A | 9/1975 | Neti et al. |
| 3,998,591 A | 12/1976 | Eckfeldt |
| 4,070,157 A | 1/1978 | Iles |
| 4,115,229 A | 9/1978 | Capone |
| 4,169,126 A | 9/1979 | Iles |
| 4,241,303 A | 12/1980 | Thompson |
| 4,323,536 A | 4/1982 | Columbus |
| 4,337,654 A | 7/1982 | Austin et al. |
| 4,339,318 A | 7/1982 | Tanaka |
| 4,358,957 A | 11/1982 | Lougheed et al. |
| 4,391,777 A | 7/1983 | Hutson |
| 4,414,839 A | 11/1983 | Dilley et al. |
| 4,430,192 A | 2/1984 | Maeda |
| 4,931,404 A | 6/1990 | Kundu |
| 4,935,345 A | 6/1990 | Guilbeau et al. |

| | | | |
|---|---|---|---|
| 4,962,025 A | 10/1990 | Moldowan | |
| 4,970,172 A | 11/1990 | Kundu | |
| 5,018,395 A | 5/1991 | Hickox | |
| 5,032,266 A * | 7/1991 | Kirkland et al. | 210/198.2 |
| 5,071,769 A | 12/1991 | Kundu | |
| 5,087,312 A | 2/1992 | Gerber | |
| 5,108,576 A | 4/1992 | Malmros | |
| 5,113,874 A | 5/1992 | Maronian | |
| 5,174,959 A | 12/1992 | Kundu | |
| 5,352,352 A | 10/1994 | Tsukada | |
| 5,356,217 A | 10/1994 | Sheffield | |
| 5,367,890 A | 11/1994 | Doke | |
| 5,505,073 A | 4/1996 | Gerblinger | |
| 5,571,395 A | 11/1996 | Park et al. | |
| 5,656,142 A | 8/1997 | Park | |
| 5,962,335 A | 10/1999 | Katzman | |
| 6,015,533 A | 1/2000 | Young | |
| 6,067,989 A | 5/2000 | Katzman | |
| 6,079,873 A | 6/2000 | Cavicchi et al. | |
| 6,186,958 B1 | 2/2001 | Katzman et al. | |
| 6,190,858 B1 | 2/2001 | Persaud et al. | |
| 6,221,026 B1 | 4/2001 | Phillips | |
| 6,234,006 B1 | 5/2001 | Sunshine | |
| 6,238,085 B1 | 5/2001 | Higashi et al. | |
| 6,289,286 B1 | 9/2001 | Andersson | |
| 6,417,424 B1 | 7/2002 | Bewick-Sonntag et al. | |
| 6,436,346 B1 | 8/2002 | Doktycz | |
| 6,491,643 B2 | 12/2002 | Katzman et al. | |
| 6,555,821 B1 | 4/2003 | Himberg et al. | |
| 6,572,543 B1 | 6/2003 | Christopherson et al. | |
| 6,582,376 B2 | 6/2003 | Baghdassarian | |
| 6,599,253 B1 | 7/2003 | Baum et al. | |
| 6,607,387 B2 | 8/2003 | Mault | |
| 6,609,068 B2 | 8/2003 | Cranley et al. | |
| 6,613,205 B1 | 9/2003 | Steiner | |
| 6,629,934 B2 | 10/2003 | Mault et al. | |
| 6,631,333 B1 | 10/2003 | Lewis et al. | |
| 6,658,915 B2 | 12/2003 | Sunshine et al. | |
| 6,709,405 B2 | 3/2004 | Jonson | |
| 6,787,776 B2 | 9/2004 | Webber et al. | |
| 6,790,178 B1 | 9/2004 | Mault et al. | |
| 6,846,654 B1 | 1/2005 | Blackburn | |
| 7,022,288 B1 | 4/2006 | Boss | |
| 7,141,210 B2 | 11/2006 | Bell | |
| 7,220,387 B2 | 5/2007 | Flaherty | |
| 7,329,389 B2 | 2/2008 | Horovitz | |
| 7,338,637 B2 | 3/2008 | Pease | |
| 7,364,551 B2 | 4/2008 | Allen | |
| 7,374,719 B2 | 5/2008 | Anaokar | |
| 7,763,208 B2 | 7/2010 | Steichen et al. | |
| 2003/0056570 A1 | 3/2003 | Shin | |
| 2003/0186453 A1 | 10/2003 | Bell | |
| 2004/0018114 A1 | 1/2004 | Wang | |
| 2004/0236244 A1 | 11/2004 | Allen et al. | |
| 2005/0076943 A1 | 4/2005 | Cooper et al. | |
| 2005/0084921 A1 | 4/2005 | Cranley et al. | |

FOREIGN PATENT DOCUMENTS

| | | | |
|---|---|---|---|
| WO | WO 03008942 A1 * | 1/2003 | |
| WO | 03/039367 A1 | 5/2003 | |
| WO | 03/039483 A2 | 5/2003 | |

OTHER PUBLICATIONS

U.S. Appl. No. 11/781,784, published Jan. 3, 2008, Allen. Auguet, C., Seguin, J. L., Martorell, F., Moll, F., Torra, V., & Lerchner, J. (2006). Identification of micro-scale calorimetric devices. Journal of Thermal Analysis and Calorimetry, 86(2), 521-529.

Baier, V., Fodisch, R., Ihring, A., Kessler, E., Lerchner, J., Wolf, G., et al. (2005). Highly sensitive thermopile heat power sensor for micro-fluid calorimetry of biochemical processes. Sensors and Actuators a-Physical, 123-24, 354-359.

Balko, B., Berger, R. L., & Friauf, W. (1969). Stopped-Flow Calorimetry for Biochemical Reactions. Analytical Chemistry, 41(11), 1506-&.

Bataillard, P., Steffgen, E., Haemmerli, S., Manz, A., & Widmer, H. M. (1993). An Integrated Silicon Thermopile as Biosensor for the Thermal Monitoring of Glucose, Urea and Penicillin. Biosensors & Bioelectronics, 8(2), 89-98.

Bayraktar, T., & Pidugu, S. B. (2006). Characterization of liquid flows in microfluidic systems. International Journal of Heat and Mass Transfer, 49(5-6), 815-824.

Bhagat, A. A. S., Peterson, E. T. K., & Papautsky, I. (2007). A passive planar micromixer with obstructions for mixing at low Reynolds numbers. Journal of Micromechanics and Microengineering, 17(5), 1017-1024.

Bishop, P. L., Gibbs, J. T., & Cunningham, B. E. (1997). Relationship between concentration and hydrodynamic boundary layers over biofilms. Environmental Technology, 18(4), 375-385.

Bruylants, G., Wouters, J., & Michaux, C. (2005). Differential scanning calorimetry in life science: Thermodynamics, stability, molecular recognition and application in drug design. Current Medicinal Chemistry, 12(17), 2011-2020.

Caspary, D., Schropfer, M., Lerchner, J., & Wolf, G. (1999). A high resolution IC-calorimeter for the determination of heats of absorption onto thin coatings. Thermochimica Acta, 337(1-2), 19-26.

Casquillas, G. V., Bertholle, F., Le Berre, M., Meance, S., Malaquin, L., Greffet, J. J., et al. (2008). Thermo-resistance based micro-calorimeter for continuous chemical enthalpy measurements. Microelectronic Engineering, 85(5-6), 1367-1369.

Chung, C. K., & Shih, T. R. (2008). Effect of geometry on fluid mixing of the rhombic micromixers. Microfluidics and Nanofluidics, 4(5), 419-425.

Esfandyarpour, H., Fabian, R., Pease, W., & Davis, R. W. (2008). Picocalorimetric method for DNA sequencing. Journal of Vacuum Science & Technology B, 26(2), 661-665.

Esfandyarpour, H., Zheng, B., Fabian, R., Pease, W., & Davis, R. W. (2008). Structural optimization for heat detection of DNA thermosequencing platform using finite element analysis. Biomicrofluidics, 2(2), 11.

Friedrich, D., Please, C., & Melvin, T. (2008). Optimisation of analyte transport in integrated microfluidic affinity sensors for the quantification of low levels of analyte. Sensors and Actuators B-Chemical, 131(1), 323-332.

Gervais, T., & Jensen, K. F. (2006). Mass transport and surface reactions in microfluidic systems. Chemical Engineering Science, 61(4), 1102-1121.

Gigras, A., & Pushpavanam, S. (2008). Early induction of secondary vortices for micromixing enhancement. Microfluidics and Nanofluidics, 5(1), 89-99.

Hagleitner, C., Lange, D., Hierlemann, A., Brand, O., & Baltes, H. (2002). CMOS single-chip gas detection system comprising capacitive, calorimetric and mass-sensitive microsensors. Ieee Journal of Solid-State Circuits, 37(12), 1867-1878.

Hu, G. Q., Gao, Y. L., & Li, D. Q. (2007). Modeling micropatterned antigen-ant body binding kinetics in a microfluidic chip. Biosensors & Bioelectronics, 22(7), 1403-1409.

Jiang, F., Drese, K. S., Hardt, S., Kupper, M., & Schonfeld, F. (2004). Helical flows and chaotic mixing in curved micro channels. Aiche Journal, 50(9), 2297-2305.

Johannessen, E. A., Weaver, J. M. R., Bourova, L., Svoboda, P., Cobbold, P. H., & Cooper, J. M. (2002). Micromachined nanocalorimetric sensor for ultra-low-volume cell-based assays. Analytical Chemistry, 74(9), 2190-2197.

Jones, F., Bailey, R., Wilson, S., & Hiestand, J. (2007). The effects of engineering design on heterogeneous biocatalysis in microchannels. Applied Biochemistry and Biotechnology, 137, 859-873.

Kjeang, E., Sinton, D., & Harrington, D. A. (2006). Strategic enzyme patterning for microfluidic biofuel cells. Journal of Power Sources, 158(1), 1-12.

Kurzawski, P., Hagleitner, C., & Hierlemann, A. (2006). Detection and discrimination capabilities of a multitransducer single-chip gas sensor system. Analytical Chemistry, 78(19), 6910-6920.

Kwak, B. S., Kim, B. S., Cho, H. H., Park, J. S., & Jung, H. I. (2008). Dual thermopile integrated microfluidic calorimeter for biochemical thermodynamics. Microfluidics and Nanofluidics, 5(2), 255-262.

Lee, J., Lim, K. G., Patmore, G. T. R., & Tripathi, A. (2007). Optimization of microfluidic fuel cells using transport principles. Analytical Chemistry, 79(19), 7301-7307.

Lerchner, J., Maskow, T., & Wolf, G. (2008). Chip calorimetry and its use for biochemical and cell biological investigations. Chemical Engineering and Processing, 47(6), 991-999.

Lerchner, J., Wolf, A., Buchholz, F., Mertens, F., Neu, T. R., Harms, H., et al. (2008). Miniaturized calorimetry—A new method for real-time biofilm activity analysis. Journal of Microbiological Methods, 74(2-3), 74-81.

Lerchner, J., Kirchner, R., et al. (2006). Determination of molar heats of absorption of enantiomers into thin chiral coatings by combined IC-calorimetric and microgravimetric (QMB) measurements II. Thermodynamics of enantio selectivity in modified cyclodextrins. Thermochimica Acta, 445(2), 98-103.

Lerchner, J., Wolf, A., Huttl, R., & Wolf, G. (2004). Direct monitoring of biochemical processes using micro-structured heat power detectors. Chemical Engineering Journal, 101(1-3), 187-194.

Lerchner, J., Wolf, A., Wolf, G., Baier, V., Kessler, E., Nietzsche, M., et al. (2006). A new micro-fluid chip calorimeter for biochemical applications. Thermochimica Acta, 445(2), 144-150.

Lerchner, J., Wolf, A., Wolf, G., & Fernandez, I. (2006). Chip calorimeters for the investigation of liquid phase reactions: Design rules. Thermochimica Acta, 446(1-2), 168-175.

Lerchner, J., Wolf, G., Torralba, A., & Torra, V. (1997). Ambient perturbation reduction in microsized calorimetric systems. Thermochimica Acta, 302(1-2), 201-210.

Lerchner, J., Seidel, J., Wolf, G., & Weber, E. (1996). Calorimetric detection of organic vapours using inclusion reactions with organic coating materials. Sensors and Actuators B-Chemical, 32(1), 71-75.

Li, Y., Vancura, C., Barrettino, D., Graf, M., Hagleitner, C., Kummer, A., et al. (2007). Monolithic CMOS multi-transducer gas sensor microsystem for organic and inorganic analytes. Sensors and Actuators B-Chemical, 126(2), 431-440.

Manglik, R. M., & Bergles, A. E. (2004). Enhanced heat and mass transfer in the new millennium: A review of the 2001 literature. Journal of Enhanced Heat Transfer, 11(2), 87-118.

Masud, M. M., Kuwahara, M., Ozaki, H., & Sawai, H. (2004). Sialyl-lactose-binding modified DNA aptamer bearing additional functionality by SELEX. Bioorganic & Medicinal Chemistry, 12(5), 1111-1120.

Minakov, A. A., & Schick, C. (2007). Ultrafast thermal processing and nanocalorimetry at heating and cooling rates up to 1 MK/s. Review of Scientific Instruments, 78(7).

Muehlbauer, M. J., Guilbeau, E. J., Towe, B. C., & Brandon, T. A. (1990). Thermoelectric Enzyme Sensor for Measuring Blood-Glucose. Biosensors & Bioelectronics, 5(1), 1-12.

Pennathur, S., Meinhart, C. D., & Soh, H. T. (2008). How to exploit the features of microfluidics technology. Lab on a Chip, 8(1), 20-22.

Perez-Herranz, V., Guinon, J. L., & Garcia-Anton, J. (2000). A new technique for the visualization of the concentration boundary layer in an electrodialysis cell. Journal of Applied Electrochemistry, 30(7), 809-816.

Rida, A., & Gijs, M. A. M. (2004). Manipulation of self-assembled structures of magnetic beads for microfluidic mixing and assaying. Analytical Chemistry, 76(21), 6239-6246.

Salemme, F. R. (2004). High-throughput biochemistry heats up. Nature Biotechnology, 22(9), 1100-1101.

Squires, T. M., Messinger, R. J., & Manalis, S. R. (2008). Making it stick: convection, reaction and diffusion in surface-based biosensors. Nature Biotechnology, 26(4), 417-426.

Torres, F. E., Kuhnt, P., De Bruyker, D., Bell, A. G., Wolkin, M. V., Peeters, E., et al. (2004). Enthalpy arrays. Proceedings of the National Academy of Sciences of the United States of America, 101(26), 9517-9522.

Towe, B. C., & Guilbeau, E. J. (1996). A v brating probe thermal biochemical sensor. Biosensors & Bioelectronics, 11(3), 247-252.

van Herwaarden, A. W. (2005). Overview of calorimeter chips for various applications. Thermochimica Acta, 432(2), 192-201.

Vandyke, M. (1994). 19TH-Century Roots of the Boundary-Layer Idea. Siam Review, 36(3), 415-424.

Verhaegen, K., Baert, K., Simaels, J., & Van Driessche, W. (2000). A high-throughput silicon microphysiometer. Sensors and Actuators a-Physical, 82(1-3), 186-190.

Wang, H. Z., Iovenitti, P., Harvey, E., & Masood, S. (2002). Optimizing layout of obstacles for enhanced mixing m microchannels. Smart Materials & Structures, 11(5), 662-667.

Weber, P. C., & Salemme, F. R. (2003). Applications of calorimetric methods to drug discovery and the study of protein interactions. Current Opinion in Structural Biology, 13(1), 115-121.

Xu, J., Reiserer, R., Tellinghuisen, J., W kswo, J. P., & Baudenbacher, F. J. (2008). A microfabricated nanocalorimeter: Design, characterization, and chemical calibration. Analytical Chemistry, 80(8), 2728-2733.

Yoon, S. I., Lim, M. H., Park, S. C., Shin, J. S., & Kim, Y. J. (2008). Neisseria meningitidis detection based on a microcalorimetric biosensor with a split-flow microchannel. Journal of Microelectromechanical Systems, 17(3), 590-598.

Yoon, S. K., Fichtl, G. W., & Kenis, P. J. A. (2006). Active control of the depletion boundary layers in microfluidic electrochemical reactors. Lab on a Chip, 6(12), 1516-1524.

Zhang, Y. Y., & Tadigadapa, S. (2004). Calorimetric biosensors with integrated microfluidic channels. Biosensors & Bioelectronics, 19(12), 1733-1743.

Zhou, R., Hierlemann, A., Weimar, U., & Gopel, W. (1996). Gravimetric, dielectric and calorimetric methods for the detection of organic solvent vapours using poly(ether urethane) coatings. Sensors and Actuators B-Chemical, 34(1-3), 356-360.

Ahmad L. "Towards Noninvasive Metabolic Monitoring: The Technical Feasibility of a Thermoelectric Acetone Sensor." Presentation on Dec. 2, 2005 at Arizona State University, USA.

Ahmad L, Guilbeau EJ. "Design of a Breath Ketone Sensor for Obesity Management." Poster Presentation, Fall Meeting of the Biomedical Engineering Society, Oct. 15, 2004, USA.

Ahmad L. "Soft Lithography as a Technique for Thermopile Development." Poster presentation at undergraduate bioengineering dept at Arizona State University on Apr. 26, 2002, USA.

Barnett D, Tassopoulos CN, Fraser TR. Breath Acetone and Blood Sugar Measurements in Diabetes. Clinical Science 1969; 37 (2): 570.

Bunka DH, Stockley PG. Aptamers come of age—at last. Nature Reviews 2006; 4: 588-596.

Byrne HA, Tieszen KL, Hollis S, Dornan TL, New JP. Evaluation of an Electrochemical Sensor for Measuring Blood Ketones. Diabetes Care 2000. 23 (4): 500-503.

Dexter Research Center. Jul. 20, 2007. Dexter Research Corporation. Aug. 13, 2007 <http://www.dexterresearch.com>.

Dillner U, Kessler E, Poser S, et al. Thermal Simulation of a Micromachined Thermopile-Based Thin-Film Gas Flow Sensor. Microelectronics Journal 1998; 29 (4-5): 291-297.

Dotan N, Alstock RT, et al. Anti-glycan antibodies as biomarkers for diagnosis and prognosis. Lupus 2006; 15: 442-450.

Dube DH, Bertozzi CR. Glycans in cancer and inflammation: potential for therapeutics and diagnostics. Nature Reviews 2005; 4: 477.

Gabius HJ, Andre S, et al. The sugar code: functional lectinomics. Biochimica et Biophysica Acta 2002; 1572: 165.

Giovannetti G et al. Study for a portable IR sensor to detect the blood temperature during coronary bypass implantation. Review of Scientific Instruments 2005; 76: 0843021-5.

Girard N. "Student develops non-invasive diabetes breath test." Arizona State University's State Press Apr. 9, 2003.

Godts P, et al. Peltier Effect for Measurement of Fluid Thermal Property—Application for Designing New Thermal Sensors. Sensors and Materials 1996; 8 (5): 293-301.

Hashimoto S, Asao T, et al. a1-Acid Glycoprotein fucosylation as a marker of carcinoma progression and prognosis. Cancer 2004; 101(12): 2825-2836.

Hayden GF. Olfactory Diagnosis in Medicine. Postgraduate Medicine 1980; 67 (4): 110.

Jones AW. Breath Acetone Concentrations in Fasting Male-Volunteers—Further-Studies and Effect of Alcohol Administration. Journal of Analytical Toxicology 1998; 12 (2): 75-79.

Jones AW. Breath-Acetone Concentrations in Fasting Healthy-Men—Response of Infrared Breath-Alcohol Analyzers. Journal of Analytical Toxicology 1987; 11 (2): 67-69.

Khan A et al. Evaluation of a bedside blood ketone sensor: the effects of acidosis, hyperglycaemia and acetoacetate of sensor performance. Diabetic Medicine 2004; 21: 782-785.

Kirby R, Cho EJ, et al. Aptamer-based sensor arrays for the detection and quantification of proteins. Analytical Chemistry 2004; 76: 4066-4075.

Kratz E, et al. Alterations of branching and differential expression of sialic acid on alpha-1-acid glycoprotein in human seminal plasma. Clinica Chimica Acta 2003; 331: 87-95.

Kundu SK, Bruzek JA, Nair R, Judilla AM. Breath Acetone Analyzer—Diagnostic-Tool to Monitor Dietary-Fat Loss. Clinical Chemistry 1993; 39(1): 87-92.

Kundu SK, Judilla AM. Novel Solid-Phase Assay of Ketone-Bodies in Urine. Clinical Chemistry 1991; 37 (9): 1565-1569.

Kupari M, Lommi J, Ventila M, Karjalainen U. Breath Acetone in Congestive-Heart-Failure. American Journal of Cardiology 1995; 76 (14): 1076.

Larson J. "Getting fat feedback." Arizona Republic Jul. 8, 2004.

Lerchner J, Caspary D, Wolf G. Calorimetric Detection of Volatile Organic Compounds. Sensors and Actuators B-Chemical 2000; 70 (1-3): 57-66.

Likhodii SS, Musa K, Cunnane SC. Breath Acetone as a Measure of Systemic Ketosis Assessed in a Rat Model of the Ketogenic Diet. Clinical Chemistry 2002; 48 (1): 115-120.

Loken SC. Breath Acetone and Ketone Metabolism in Obese and Diabetic Mice. Diabetes 1976; 25: 374-374 Suppl. 1.

Mathonat C, et al. Measurements of Excess-Enthalpies at High-Temperature and Pressure Using a New-Type of Mixing Unit. Journal of Solution Chemistry 1994; 23 (11): 1161-1182.

Muehlbauer MJ, Guilbeau EJ, Towe BC. Applications and Stability of A Thermoelectric Enzyme Sensor. Sensors and Actuators B-Chemical 1990; 2 (3): 223-232.

Muehlbauer MJ, Guilbeau EJ, Towe BC. Model for A Thermoelectric Enzyme Glucose Sensor. Analytical Chemistry 1989; 61 (1): 77-83.

Muralt P. Ferroelectric thin films for micro-sensors and actuators: a review. Journal of Micromechanical Microengineering 2000; 10: 136-146.

Musa-Veloso K, et al. Breath Acetone is a Reliable Indicator of Ketosis in Adults Consuming Ketogenic Meals. American Journal of Clinical Nutrition 2002; 76 (1): 65-70.

Neiman J, et al. Combined Effect of a Small Dose of Ethanol and 36-Hr Fasting on Blood-Glucose Response . . . Alcohol and Alcoholism 1987; 22 (3): 265-270.

Nelson N, et al. Exhaled Isoprene and Acetone in Newborn Infants and in Children With Diabetes Mellitus. Pediatric Research 1998; 44 (3): 363-367.

Rooth G. Clinical Value of Ketone Body Determinations in Brittle Diabetes. Acta Medica Scandinavica 1972; 191 (6): 549.

Sayer N, et al. Structural characterization of a 2'F-RNA aptamer that binds a HIV-1 SU glycoprotein, gp120. Biochem and Biophys Research Communications 2002; 293: 924-931.

Schreiter M, Gabl R, et al. Functionalized Pyroelectric Sensors for Gas Detection. Sensors and Actuators B 2006; 19: 255.

Schwarz M, et al. Serum anti-Glc(a1,4)Glc(a) antibodies as a biomarker for relapsing-remitting multiple sclerosis. Journal of the Neurological Sciences 2006; 244: 59-68.

Shiyan SD, Bovin NV. Carbohydrate composition and immunomodulatory activity of different glycoforms of a1-acid glycoprotein. Glycoconjugate Journal 1997; 14: 631-638.

Tian J, et al. Probing the binding of scutellarin to human serum albumin by circular dichroism, fluorescence spectroscopy, FTIR . . . Biomacromolecules 2004; 5(5): 1956-1961.

Trotter MD, Sulway MJ, Trotter E. Rapid Determination of Acetone in Breath and Plasma. Clinica Chimica Acta 1971; 35 (1): 137.

Tuerk C, Gold L. Systematic Evolution of Ligands by Exponential Enrichment: RNA Ligands to Bacteriophage T4 DNA Polymerase. Science 1990; 249: 505-510.

Xensor Integration. Jul. 24, 2007. Xensor Integration BV. Aug. 13, 2007 <http://xensor.nl>.

Khan ASA, Talbot JA, et al. Bedside Ketone Sensor Retains Accuracy Despite Changes in pH and the Presence of Potential Interferents. Diabetes 2002; 51: 418 Suppl. 2.

Ahmad L, et al. "Renal Failure Detection System." Poster presentation in undergraduate course poster session at Arizona State University on Dec. 14, 2004, USA.

Ahmad L, et al. "Design and Development of a Noninvasive Ammonia Detection System." Poster in undergraduate course poster session at Arizona State University on Apr. 22, 2005, USA.

Massick, SM. Diode Laser-Based Ketosis Sensor. DOD SBIR Awards 2002.

Walsh, J. End of the Spectrum: A Breath of Fresh Air in Diabetes Detection. Spectroscopy 2004; 19: 50. Also, description from MSU Technology Transfer Office.

Bischoff R, et al. On-line detection of volatile compounds in human breath. 4th European Congres of Oto-Rhino-Laryngology, Head and Neck Surgery 2000; 1369-1375.

Andersen, M. Y.; Pedersen, N.H.; Brabrand, H.; Hallager, L.; Jorgensen, S.B. "Regulation of a Continuous Yeast Bioreactor Near the Critical Dilution Rate Using a Productostat". Journal of Biotechnology 54. 1997. 1-14.

Anderson, J.C.; Lamm, W.J.E.; Hlastala, M.P. "Measuring Airway Exchange of Endogenous Acetone Using a Single-exhalation Breathing Maneuver". J Appl Physiol, 100. 2006. 880-889.

Barker, M.; Hengst, M.; Schmid, J.; Buers, H.-J.; Mittermaier, B.; Klemp, D.; Koppmann, R. "Volatile Organic Compounds in the Exhaled Breath of Young Patients with Cystic Fibrosis". Eur Respir J, 27. 2006. 929-936.

Barzana, E.; Klibanov, A.M.; Karel, M. "A Colorimetric Method for the Enzymatic Analysis of Gases: the Determination of Ethanol and Formaldehyde Vapors Using Solid Alcohol Oxidase". Analytical Biochemistry, 182. 1989. 109-115.

Bjarnason, B.; Johansson, P.; Johansson, G. "A Novel Thermal Biosensor: Evaluation for Determination of Urea in Serum". Analytica Chimica Acta, 372. 1998. 341-348.

Burritt, M.F. "Current Analytical Approaches to Measuring Blood Analytes". Clinical Chemistry, 36. 1990. 1562-1566.

Cooper, A.; Johnson, C.M. "Introduction to Microcalorimetry and Biomolecular Energetics". Methods in Molecular Biology, 22.1994. 109-124.

Crofford, O.B.; Mallard, R.E.; Winton, R.E.; Rogers, N.L.; Jackson, J.C.; Keller, U. "Acetone in Breath and Blood". Trans Am Clin Climatol Assoc, 88. 1977. 128-139.

Dubowski, K.M.; Essary, N.A. "Response of Breath-alcohol Analyzers to Acetone". Journal of Analytical Toxicology, 7. 1983. 231-234.

Dubowski, K.M.; Essary, N.A. "Response to Breath-alcohol Analyzers to Acetone: Further Studies". Journal of Analytical Toxicology, 8. 1984. 205-208.

Eklund, S.E.; Snider, R.M.; Wikswo, J.; Baudenbacher, F.; Prokop, A.; Cliffel, D.E. "Multianalyte Microphysiometry as a Tool in Metabolomics and Systems Biology". Journal of Electroanalytical Chemistry, 587. 2006. 333-339.

Fenske, J.D.; Paulson, S.E. "Human Breath Emissions of VOCs". Journal of Air & Waste Management Association, 49. 1999. 594-598.

Gage, J.C.; Lagesson, V.; Tunek, A. "A Method for the Determination of Low Concentrations of Organic Vapours in Air and Exhaled Breath". Annals of Occupational Hygiene, 20. 1977. 127-134.

Guilbeau, E.J.; Clark, L.C.; Pizziconi, V.B.; Schultz, J.S.; Towe, B.C. "Biosensors in Artificial Organs". ASAIO Trans, 33. 1987. 834-837.

Guilbeau, E.J.; Mayall, B.I. "Microthermocouple for Soft Tissue Temperature Determination". IEEE Transactions on Biomedical Engineering, 28. 1981. 301-305.

Guilbeau, E.J.; Towe, B.C.; Muehlbauer, M.J. "A Potentially Implantable Thermoelectric Sensor for Measurement of Glucose". ASAIO Trans, 33. 1987. 329-335.

Harper, M. "The Use of Thermal Desorption in Monitoring for the Chemical Weapons Demilitarization Program". J Environ Monit, 4. 2002. 688-694.

Harper, D.E.; Waldrop, R.D. "Infant Diabetic Ketoacidosis in the Emergency Department". Southern Medical Journal, 89. 1996. 729-731.

Hart, R.M.; Jones, J.D. "A New Micro Reaction Calorimeter". Journal of Thermal Analysis, 49. 1997. 1115-1119.

Hillaire, A.; Favre, E. "Isothermal and Nonisothermal Permeation of an Organic Vapor through a Dense Polymer Membrane". Ind. Eng. Chem. Res, 38. 1999. 211-217.

Huttl, R.; Bohmhammel, K; Pritzkat, K.; Wolf, G. "Problems Associated with Using Thermal Measurement Principles in Enzymatic Reactions". Thermochimica Acta, 229. 1993. 205-213.

Jensen, K.F. "Microreaction Engineering—Is Small Better?" Chemical Engineering Science, 56. 2001. 293-303.

Kohler, J.M.; Kessler, E.; Steinhage, G.; Grundig, B.; Cammann, K. "Thermoelectrical Micro-calorimetry and Microanalysis on Freestanding Membranes". Mikrochimica Acta, 120. 1995. 309-319.

Kohler, J.M.; Steinhage, G.; Krause, J.; Cammann, K. "Microanalytical Estimation of Cerium by a Miniaturized Thermoelectrical Sensor". Sensors and Actuators B. 23. 1995. 83-91.

Kohler, J.M.; Zieren, M. "Chip Reactor for Microfluid Calorimetry". Thermochimica Acta, 310. 1998. 25-35.

Kohler, J.M.; Zieren, M. "Micro Flow Calorimeter for Thermoelectrical Detection of Heat of Reaction in Small Volumes". Fresenius Journal of Analytical Chemistry, 358. 1997. 683-686.

Lerchner, J.; Wolf, A.; Wolf, G. "Recent Developments in Integrated Circuit Calorimetry". Journal of Thermal Analysis and Calorimetry, 57. 1999. 241-251.

Lestina, D.C.; Lund, A.K. "Laboratory Evaluation of Two Passive Alcohol Sensors". Journal of Studies on Alcohol, 53. 1992. 328-334.

Lucklum, R.; Henning, B.; Hauptmann, P. "Quartz Microbalance Sensors for Gas Detection". Sensors and Actuators A, 25-27. 1991. 705-710.

Makisimovich, N.; Vorotyntsev, V.; Nikitina, N.; Kaskevich, O.; Karabun, P.; Martynenko, F. "Adsorption Semiconductor Sensor for Diabetic Ketoacidosis Diagnosis". Sensors and Actuators B, 35-36. 1996. 419-421.

Mathis, T.R. "Development of a Thin Film Thermoelectric-immobilized Enzyme Glucose Sensor". Master of Science, Arizona State University. 1985. Abstract Only.

Matsumoto, K.; Matsubara, H.; Hamada, M.; Ukeda, H.; Osajima, Y. "Simultaneous Determination of Glucose, Ethanol and Lactate in Alcoholic Beverages and Serum by Amperometric Flow Injection Analysis with Immobilized Enzyme Reactors". Journal of Biotechnology, 14. 1990. 115-126.

McCall, J.K. "A Thin Film Thermal Enzyme Electrode for Detection of Glucose". Master of Science, Arizona State University. 1986. Abstract Only.

McGlashan, M.L.; Stoeckli, H.F. "A Flow Calorimeter for Enthalpies of Mixing the Enthalpy of Mixing of n-Hexane+Cyclohexane at 298.15 K". The Journal of Chemical Thermodynamics, 1. 1969. 589-594.

Miekisch, W.; Schubert, J.K.; Noeldge-Schomburg, G.F.E. "Diagnostic Potential of Breath Analysis—Focus on Volatile Organic Compounds" Clinica Chimica Acta, 347. 2004. 25-39.

Monk, P.; Wadso, I. "A Flow Micro Reaction Calorimeter". Acta Chemica Scandinavica, 22. 1968. 1842-1852.

Paulsson, N.J.P.; Winquist, F. "Analysis of Breath Alcohol with a Multisensor Array: Instrumental Setup, Characterization and Evaluation". Forensic Science International, 105. 1999. 95-114.

Pizziconi, V.B.; Page, D.L. "A Cell-based Immunobiosensor with Engineered Molecular Recognition—Part I: Design Feasibility". Biosensors & Bioelectronics, 12. 1997. 287-299.

Reichel, J.; Seyffarth, T.; Guth, U.; Mobius, H.H.; Gockeritz, D. "[Detection and Determination of Acetone Using Semiconductor Sensors]". Pharmazie, 44. 1989. 698-701. English Translation will be provided when available.

Rhemrev-Boom, M.M.; Korf, J.; Venema, K.; Urban, G.; Vadgama, P. "A Versatile Biosensor Device for Continuous Biomedical Monitoring" Biosensors & Bioelectronics, 16. 2001. 839-847.

Schierbaum, K.D.; Weimar, U.; Gopel, W. "Multicomponent Gas Analysis: An Analytical Chemistry Approach Applied to Modified SnO2 Sensors". Sensors & Actuators B, 2. 1990. 71-78.

Schilz, J. "Thermoelectric Infrared Senors (Thermopiles) for Remote Temperature Measurements; Pyrometry" Thermophysica Minima. 2000. 1-12.

Schmidt, W.; Schieferdecker, J. "Understanding Thermopile Infrared Sensors". Perkin Elmer. 2003. 5 pgs.

Shah, M.R.; Noble, R.D.; Clough, D.E. "Measurement of Sorption and Diffusion in Nonporous Membranes by Transient Permeation Experiments". Journal of Membrane Science, 287. 2007. 111-118.

Towe, B.C. "Vibration of Polarographic Oxygen Electrodes by Piezoelectric Elements: a Method of Reducing Flow Artifacts". IEEE Transactions on Biomedical Engineering, 34. 1987. 657-663.

Towe, B.C.; Pizziconi, V.B. "A Microflow Amperometric Glucose Biosensor". Biosensors & Bioelectronics, 12. 1997. 893-899.

Urban, G.; Kamper, H.; Jachimowicz, A.; Kohl, F.; Kuttner, H.; Olcaytug, F.; Goiser, P.; Pittner, F.; Schalkhammer, T.; Mann-Buxbaum, E. "The Construction of Microcalorimetric Biosensors by Use of High Resolution Thin-film Thermistors". Biosensors & Bioelectronics, 6. 1991. 275-280.

Van Herwaarden, A.W.; Sarro, P.M.; Gardner, J.W.; Bataillard, P. "Liquid and Gas Micro-calorimeters for Bio(Chemical) Measurements". Sensors and Actuators A, 43. 1994. 24-30.

Wang, L.; Lin, Q. "Theory and Experiments of MEMS Thermal Biosensors". IEEE Engineering in Medicine and Biology 27th Annual Conference. 2005. Shanghai, China. 1301-1304.

Wolf, A.; Weber, A.; Huttl, R.; Lerchner, J.; Wolf, G. "Sequential Flow Injection Analysis Based on Calorimetric Detection". Thermochimica Acta, 337. 27-38, (1999).

Xie, B.; Mecklenburg, M.; Danielsson, B.; Orman, O.; Norlin, P.; Winquist, F. "Development of an Integrated Thermal Biosensor for the Simultaneous Determination of Multiple Analytes". Analyst, 120. 1995. 155-160.

Xie, B.; Mecklenburg, M.; Danielsson, B.; Ohman, O.; Winquist, F. "Microbiosensor Based on an Integrated Thermopile". Analytica Chimica Acta, 299. 1994. 165-170.

Xie, B.; Ramanathan, K.; Danielsson, B. "Mini / Micro Thermal Biosensors and Other Related Devices for Biochemical / Clinical Analysis and Monitoring". Trends in Analytical Chemistry, 19. 2000. 340-349.

Xie, B.; Tang, X.; Wollenberger, U.; Johansson, G.; Gorton, L.; Scheller, F.; Danielsson, B. "Hybrid Biosensor for Simultaneous Electrochemical and Thermometric Direction". Analytical Letters, 30. 1997. 2141-2158.

Yotter, R.A.; Lee, L.A.; Wilson, D.M. "Sensor Technologies for Monitoring Metabolic Activity in Single Cells—Part I: Optical Methods". IEEE Sensors, 4. 2004. 395-411.

Zhang, Y.; Tadigadapa, S. "Microthermopiles Integrated with Fluidic Channels as Calorimetric MEMS Biosensors". Transducers '03, The 12th International Conference on Solid State Sensors, Actuators and Microsystems. 2003. Boston, MA. 1176-1179.

Zieren, M.; Kohler, J.M. "A Micro-fluid Channel Calorimeter Using BiSB/Sb Thin Film Thermopiles". Transducers '97, 1997 International Conference on Solid-State Sensors and Actuators. 1997. Chicago, IL. 539-542.

Reisman, D.J. "Acetone". Environmental Health Criteria 207. Geneva: World Health Organization. 1998.

Lawrence, David J. et al. "Thermopile Sensors for the Detection of Airborne Pollutants", IEEE Sensors 2007 Conference, pp. 1237-1240.

U.S. Appl. No. 10/205,710, issued Jan. 29, 2004, Wang.
U.S. Appl. No. 11/437,275, issued Mar. 1, 2007, Gabriel.
U.S. Appl. No. 11/737,631, issued Nov. 15, 2007, Flaherty.

Haug, M. et al., "Chemical Sensors Based Upon Polysiloxanes: comparison between optical, quartz microbalance, calorimetric, and capacitance sensors", Sensors and Actuators B, 11 (1993), pp. 383-391.

Schierbaum, K.D. et al., "Selective Detection of Organic Molecules With Polymers and Supramolecular Compounds: application of capacitance, quartz microbalance and calorimetric transducers", Sensors and Actuators A, 31 (1992), pp. 130-137.

Bell C.M. "Attaining Specificity in the Measurement of Ethanol in Breath" (1990) Acta Med Leg Soc (Liege), 40, 107-111, Australia (Abstract Only).

Bengt Danielsson, "Calorimetric Biosensors", Journal of Biotechnology, 1990, pp. 187-200, vol. 15, Elsevier, Sweden.

Jennifer K. McCall "A Thin Film Thermal Enzyme Electrode for Detection of Glucose" (1986) Master of Science, Arizona State University.

Michael Joseph Muehlbauer "The Design and Characterization of an Implantable Thermoelectric Enzyme Glucose Sensor" (1988) Ph.D. Dissertation, Arizona State University, Tempe.

Michael Joseph Muehlbauer "The Design Fabrication and Characterization of a Thin Film Thermopile" (1985) Master of Science, Arizona State University, Tempe.

Timothy Robert Mathis "Development of a Thin Film Thermoelectric-immobilized Enzyme Glucose Sensor" (1985) Master of Science, Arizona State University.

Kumaran Ramanathan et al.,"Principles and Applications of Thermal Biosensors". Biosensors & Bioelectronics, 2001, pp. 417-423, vol. 16, Elsevier, Sweden.

* cited by examiner

*Primary Examiner* — Dennis M White
(74) *Attorney, Agent, or Firm* — Meunier Carlin & Curfman, LLC

(57) ABSTRACT

An apparatus is provided for sensing an analyte in a fluid. The apparatus includes a fluid collecting device configured to collect the fluid containing the analyte; a fluid input in fluid communication with the fluid collecting device configured to input the fluid containing the analyte into the fluid collecting device, an analyte interactant in fluid communication with the fluid collecting device, wherein the analyte interactant, when contacted by the analyte, reacts to cause a first change in thermal energy within the fluid collecting device; a modulator that causes a second change in thermal energy; a thermal sensing device comprising at least one pyroelectric device thermally coupled to the fluid collecting device to generate a first signal in response to at least one of the first change in thermal energy and the second change in thermal energy; a control device operatively coupled to the thermal sensing device and the modulator that generates a second signal, wherein the second signal comprises information useful in characterizing the analyte. A related method also is disclosed.

44 Claims, 30 Drawing Sheets

Stage #1

Stage #2

Stage #1

Stage #2

| Sensor with dual binding sites for enhanced specificity | Sensor with single binding site | Utility of the secondary binding site for enhanced discrimination |

US 8,722,417 B2

THERMOELECTRIC SENSOR FOR ANALYTES IN A FLUID AND RELATED METHOD

RELATED APPLICATIONS

This is a continuation-in-part of U.S. application Ser. No. 11/607,829, filed on Dec. 2, 2006, which is a continuation-in-part of U.S. application Ser. No. 11/593,144, filed on Nov. 2, 2006, which is a continuation-in-part of U.S. application Ser. No. 11/273,625, filed on Nov. 14, 2005, which is a continuation-in-part of U.S. application Ser. No. 10/554,801, filed on Oct. 28, 2005, directed to a Thermoelectric Sensor for Analytes in a Gas, which claims priority based on PCT/US2004/013364, filed on Apr. 28, 2004, which claims priority to Application No. 60/465,949, filed on Apr. 28, 2003, the contents of each of which are hereby incorporated by reference in their entirety.

BACKGROUND

1. Field

The invention relates generally to apparatus and methods for sensing analytes in a fluid, such as a liquid or a gas. A preferred example involves the sensing of one or more analytes in air or a gas expired by an individual for monitoring biochemical processes such as in diabetes, epilepsy, weight loss, and others occurring within that individual.

2. Background

There are many instances in which it is desirable to sense the presence and/or quantity of an analyte in a gas. "Analyte" as the term is used herein is used broadly to mean the chemical component or constituent that is sought to be sensed using devices and methods according to various aspects of the invention. An analyte may be or comprise an element, compound or other molecule, an ion or molecular fragment, or other substance that may be contained within a fluid. In some instances, embodiments and methods, there may be more than one analyte. "Fluid" as the term is used herein is used broadly to comprise a substance that is capable of flowing and that changes its shape when acted upon by a force. It includes liquids and gases, not only in their pure forms but also when in heterogeneous states, such as with slurries, suspensions, colloidal dispersions, and the like. Newtonian fluids are best suited to application in the present invention, but some degree of non-Newtonian behavior could be acceptable, depending on the specific application, and this is not intended to be limiting. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. "Sense" and "sensing" as the terms are used herein are used broadly to mean detecting the presence of one or more analytes, or to measure the amount or concentration of the one or more analytes.

In many of these instances, there is a need or it is desirable to make the analysis for an analyte in the field, or otherwise to make such assessment without a requirement for expensive and cumbersome support equipment such as would be available in a hospital, laboratory or test facility. It is often desirable to do so in some cases with a largely self-contained device, preferably portable, and often preferably easy to use. It also is necessary or desirable in some instances to have the capability to sense the analyte in the fluid stream in real time or near real time. In addition, and as a general matter, it is highly desirable to accomplish such sensing accurately and reliably.

An example of the need for such devices is in the area of breath analysis. In the medical community, for example, there is a need for effective breath analysis to sense such analytes as acetone, isoprene, ammonia, alkanes, alcohol, and others, preferably using a hand-held or portable device that is relatively self contained, reliable and easy to use.

Historically, breath chemistry has not been very well exploited. Instead, blood and urine analysis has been performed. Blood analysis is painful, laborious, relatively expensive and often impractical due to lack of equipment or trained personnel. Typically blood analysis has been performed in a wet chemistry or hospital laboratory. Recently, there are two products that measure β-HBA levels that are made by GDS Diagnostics and Abbott Laboratories. While these companies have made home-testing possible, blood tests are still expensive and painful and they require careful disposal and procurement of needed equipment such as needles and collection vessels. This leads to low patient compliance.

Urine analysis has been criticized as being inaccurate. Urine analysis also is not time-sensitive in that the urine is collected in the bladder over a period of time.

Thus, while blood and urine tests can provide information about the physiological state of an individual, they have been relatively unattractive or ineffective for practical application where portability or field or home use is required.

Current systems used to sense an analyte in a gas, such as gas chromatographs and spectroscopy-related devices, are expensive, cumbersome to use, they require skilled operators or technicians, and otherwise typically are not practical for field or home use. They also tend to be quite expensive. Precision in detection systems usually comes at substantial cost. Current highly-accurate detection systems require expensive components such as a crystal, specialized power source, or containment chambers that are highly pH or humidity regulated.

Some systems for measuring analytes in air operate on electrochemical principles (see, e.g., U.S. Pat. No. 5,571,395, issued Nov. 5, 1996, to Park et al.), and some operate by infrared detection (see, e.g., U.S. Pat. No. 4,391,777 issued Jul. 5, 1983, to Hutson). U.S. Pat. No. 6,658,915, issued Dec. 9, 2003, to Sunshine et al., describes using chemically sensitive resistors to detect airborne substances and requires the use of an electrical source. U.S. Pat. No. 4,935,345, issued Jun. 19, 1990 to Guilbeau et al., describes the use of a single thermopile in liquid phase chemical analysis. However, the thermopile sensor is limited to measuring a single analyte and only a single reactant is present on the thermopile. This sensor operates in the liquid phase. Each of the foregoing patents is hereby incorporated herein by reference as if fully set forth herein.

SUMMARY OF THE INVENTION

The invention comprises systems, apparatus and methods for sensing at least one analyte in a fluid stream. According to one aspect of the invention, an apparatus is provided for sensing an analyte in a fluid. Apparatus according to this aspect comprise a fluid collecting device configured to collect the fluid containing the analyte; a fluid input in fluid communication with the fluid collecting device configured to input the fluid containing the analyte into the fluid collecting device, an analyte interactant in fluid communication with the fluid collecting device, wherein the analyte interactant, when contacted by the analyte, reacts to cause a first change in thermal energy within the fluid collecting device; a modulator that causes a second change in thermal energy; a thermal sensing device comprising at least one pyroelectric device thermally coupled to the fluid collecting device to generate a first signal in response to at least one of the first change in thermal energy and the second change in thermal energy; and a control device operatively coupled to the thermal sensing device and the modulator that generates a second signal, wherein the second signal comprises information useful in characterizing the analyte. In an optional embodiment, the apparatus comprises a second analyte interactant that, when contacted by the analyte, undergoes a second reaction to cause a third change in thermal energy.

In accordance with another aspect of the invention, a method is provided for sensing an analyte in a fluid. The method according to this aspect comprises providing a thermoelectric sensor comprising a thermal sensor comprising a pyroelectric device for measuring temperature, a modulator that causes a change in thermal energy, and an analyte interactant; causing the fluid and the analyte within the fluid to contact the analyte interactant so that the analyte interactant reacts with the analyte to cause a change in the temperature; and measuring the temperature change using the pyroelectric device and the modulator.

BRIEF DESCRIPTION OF THE DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings.

DETAILED DESCRIPTION OF THE PREFERRED EMBODIMENTS AND METHODS

Figure 1:
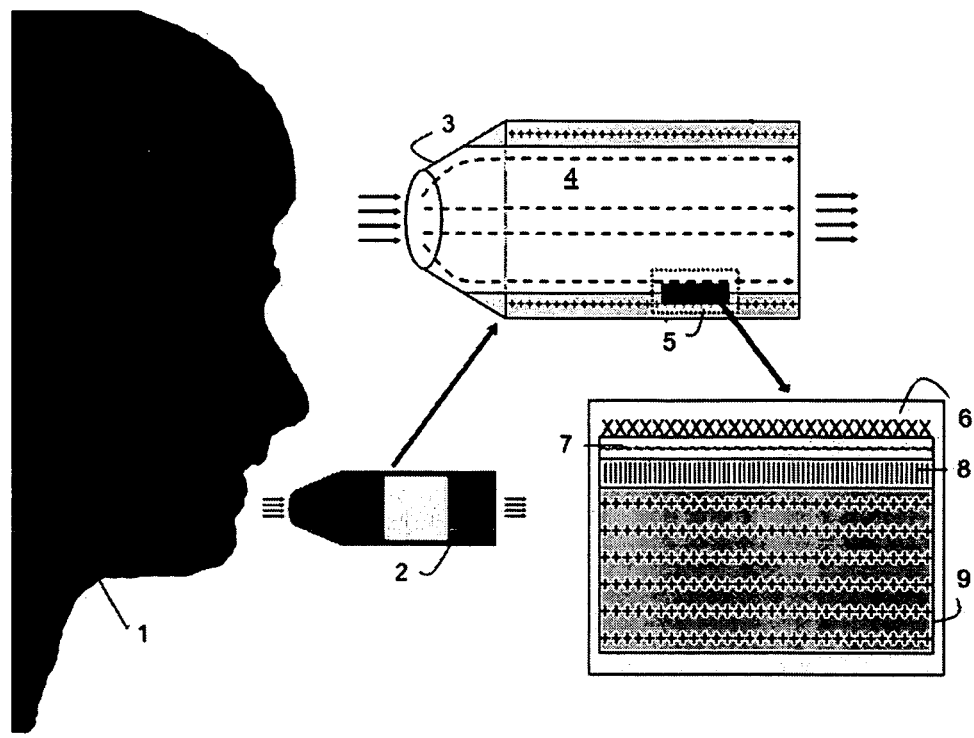
FIG. 1 shows is a composite illustration of sensor details and a device in use.

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

In accordance with one aspect of the invention, an apparatus is provided for sensing an analyte in a fluid. To illustrate this aspect of the invention, an analyte-in-gas sensor 2 according to a presently preferred embodiment of this aspect of the invention is shown in FIG. 1 in conjunction with a patient or other user 1. Although this sensor apparatus could be used in a variety of applications, in this illustrative example it is adapted for use as an acetone sensor for sensing gas or vapor phase acetone in the breath of a human patient or user. Before describing this embodiment in detail, some background on this acetone-sensing application would be useful in appreciating the usefulness of the device and related methods.

Approximately 300 analytes have been identified in human breath. Examples include but are not limited to pentane and other alkanes, isoprene, benzene, acetone and other ketones, alcohols such as ethanol, methanol, isopropanol, ammonia, reflux, medication, and substances which interfere with common alcohol detection systems such as acetaldehyde, acetonitrile, methylene chloride, methyl ethyl ketone, and toluene. Some analytes are in vapor form while others may be in particle form.

Ketone bodies provide a supplementary or substitute form of energy that can be used during various metabolic states including stress, starvation, caloric regulation, or pathology. Breath acetone levels, for example, often are elevated during various metabolic states including stress, starvation, caloric regulation, or pathology such as diabetes and epilepsy. Oftentimes in diabetics, for example, low insulin levels and elevated blood glucose levels result in high concentrations of ketones in the body. This could potentially cause diabetic ketoacidosis ("DKA").

Patients in DKA commonly experience many symptoms such as nausea, fatigue, and rapid breathing. They also emit a fruity odor in their breath, which is distinct and attributable to acetone. Acetone is a volatile ketone body released into alveolar air. If left untreated, DKA can result in coma or even death. However, DKA often is preventable if ketone levels are monitored and treatment is sought when ketone counts are high. The current methods of ketone measurement are blood and urine analysis. The current blood tests typically are accurate, but their invasive nature is undesirable and frequently causes patients to delay treatment. Blood tests also are expensive, as a number of products are needed, including a lancet for blood letting, test strips, a specialized device and batteries. Several studies show that urine analysis is not accurate.

Ketone monitoring also is becoming recognized as a tool for nutritionists or health care professionals to monitor lipid metabolism during dieting. Several studies show that breath acetone concentrations represent lipid metabolism during a calorie deficit. Obesity has become increasingly prevalent and has now reached epidemic levels. It is consequently of great concern to healthcare professionals. Much effort has been invested in treating obesity and promoting healthy weight loss programs for obese individuals. For treatment of obesity, a sensor that measures fat burning would permit patients, doctors and nutrition advisors to adjust weight management plans to individual physiology. A non-invasive, inexpensive, simple-to-use acetone sensor would be an appropriate tool for nutritionists, physicians, and the general public who seek to monitor fat metabolism.

In view of this, sensor 2, while merely illustrating preferred embodiments and method implementations of various aspects of the invention, is specifically adapted to analyze the breath of a patient or other user 1 to sense the specific analyte acetone in the gas phase that constitutes the user's breath as it is expired into the sensor 2. Moreover, this sensor 2 provides the ability to sense acetone levels in the breath of an individual with relatively high accuracy to aid in assessment and treatment in areas such as those described herein above.

Sensor 2 comprises a fluid collecting device for collecting the fluid containing the analyte. Sensor 2 further comprises a fluid input in fluid communication with the fluid collecting device for inputting the fluid containing the analyte in to the fluid collecting device. The fluid collecting device may be or comprise any apparatus that is configured to contain the analyte. Similarly, the fluid input may be or comprise any apparatus that is configured to input the fluid containing the analyte into the fluid collecting device. For example, the fluid collecting device may be or comprise one or more of the following: a conduit, a cavity, a sample collection bag (e.g., a Tedlar bag), etc. The fluid input device may be or comprise one or more of the following: a mouthpiece, a flow controller, a flow restrictor, a filter, a valve, a sterile piece, an injection port, an opening/orifice, a sampling pump, a face mask, a breathing tube, etc.

As specifically embodied in sensor 2, the fluid collecting device comprises a gas collecting device comprising a conduit 4. Other fluid or gas collecting device designs, however, are possible and may be used, provided that the fluid collecting device physically contains or directs the flow or position of the fluid so that it can undergo the desired reaction or interactions as described more fully herein below.

Modified or alternative fluid or gas input devices also may be used. Mouthpiece 3, for example, may be equipped with such modifications as a one-way valve, a pressure regulator, a flow rate regulator, a dessicant or dehumidifier, and the like.

A range of analytes can be sensed using embodiments and method implementations of the invention according to its various aspects. In addition, embodiments and methods can be used to sense one analyte or more than one. Examples of analytes and applications that are amenable to these aspects of the invention include but are not limited to the following primary market groups:

(a) Medical devices/nutritional monitors—breath analysis;
(b) Chemical toxicity and/or occupational health and safety compliance—breath analysis for employees who work in an environment where they are inhaling chemicals—e.g., to assess such things as how much are they exhaling, how much is being internalized, whether they are within acceptable limits, etc.;
(c) Law enforcement—e.g., drug or alcohol testing (G-HBA, cannabis, ethanol, etc.); and
(d) Environmental monitoring.

One area of particular interest involves breath analysis. Included among illustrative breath constituents, i.e., analytes, that have been correlated with disease states are those set forth in Table 1, below. As noted, there are perhaps 300 volatile organic compounds that have been identified in the breath, all of which are candidate analytes for analysis using such embodiments and methods. Additionally, in some instances combinations of constituents (analytes) in breath may serve as a superior disease marker relative to the presence of any single analyte.

TABLE 1

| No. | Candidate Analyte | Illustrative Pathophysiology/Physical State |
|---|---|---|
| 1. | Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise |
| 2. | Ethanol | Alcohol toxicity, bacterial growth |
| 3. | Acetaldehyde | |
| 4. | Ammonia | Liver or renal failure, protein metabolism |
| 5. | Isoprene | Lung injury, cholesterol synthesis, smoking damage |
| 6. | Pentane | Lipid peroxidation (breast cancer, transplant rejection), oxidative tissue damage, asthma, smoking damage, COPD |
| 7. | Ethane | Smoking damage, lipid peroxidation, asthma, COPD |
| 8. | Alkanes | Lung disease, cancer metabolic markers |
| 9. | Benzene | Cancer metabolic monitors |
| 10. | Carbon-13 | *H. pylori* infection |
| 11. | Methanol | Ingestion, bacterial flora |
| 12. | Leukotrienes | Present in breath condensate, cancer markers |
| 13. | Hydrogen peroxide | Present in breath condensate |
| 14. | Isoprostane | Present in breath condensate, cancer markers |
| 15. | Peroxynitrite | Present in breath condensate |
| 16. | Cytokines | Present in breath condensate |
| 17. | Glycans | Glucose measurement, metabolic anomalies (e.g., collected from cellular debris) |
| 18. | Carbon monoxide | Inflammation in airway (asthma, bronchiestasis), lung disease |
| 19. | Chloroform | |
| 20. | Dichlorobenzene | Compromised pulmonary function |
| 21. | Trimethyl amine | Uremia |
| 22. | Dimethyl amine | Uremia |
| 23. | Diethyl amine | Intestinal bacteria |
| 24. | Methanethiol | Intestinal bacteria |
| 25. | Methylethylketone | Lipid metabolism |
| 26. | O-toluidine | Cancer marker |
| 27. | Pentane sulfides | Lipid peroxidation |
| 28. | Hydrogen sulfide | Dental disease, ovulation |
| 29. | Sulfated hydrocarbon | Cirrhosis |
| 30. | Cannabis | Drug concentration |
| 31. | G-HBA | Drug testing |
| 32. | Nitric oxide | Inflammation, lung disease |
| 33. | Propane | Protein oxidation, lung disease |
| 34. | Butane | Protein oxidation, lung disease |
| 35. | Other Ketones (other than acetone) | Lipid metabolism |
| 36. | Ethyl mercaptane | Cirrhosis |
| 37. | Dimethyl sulfide | Cirrhosis |
| 38. | Dimethyl disulfide | Cirrhosis |
| 39. | Carbon disulfide | Schizophrenia |
| 40. | 3-heptanone | Propionic acidaemia |
| 41. | 7-methyl tridecane | Lung cancer |
| 42. | Nonane | Breast cancer |
| 43. | 5-methyl tridecane | Breast cancer |
| 44. | 3-methyl undecane | Breast cancer |
| 45. | 6-methyl pentadecane | Breast cancer |
| 46. | 3-methyl propanone | Breast cancer |
| 47. | 3-methyl nonadecane | Breast cancer |
| 48. | 4-methyl dodecane | Breast cancer |
| 49. | 2-methyl octane | Breast cancer |
| 50. | Trichloroethane | |
| 51. | 2-butanone | |
| 52. | Ethyl benzene | |
| 53. | Xylene (M, P, O) | |
| 54. | Styrene | |
| 55. | Tetrachloroethene | |
| 56. | Toluene | |
| 57. | Ethylene | |
| 58. | Hydrogen | |

Examples of other analytes would include bromobenzene, bromochloromethane, bromodichloromethane, bromoform, bromomethane, 2-butanone, n-butylbenzene, sec-butylbenzene, tert-butylbenzene, carbon disulfide, carbon tetrachloride, chlorobenzene, chloroethane, chloroform, chloromethane, 2-chlorotoluene, 4-chlorotoluene, dibromochloromethane, 1,2-dibromo-3-chloropropane, 1,2-dibromoethane, dibromomethane, 1,2-dichlorobenzene, 1,3-dichlorobenzene, 1,4-dichlorobenzene, dichlorodifluoromethane, 1,1-dichloroethane, 1,2-dichloroethane, 1,1-dichloroethene, cis-1,2-dichloroethene, trans-1,2-dichloroethene, 1,2-dichloropropane, 1,3-dichloropropane, 2,2-dichloropropane, 1,1-dichloropropene, cis-1,3-dichloropropene, trans-1,3-dichloropropene, ethylbenzene, hexachlorobutadiene, 2-hexanone, isopropylbenzene, p-isopropyltoluene, methylene chloride, 4-methyl-2-pentanone, methyl-tert-butyl ether, naphthalene, n-propylbenzene, styrene, 1,1,1,2-tetrachloroethane, 1,1,2,2-tetrachloroethane, tetrachloroethene, toluene, 1,2,3-trichlorobenzene, 1,2,4-trichlorobenzene, 1,1,1-trichloroethane, 1,1,2-trichloroethane, trichloroethene, trichlorofluoromethane, 1,2,3-trichloropropane, 1,2,4-trimethylbenzene, 1,3,5-trimethylbenzene, vinyl acetate, vinyl chloride, xylenes, dibromofluoromethane, toluene-d8, 4-bromofluorobenzene.

Embodiments and methods according to these aspects of the invention may be employed to measure disease markers in the breath, where either elevated or low levels may be important for diagnostic purposes. As noted above, for example, diabetic ketoacidosis (DKA) is a condition where ketone levels in the body are abnormally high. Hyperosmolar non-ketotic syndrome is a condition where ketone levels in the body are subnormal, meaning that the body is not producing enough ketone bodies for normal functioning. While in some embodiments, the sensor may be employed to measure changes in analyte concentrations in a fluid, it is not limited to this and can measure absolute concentrations instead or as well.

Sensor 2 further comprises an analyte interactant 6 (or "interactant 6") that, when contacted by the analyte of interest—here acetone—reacts to cause a change in thermal energy within the fluid collecting device. The analyte may be any substance that is capable of reacting with the analyte to cause the desired change in thermal energy. Although the list of candidate analyte interactants provided here is not necessarily exhaustive, presently preferred analyte interactants would include those described herein, and others as well. "React" as the term is used herein includes not only chemical reaction, but other forms of reaction in which the state of the analyte and/or analyte interactant, their properties or state, or the properties or state of their environment is changed. Examples of reaction regimes might include, for example, physical or chemical absorption or adsorption, physical or chemical reaction, Van der Waals interactions, transitions that absorb or release thermal energy, and the like.

The analyte interactant is in fluid communication with the fluid collecting device in the sense that the analyte interactant is positioned relative to the gas collecting device so that the gas received into the gas collecting device contacts the analyte interactant so that the desired or anticipated analyte-analyte interactant reaction can occur. Preferably, and particularly where the fluid collecting device comprises a cavity or conduit, the analyte interactant is positioned within the cavity or conduit so that at least a portion of the fluid entering the cavity or conduit is caused or permitted to contact and react with the analyte interactant. Alternative designs, however, are possible. An example would comprise placing the analyte interactant at an exit orifice of the fluid collecting device or outside of but immediately adjacent to a portion of the fluid collecting device.

The change in thermal energy associated with the analyte and analyte interactant reaction may involve an increase or a decrease. This thermal energy change may and preferably does have associated with it a change in associated temperature of materials associated with or constituting the sensor 2, but may be used directly, for example, by utilizing a thermal energy flow isothermally.

The analyte interactant 6 preferably is disposed on a substrate such as substrate 7 in FIG. 1 to physically support the interactant and to receive at least a portion of the thermal energy liberated by the analyte-analyte interactant reaction, or to provide thermal energy where the reaction consumes thermal energy.

Sensor 2 also comprises a thermal sensor 5 that in this illustrative embodiment comprises at least one thermocouple, thermopile device, or pyroelectric device thermally coupled to the gas collecting device to generate a signal in response to the change in thermal energy. The signal comprises information useful in characterizing the analyte. The thermal sensing device is thermally coupled to the gas collecting device in the sense that the thermal sensing device, or at least a portion of the thermal sensing device that is used for sensing thermal energy, is disposed so that it can sense at least a portion of the thermal energy generated by the analyte-analyte interactant reaction. The thermopile device therefore need not necessarily be located within the gas collecting device, although preferably it will be located within the gas collecting device or contiguous with it, e.g., such as by forming a wall or panel of the gas collecting device.

"Thermocouple" as the term is used herein is used in its common or ordinary meaning in the fields of physics and engineering and comprises a temperature or thermal energy sensing or measuring device in which a first material is joined or contacted with a second material different from the first material so that an electromotive force is induced by thermoelectric effect when the first and second materials are at different temperatures. The term "thermoelectric thermometer" also is used to describe a thermocouple. The first and second materials used to construct the thermocouple usually are conductors such as metals, alloys, or liquid thermoelectric materials that may or may not contain dopants.

The thermocouple comprises a point of contacts that are called "thermoelectric junctions." One of the junctions is referred to as a "reference junction" and the other is referred to as a "sensing junction." A temperature gradient between the two thermoelectric junctions causes electrons to travel toward the colder region which causes a potential difference between the junctions. This is called the "thermoelectric effect."

This potential difference or voltage between the two junctions is described as follows: $V = n \cdot S \cdot \Delta T$ where V is the voltage, n is the number of thermocouples, S is the Seebeck coefficient of the two metals, and $\Delta T$ is the temperature difference between the sensing and reference junctions. Amongst pure metals, antimony and bismuth have the highest Seebeck coefficient.

The thermal sensing device or thermal sensor as implemented in illustrative sensor 2 comprises a thermopile device 8.

A "thermopile" as the term is used herein is used in its common and ordinary meaning in the fields of physics and engineering to refer to a device that comprises a plurality of thermocouples connected in series. The voltage output of a thermopile is proportional to the Seebeck coefficient of the metals, the number of thermocouples, and the temperature difference between the sensing and reference junctions.

There is design flexibility in the physical relationship of the analyte interactant and the thermal sensor, provided that at least a portion, and preferably most, of the thermal energy from the analyte-analyte interactant reaction is communicated to the sensing portion of the thermal sensor 5. One approach is to place the analyte interactant on or immediately adjacent to the sensing portion of the thermal sensor. In sensor 2, for example, one preferably would coat the sensing junctions, and not the reference junctions, of the thermocouple or thermopile, with the analyte interactant.

An exploded cross sectional view of sensor 2 depicting details of the thermal sensor 5 is shown in the lower right portion of FIG. 1. That cross sectional view shows the analyte interactant 6 disposed on a substrate 7. Immediately below the substrate 7 lies the thermopile device 8, and immediately below it is a thermal insulating material.

Figure 2:
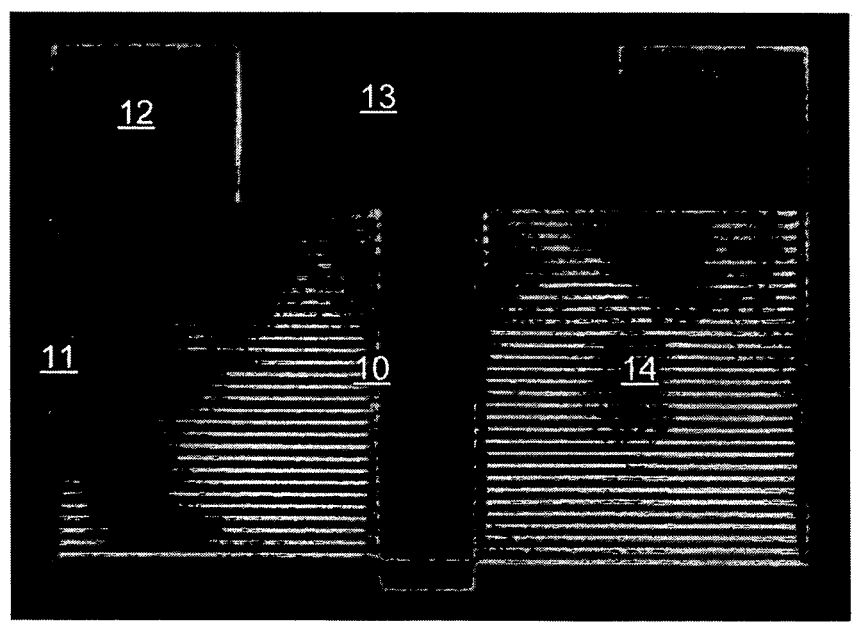
FIG. 2 is a schematic top view of a rectangular thermopile suitable for use in FIG. 1.

FIG. 2 shows a schematic top or plan view of a rectangular thermopile device 8 suitable for use in the thermal sensor 5 shown in FIG. 1. The thermopile device 8 comprises two dissimilar conductors that are deposited on a substrate 13 as alternating strips of conductors 14. The conductors are patterned such that there are two sets of junctions between conductors, the sensing junctions 10 and the reference junctions 11. One of the conductors spans the distance between any reference and sensing junction, which are all in series electrically. As a result, the voltage between the contact pads 12 is the sum of the EMFs of the individual thermocouples which are each made up of a single sensing junction (from the sensing junction set 10) and a single reference junction (from the reference junction set 11). Normally thermopiles are arranged to have an equal number of each. As illustrated in FIG. 2, there are about 60 of each in this embodiment.

Sensor 2 optionally may and preferably will further comprise a processing device operatively coupled to the thermocouple device to receive the signal and process it. This processing device may comprise any device capable of performing the processing desired of the sensor 2, e.g., as described herein. Preferably, however, the processing device comprises a microprocessor or microcontroller, as will be described in greater detail herein below.

The voltage output of the thermopile device 8 can be measured directly or by use of this processing device. The processing device may report the voltage or may convert the voltage to a concentration or other interpretable signal. This conversion may be programmed by use of a calibration curve, look-up table, or other method.

Optionally, the processing device may be used to provide feedback, which feedback can be programmed to analyze the status and transmit commands to operate similar to a drug delivery device.

The thermopile voltage will vary as a function of the temperature difference across its sensing and reference junctions, which normally will change over the course of the analyte-analyte interactant enthalpic interaction. For instance, certain chemical reactions propagate and get increasingly more exothermic as they proceed. Additionally, depending on such things as the flow conditions, the output voltage may change. Therefore, it may be necessary for the processing device to process the signal to ascertain information about the reaction system and to translate the sensor-derived signal into useful information usable by the user. Examples of the types of signal characteristics or responses that have been found meaningful with devices and methods according to this aspect of the invention include the peak voltage, the slope of the voltage versus time curve, the area under the voltage versus time curve, the time to reach various signal features, and the steady state values, etc. Depending on the time over which the analyte interacts with the interactant, different signals may be more indicative of the analyte concentration.

Sensor 2 may also be or comprise a pyroelectric device that is adapted to sense thermal energy from an analyte-analyte interactant reaction in a fluid. Among thermal sensors, pyroelectric materials tend to exhibit fast response times. Additionally, the response of a pyroelectric material to a given energy input may be orders of magnitude greater than other thermal sensors. Embodiments and methods involving the pyroelectric sensor can be applied to fluids broadly, which includes not only gases but liquids as well.

Pyroelectric materials produce an electric current when heated or cooled. Pyroelectrics measure the rate of change of temperature as shown in the following equation:

$$I = p(T) \cdot A \cdot \frac{dT}{dt}$$

where I is current, A is surface area of the sensing element, p(T) is the pyroelectric coefficient, which is a function of temperature, and T is temperature.

Fundamentally, the crystal lattice of certain materials, including ferroelectrics, includes nonsymmetrical bound ions. These ions give rise to spontaneous electric polarization. As with other thermal detectors, the response of the pyroelectric sensor is generally improved if the detector thickness and volumetric heat capacity are minimized.

There are a number of pyroelectric materials that can be employed in various embodiments and methods according to this aspect of the invention. For instance, synthetic and natural (e.g., minerals and ionic crystals) materials may be used. Some examples of pyroelectric materials would include: triglycine sulfate, quartz, tourmaline, gallium nitride, polyvinyl fluorides (e.g. PVDF), lithium tantalate, lead zirconate titanate, lead titanate, etc. It should be understood that any other material or combination of materials that exhibit appropriate pyroelectricity may be a candidate for use.

It is important to note the relationship between the pyroelectric relaxation frequency and the frequency of the heat input modulation. The response of the pyroelectric element typically is enhanced by high-frequency heat. Thus, it is usually helpful if the signal is pulsed or in some way modulated or chopped. This signal can be modulated by a number of different techniques and examples are provided hereinafter. However, as is discussed herein, this modulation is not always necessary.

This pyroelectric chemical sensor may be employed in a number of different applications and environments to measure a number of analytes. For example, a pyroelectric chemical sensor can be used to measure analytes in liquids or gases. Examples of liquids include blood, synovial fluid, spinal fluid, urine, water-based solutions, etc. The array of analytes is also extremely broad. Also, the analyte interactants that can be used with embodiments and methods that employ pyroelectric sensors are broad, as described herein (examples include absorbents, adsorbents, chemical reactants, hydrogenation reagents, aptamers, vapochromic materials, lectins, antibodies, etc).

As may be appreciated from this description, the sensor may be used in a wide variety of implementations and methods. Moreover, the sensor may be used in conjunction with different components that may, for example, aid in the regulation, interpretation, and/or maintenance of the environment and conditions surrounding analysis. As such, the sensor or processing unit (e.g. microprocessor, microcontroller) may be required to process a substantial amount of information. As such, it may be desirable to test a variety of different signal interpretation methods to determine a reliable indicator of analyte concentration or presence.

The output of the thermal sensor, e.g., the voltage/current versus time curve, may be analyzed in a number of ways, including the peak-to-peak difference, maximum value, minimum value, slope of the curve, area under the curve, time to reach certain points, steady state values, etc. Different methods may be employed to determine these features. For example, the area under the curve may be computed using the Trapezoid Rule or the Midpoint Rule. Or, the slope may be computed using, for example, ten data points or one hundred data points, depending on the situation.

Additionally, combinations of such features and interactions of such features can be considered. For example, if the steady state value is above value=X, then the peak to peak difference ought to be interpreted according to method Y. Alternatively, if the area under the curve=X, this means that the flow rate=Y and if the flow rate=Y, then the peak-to-peak difference can be scaled by factor Z to more accurately predict the concentration of the analyte. These are mere examples; others of course may be implemented depending on the components, signal, circumstances, conditions of analysis, analyte-analyte interactant interaction, etc.

In addition to the output of the thermal sensor, other factors may also be considered. For example, the processor may need to consider the output of multiple thermal sensors which are coated with the same analyte interactant. In this instance, the processor may average the outputs or it may discard outliers prior to analysis. In other instances, the processor may need to consider the output of multiple thermal sensors each of which is coated with a different analyte interactant. This may affect the processing algorithm. For example, perhaps the processor interprets the output of thermal sensor #2 to mean that the concentration of analyte #2 is X; the processor may then interpret the output of thermal sensor #5 accounting for fact that the concentration of analyte #2 is X.

In analyzing the signal, the processor may also need to account for the output of components other than the thermal sensor. For example, the processor may be coupled to a flow measuring device, an ambient temperature gage, a filtering unit, or a combination of components. In such instances, the algorithm for signal interpretation may be more complex and involve multiple steps.

Additionally, the processor may be coupled to buttons or some type of user interface. In such instances, user preferences may, in part, dictate the output of the device. For example, if the user inputs the ambient temperature, the presence of interfering substances in his or her breath, a certain disease state, a certain error tolerance or required specificity, etc, the processor may elect certain algorithms to use in the analysis of the data received.

The output of the processing device or the thermopile can be quantitative or qualitative, depending on the application, use, design objectives, etc. For example, an acetone sensor designed for pediatric patients may be equipped with colored indicators that correlate with the seriousness of diabetic ketoacidosis. However, for physicians, the exact concentration of acetone may be displayed.

Having described the basic components of illustrative sensor 2, an illustration of a preferred implementation of a method for its operation in accordance with another related aspect of the invention will now be described. With reference to FIG. 1, a user 1 blows into mouthpiece 3. The breath passes through the mouthpiece 3 into gas collecting device conduit 4 where thermal sensor 5 comprising thermopile 8 is located. The analyte in the breath diffuses to or otherwise contacts the surface of sensor 5 where it contacts the analyte interactant 6 and reacts with it in an enthalpic process. The heat generated or consumed from this process is transferred through substrate 7 to the sensing junctions of thermopile 8, thereby raising or lowering the temperature of the sensing junctions. This heat generation or consumption causes a temperature difference between the sensing and reference junctions of thermopile 8, thereby producing a change in the voltage produced by the thermopile 8 and thus the sensor 5. This voltage therefore comprises a signal representative of the thermal energy change associated with the enthalpic reaction. Stated differently, the output voltage is proportional to the temperature difference between the junction sets, which temperature difference is related to the heat generated or consumed by the analyte interactions, which in turn is related to the amount of the analyte present in the gas. The thermopile 8 is typically thermally insulated from the ambient by a suitable insulator 9, and therefore the signal represents an accurate measurement of the thermal energy change associated with the analyte-analyte interactant reaction. From this signal and the embodied thermal energy change, an assessment may be made as to whether the analyte-analyte interactant reaction involved acetone as the analyte. It also may be used to assess the amount and/or concentration of the acetone analyte in the gas stream.

Generally speaking, the reference junctions compensate for changes in the temperature of the gas stream. If the reference junction temperature were fixed by placing the junctions over a heat sink or insulating them, for example, then a non-interaction effect such as a change in the gas stream temperature would cause a temperature difference between the reference and sensing junctions. In medical applications, this typically is a concern. When the breath expired by the patient passes over the sensor, the thermopile will experience a non-interaction based temperature change merely due to the fact that expired breath is close to body temperature which is close to 37° C. If the sensor is originally contained in an environment which is at 37° C., this may not be an issue. If the thermopile was at room temperature originally and the temperature of the reference junctions was fixed, then the sensor would register a voltage that is proportional to a temperature change between body and room temperature. However, if both the reference and sensing junctions are exposed to the gas stream, then the thermopile will register a temperature change of zero because of the thermopile's inherent common mode rejection. This common mode rejection ratio is a property of thermopiles that operate differentially.

Figure 38:
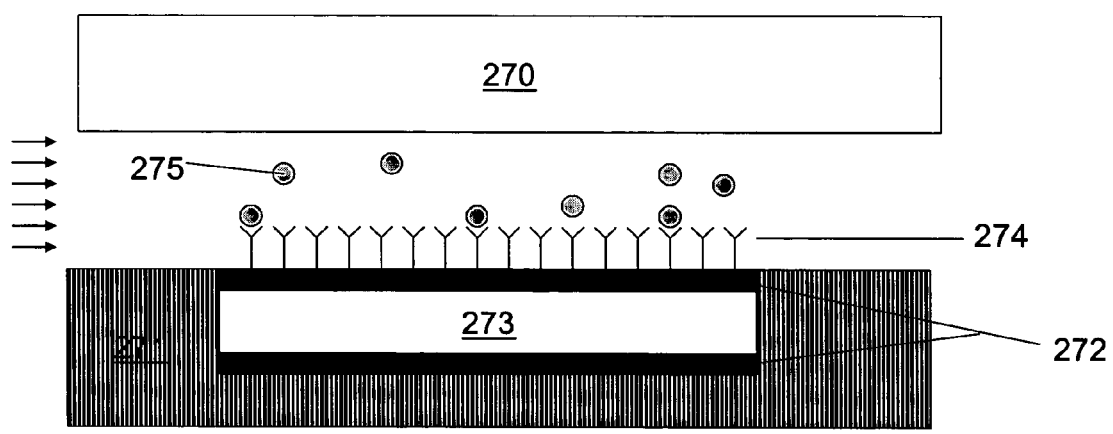
FIG. 38 is an embodiment of a pyroelectric sensor with immobilized analyte interactant.

FIG. 38 shows an embodiment of a simple pyroelectric chemical sensor. In it, the pyroelectric material 273 is sandwiched between two electrodes 272. One of the electrodes 272 is coated with an analyte interactant 274. The analyte 275 is transferred to the analyte interactant 274 where an enthalpic interaction occurs that transfers heat to the sensor. This sensor may be placed in a flow chamber 270 with insulation 271.

The phenomenology and characteristics of the gas flow can impact the operation of analyte sensing devices such as sensor 2. The details of the gas flow can influence a number of factors bearing upon the operation of the device, for example, such as local concentrations of analyte, particularly at the interface between the analyte and the analyte interactant (the "analyte-analyte interactant interface"), where the analyte-analyte interactant reactions occur or are initiated, the local temperature at the analyte-analyte interactant interface, the formation and existence of boundary layers or fluid layers that can influence diffusion of analyte to the interface, the diffusion of reaction products away from the interface, the diffusion of thermal energy away from the interface, etc., the residence time of the gas and thus the analyte at the analyte-analyte interactant interface, and others. Therefore, the design and performance of such analyte sensing devices can be improved through careful consideration of these flow characteristics.

Flow properties can be affected in a number of ways, including but not limited to such things as the design of the gas input, the gas collecting device, the thermal sensor device, and the interaction of the various components. The conduit 4, for example, may be cylindrical, rectangular or any of a variety of shapes that allow the analyte to reach the thermal sensor 5. The mouthpiece 3 may be detachable and replaceable. Alternately the conduit 4 may be as narrow as the mouthpiece 3. For situations in which the analyte is transferred to the thermopile or pyroelectric 8 purely or predominantly by diffusion, the conduit 4 may comprise an overlying shelter to protect the sensor from particles such as dust.

The gas can come into contact with the thermal sensor in various ways. These various ways can impact the flow regime of the gas. When a fluid comes into contact with a surface, there is a no-slip boundary condition and the velocity at the surface is therefore zero or essentially zero. The velocity therefore varies between zero and the bulk velocity. The distance between the surface and the point at which molecules are traveling at 99% of the bulk velocity is known as the "hydrodynamic boundary layer." As the distance from the leading edge of the surface increases, the thickness of the hydrodynamic boundary layer increases. If the fluid is passing through a conduit, the hydrodynamic boundary layer is limited by the dimensions of the conduit such as the height or diameter.

If the surface is coated with a chemical, such as an analyte interactant, then a concentration boundary layer for the analyte will form. As with the hydrodynamic boundary layer, the thickness of the concentration boundary layer for the analyte will increase as a function of distance from the leading edge. Therefore, the flux to the surface of the analyte decreases rapidly along the length of the conduit with maximum flux occurring at the leading edge. The diminishing flux can be an important consideration if it is necessary to react the analyte with a chemical, such as the analyte interactant, that is immobilized at the surface.

One way to increase the flux of analyte at and to the surface is to interrupt the growth of the concentration boundary layer. If the analyte interactant is immobilized in a discontinuous fashion such that the interactant is immobilized for a certain distance and followed thereafter by some degree of interruption, then the concentration boundary layer thickness will decay. The interruption may include but is not limited to a non-reactive surface of the same or a greater distance as the adjacent region of analyte interactant. Thereafter, if analyte is present at the surface, the concentration boundary layer will begin to grow again. In this way, the flux of analyte to the surface can be maintained relatively high at each point where there is analyte present. Using this manner of chemical patterning, the flux to the surface of analyte can greatly surpass the flux that would be achieved if the entire surface had been coated with interactant without such interruptions and discontinuities.

There are other ways by which the concentration boundary layer can be interrupted. For example, if the fluid flow changes direction, then both the hydrodynamic and concentration boundary layers will be interrupted. This could happen using a coiled flow path.

Another way to interrupt the concentration boundary layer is to place an obstruction immediately following the immobilized chemical. This obstruction would force the streamlines to change direction and therefore cause turbulence. The boundary layers would reform when the fluid comes in contact with a smooth surface.

Another way to interrupt the concentration boundary layer is to immobilize chemical throughout the chamber, but to inactivate the chemical at the appropriate locations. For instance, if the chemical can be inactivated by exposure to UV light, an appropriate photo-mask can be designed to achieve this.

Preferably, but optionally, the flow of the gas is directed in such a way that all of the analyte in the entering gas stream flows over the junctions of the thermopile or over the pyroelectric device. In this way, fluid flow over the legs of the thermopile between the sensing and reference junctions can be minimized. This is particularly relevant when a bolus of fluid is injected into or exposed to the sensor 2, in which case the number of molecules available for reaction is limited.

The sensor 2 and more specifically the arrangement of the gas collecting device and the analyte interactant may be disposed so that the analyte diffuses from the gas to the analyte interactant wherein the thermal energy is readily transferred to the thermal sensor 5. The design also may be such that the analyte is convected directly to the analyte interactant. The sensor 2 also may be configured so that the analyte is convected across the analyte interactant and diffusion also occurs to bring the analyte in contact with the analyte interactant.

The thermopile device preferably is insulated, and more preferably it is insulated with the metals facing the insulation and the substrate left exposed. On the substrate and over the legs of the thermopile device, barriers are created, wherein the barriers can serve as channel walls by which to direct fluid flow over the thermopile junctions (both reference and sensing). The placement of the channel walls over the legs of the thermopile in presently preferred embodiments does not affect the signal as the thermopile response is proportional to the change in temperature between the reference and sensing junctions, and not any intermediate temperature differentials.

In a preferred embodiment and particularly if the surface reactions are highly exothermic, the channels can be created such that the reference junctions are contained within channels disparate from those containing the sensing junctions. A possible advantage of this embodiment is that lateral heat transfer from the sensing to reference junctions will be minimized. Additionally, if the channels are designed in such a way that the reference junction channels are positioned at the start and end of the entire flow path, the temperature compensation is improved. In other words, the fluid flowing over the sensing junctions may experience an increase in temperature due to the convective heat transfer. Therefore, it is possible that the temperature of the gas will increase as a function of distance through the channels. In this case, therefore, it is desirable that the reference junctions exist at the start and end of the flow path.

Figure 20:
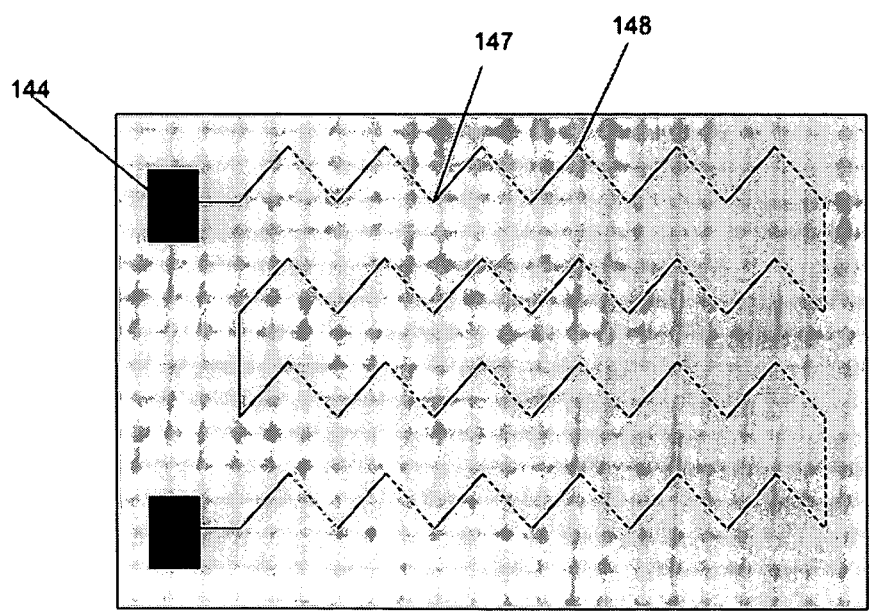
FIG. 20 shows a embodiment of a thermopile.

In a preferred embodiment, the sensing and reference junctions are placed in an alternating fashion along the length of the conduit as shown, for example, in FIG. 20. This may be useful if the flow conditions are such that turbulent flow is expected. In this case, both the sensing and reference junctions would experience the same effect which would help to reduce the effect of thermal noise which may be higher than normal under turbulent flow conditions due to the presence of fluid eddies, etc.

The analyte interactant may be deposited immediately after the leading edge. Assuming an instantaneous reaction, the flux of analyte to the surface is directly proportional to the bulk concentration and square root of the distance from the leading edge and inversely proportional to the square root of the velocity. Immobilizing analyte interactants over large length of the sensor thus becomes inefficient at some point.

In one embodiment, there is a thermal sensor at the top and bottom of the conduit. The thermal sensor at the top and the one at the bottom will both have some chemical (e.g. analyte interactant) immobilized and the fluid will be exposed to both devices. There will be analyte flux (mass transfer) to both the top and bottom devices which will at least double the signal.

In another embodiment, the entering flow stream is divided and directed over a different set of electrically coupled reference and sensing junctions. In this way, the velocity over the immobilized chemical will be less. As the velocity decreases, the analyte has more time to diffuse to the surface as diffusion transport will dominate over convection transport.

Figure 19:
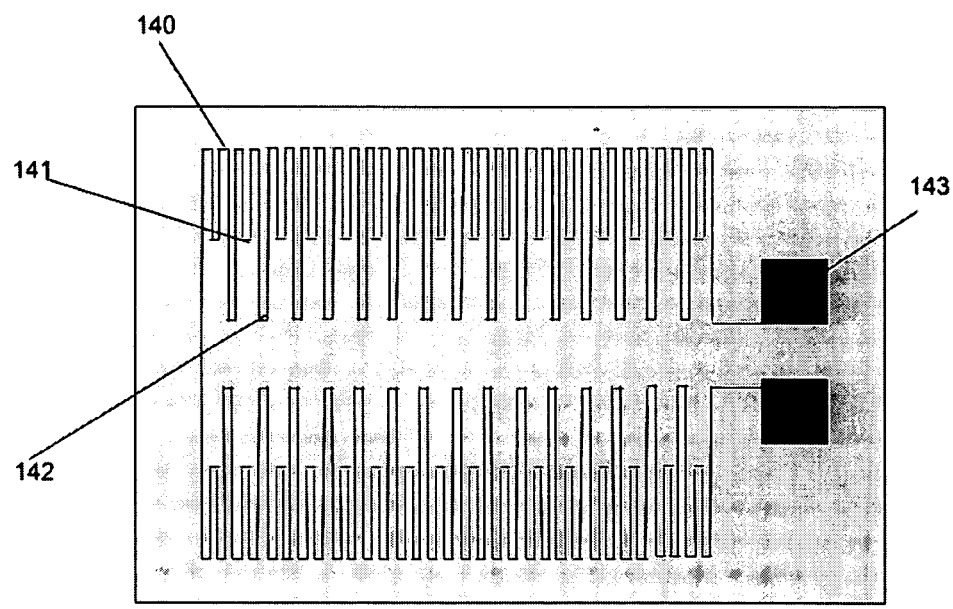
FIG. 19 shows an embodiment of a thermopile.

The design details of the thermopile or pyroelectric 8 can vary, and can be optimized to meet different needs or design objectives. FIGS. 1 and 2 show examples of different thermopile geometries, i.e., rectangular and circular. The rectangular embodiment may be preferred in situations where, for instance, there is flowing gas over the thermopile. The energy consumed or generated at the sensing junctions can be convected downstream instead of to the reference junctions. In the latter case, the signal would be slightly masked. The circular embodiment may be preferred in systems, for example, where the interactant is best immobilized as a droplet or other spherical form. Additionally, the circular geometry provides symmetry to the device where the reference junctions are all equally distributed from the enthalpic process. In these embodiments, the cumulative voltage generated by the individual thermocouples is measured at the thermopile contact pads. To reiterate, however, many different geometries may be used including, for example, those shown in FIG. 19 and FIG. 20.

Multiple thermal sensors may be linked in arrays. Several thermal sensors can have the same interactant to detect the same analyte. Their electrical outputs (voltage, current, etc) could be averaged by a microprocessor with the result that net effect of noise is reduced. Alternatively, the various thermal sensors may be connected in series and the net output transmitted to a microprocessor. Alternatively, each of several thermal sensors may be coated with a different interactant so as to more selectively detect an analyte.

The thermal sensor device can be integrated within a microfluidic gas analysis device. Microfluidic devices have gained significant interest recently due to their ability to perform multiple processes in very short time intervals and in very little space. The thermopile and pyroelectric device are well suited for use in a microfluidic gas analyzer because they are easily miniaturized.

Preferably but optionally, both the reference and sensing junctions of the thermopile device are coated with a non-interactive substance (with respect to the analyte) that helps to equalize the thermal load on both of these junction sets. For example, if an enzyme such as alcohol dehydrogenase is entrapped within a gel matrix, the gel matrix without the enzyme might be placed on the reference junctions and that gel containing the enzyme on the sensing junctions. In another case, both the reference and sensing junctions are coated with a substance like silicone grease. Over the sensing junctions, the silicone grease adheres interactants that are in particle form, such as trichloroisocyanuric acid.

Optionally, the reference junctions may be coated with an interactive substance that is different from the analyte interactant that is placed on the sensing junctions. A configuration also may be used in which two analyte interactants are used, and wherein the analyte interacts with the first analyte interactant at the reference junction in an endothermic process and with the second analyte interactant at the sensing junction in an exothermic process, or the converse.

Optionally, the legs of the thermopile or that area between the reference and sensing junctions may be coated with an analyte interactant. The heat that is consumed or generated in this area could be transferred to the sensing junctions. The temperature difference between the sensing and reference junctions is proportional to the output voltage of the thermopile.

Modulating the input signal to the pyroelectric sensor may be desirable under certain circumstances. As a first example, while mass transfer of the analyte to the reaction sites will, in most cases, vary with time, thereby producing a time varying temperature signature, it may be advantageous to modulate the signal at a higher frequency rate to enhance the pyroelectric sensor response (e.g. heat stimulation frequency is greater than crystal relaxation frequency).

As a second example, modulation may provide a reference such that the pyroelectric sensor may compare the signal to the "noise" of the environment (e.g. to account for non-specific binding, temperature changes in the fluid, etc).

As these input signals are modulated, the pyroelectric sensor output can be processed to maximize the value of the sensor output. The signal processing unit may include a lock-in amplifier (e.g. to discriminate between signal and noise), chopper-stabilized amplifiers, current amplifiers, charge amplifiers, etc.

The ideal modulation frequency can be determined empirically, theoretically, or by other means. An example of a mathematical model that may be helpful in determining ranges of acceptable modulation frequencies is provided.

In this example, determining an appropriate frequency of modulation can account for three primary factors: (1) the thermal time constant (the relaxation constant of the pyroelectric material), (2) the electrical time constant, and (3) the time for a measurable quantity of the analyte to be transferred to the pyroelectric sensor surface (mass transfer limitations).

The thermal and electrical time constants, $\tau_{thermal}$ and $\tau_{electrical}$ respectively, are:

$$f_{-3dB,thermal} = \frac{1}{2\pi\tau_{thermal}} = \frac{1}{2\pi R_{T,eff}C_{T,eff}} \text{ and } f_{-3dB,electrical} = \frac{1}{2\pi\tau_{electrical}} = \frac{1}{2\pi R_E C_E}$$

where $R_{T,eff}$ and $C_{T,eff}$ are the effective thermal resistance and capacitance of the pyroelectric sensor and $R_E$ and $C_E$ are the effective electrical resistance and capacitance of the signal processing interface. To determine the appropriate values for these parameters, we investigate the responsivity ("gain") of the pyroelectric sensor:

$$R_v = \frac{v_0}{p_i} \propto \frac{jwR_{T,eff}R_E}{(1+jwR_T C_T)(1+jwR_E C_E)}$$

where $R_v$ is the responsivity, $v_o$ is the output voltage, and $p_i$ is the input power. Based on the bandpass characteristics and considering the transfer function, the responsivity can be greatest if the modulation (chopping) frequency meets the following constraint for Maximum responsivity: $1/\tau_{elec} < 2\pi f_c < 1/\tau_{thermal}$ where $f_c$ is the chopping (modulation) frequency of the thermal input energy. In some cases, the values of the thermal and electrical frequencies are: $f_{electrical} = 0.1-1$ Hz and $f_{thermal} = 5-35$ Hz. Accordingly, as discussed in this example, there is a range of acceptable values for $f_c$. To further constrain this parameter, the time for mass transfer should be considered.

Equation 1 shows a mathematical model that predicts the molar flux of the analyte to the surface of a pyroelectric sensor whereupon analyte interactants that bind specifically to the analyte are immobilized. This model accounts for the unsteady mass transfer of the analyte via convection and two-dimensional diffusion to the immobilized analyte interactant. Equation 1 was derived from the differential form of the mass balance equation (Conservation of Mass):

$$\frac{\partial u}{\partial t} = D\left(\frac{\partial^2 u}{\partial x^2} + \frac{\partial^2 u}{\partial y^2}\right) - v_x \frac{\partial u}{\partial x} \quad \text{Equation 1}$$

where u is the concentration of the analyte, $v_x$ is the velocity profile for the flow conduit, and D is the diffusion coefficient. The chemical kinetics associated with the analyte-analyte interactant interaction were accounted for via a boundary condition as the reaction was heterogeneous in nature. This equation can be solved via numerical methods in a software program such as MatLab using the following explicit formula:

$$u_{i,j,n+1} = \frac{\alpha \Delta t}{\Delta x^2}[u_{i+1,j,n} - u_{i-1,j,n}] + \frac{\alpha \Delta t}{\Delta y^2}[u_{i,j+1,n} - u_{i,j-1,n}] +$$
$$u_{i,j,n}\left[1 - \frac{\alpha \Delta t}{\Delta x^2} - \frac{\alpha \Delta t}{\Delta y^2}\right] + \frac{\beta \Delta t}{\Delta x}[u_{i+1,j,n} - u_{i,j,n}]$$

This model is useful in studying implications of the geometry of the flow chamber for such parameters as the surface area for interaction, the distance from the leading edge to the chemical patterning, the velocity characteristics, and the distance for diffusion from the bulk stream.

The mass transfer solution may be coupled to a heat transfer model because the heat generation term is equal to $Q(t)=N''(t) \cdot \Delta H_{rxn}$ where N''(t) is the time-varying flux of the analyte to the surface of the pyroelectric sensor and $\Delta H_{rxn}$ is the heat of reaction. The following heat transfer equation is derived from the principle of Conservation of Energy:

$$\rho c_p V \frac{dT}{dt} = Q(t) - hA(T - T_\infty) \quad \text{Equation 2}$$

From this equation, the surface temperature profile may be derived. The pyroelectric sensor outputs current based on the following equation:

$$I = p(T) \cdot A \cdot \frac{dT}{dt} \quad \text{Equation 3}$$

where p(T) is the pyroelectric coefficient, which is a function of temperature, A is the cross-sectional area of the detector element, and dT/dt is the derivative of temperature with respect to time. The temperature differential was computed based on the solution of the energy balance shown in Equation 2.

In this example, based on the operating characteristics of the pyroelectric sensor and circuit, for enhanced signal, the heat input to the pyroelectric sensor should be modulated at some frequency, $f_c$, where $f_{electrical} < f_c < f_{thermal}$. The impact of various values of $f_c$ on the mass transfer to the surface and the corresponding output of the pyroelectric sensor should be determined based by, for example, converting the Q(t) term in Equation 2 into a step-wise defined function with frequency $f_c$. If the current output of the pyroelectric sensor, I, has had an opportunity to reach a maximum value within, for example, two-three times the electrical frequency, the particular value of $f_c$ may be appropriate. Examples of $f_c$ that have been found useful are in the range of 0.5 Hz to 2 Hz. Of course, the frequency of modulation could be greater than or lower than this range of values, depending on the circumstances.

If used correctly, math models can serve as excellent hypotheses for research. Depending on the application, the model can be adapted to, for example, decompose the kinetics parameters to their thermodynamic bases such as bond energies, the Gibbs potential, and other thermodynamic parameters. This may prove useful because when attempting to select analyte interactants, experimentally obtained kinetics parameters may not be readily available and it may be necessary to rely on other properties.

The thermal energy input to the pyroelectric sensor can be modulated or chopped in a number of ways. Various examples are shown hereinafter.

Figure 41:
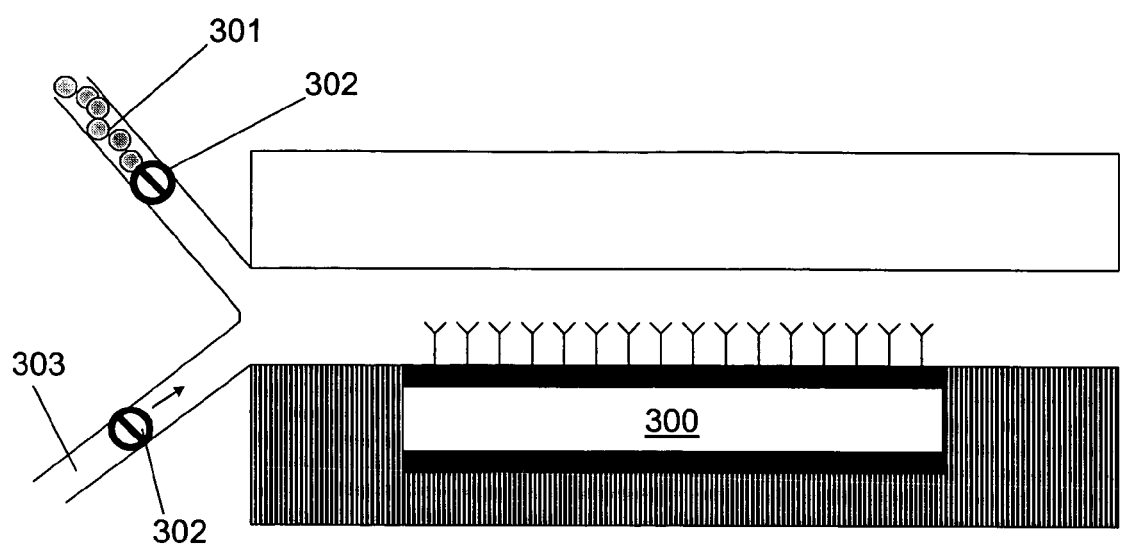
FIG. 41 is an embodiment that utilizes control valves to provide modulation.

One embodiment of the pyroelectric sensor, shown in FIG. 41, involves switching between a fluid (liquid or gas) that contains the analyte 301 and a second fluid 303 that serves as a reference. This can be done, for example, using electrically controlled valves 302.

Figure 42:
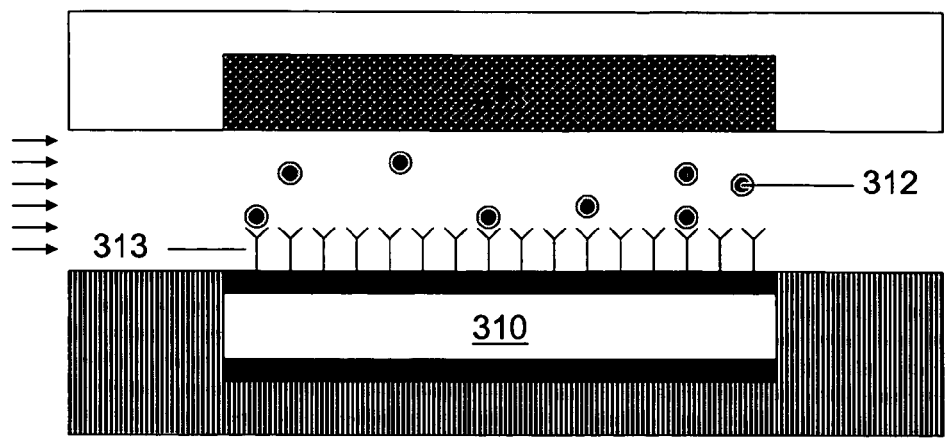
FIG. 42 is an embodiment that utilizes a charged surface.
Figure 42:
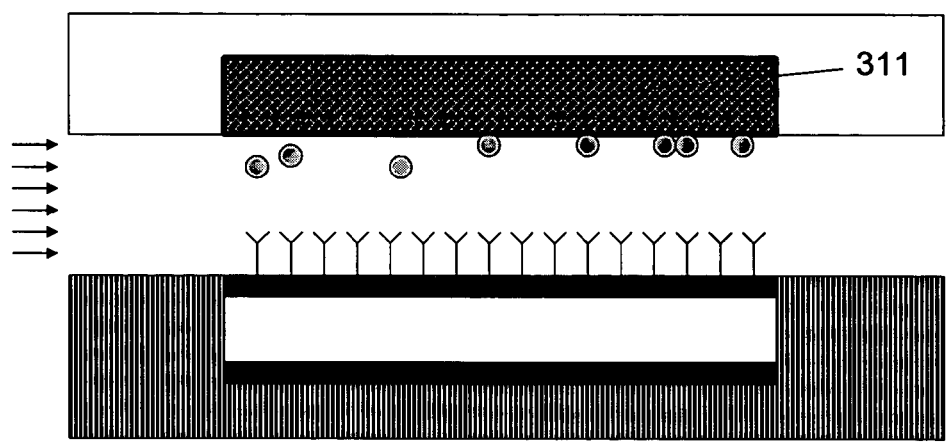

Another embodiment of the pyroelectric sensor involves the use of a charged surface 311. If the sensor 310 is used to measure an analyte 312 that is associated with an electrical charge (e.g. proteins that carry a negative charge), then a chargeable surface 311 may be employed. The charge on this surface will be modulated by a control circuit or the like to attract and release the analyte. FIG. 42 exemplifies this via a two stage storyboard.

Figure 43:
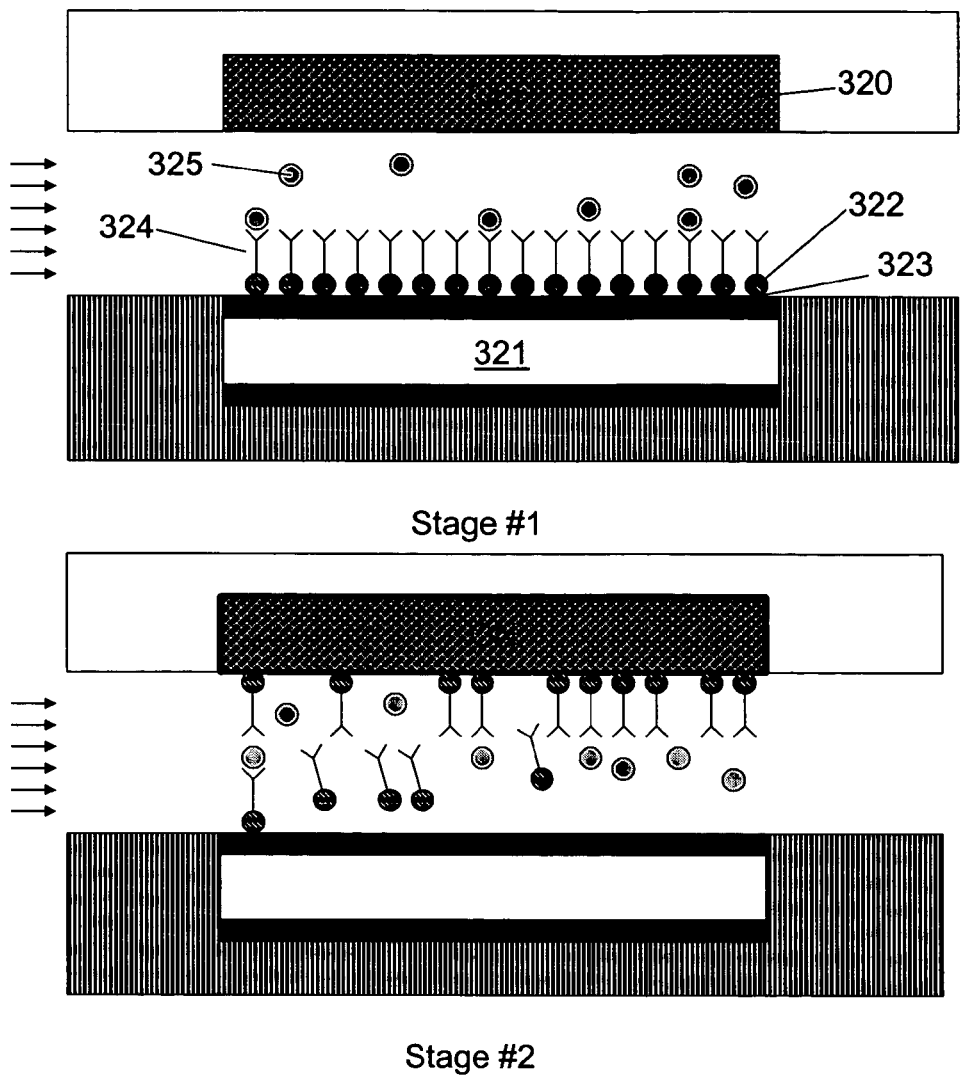
FIG. 43 is an embodiment that utilizes magnetic surfaces.

Another embodiment of a thermal sensor according to an aspect of the invention that uses a pyroelectric sensor involves the use of a magnetic surface 320. Opposite the sensor surface and below the sensor, magnetizable surfaces may be placed. As the magnet is turned on and off, the magnetic beads 322 may move from the sensor surface to the magnetizable surface 320 and vice versa. If the analyte interactant 324 is immobilized on magnetic beads, then the source of binding energy would be modulated from one surface to the other, thereby modulating the sensor signal. An example is shown in FIG. 43.

While these magnetic beads are not limited to any particular embodiment, if the orientation of the bead is important for a given application, then only a point 323 of the bead may be made with a magnetic material.

Figure 44:
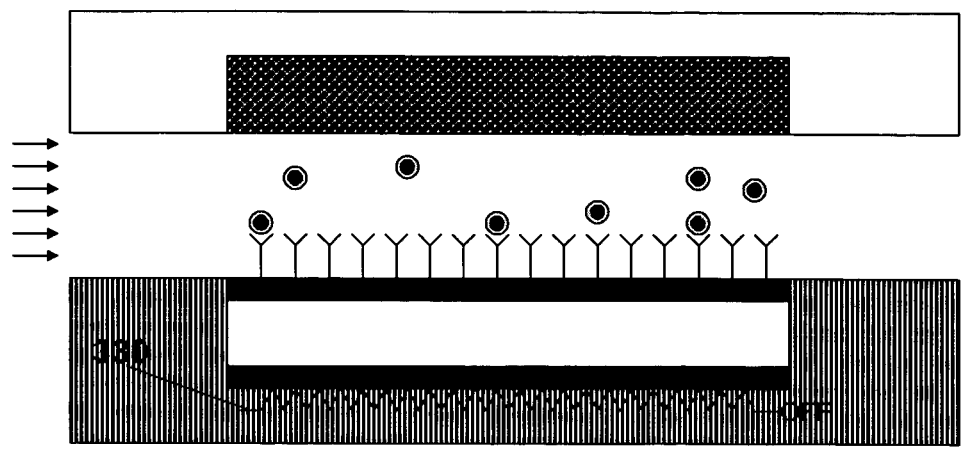
FIG. 44 is an embodiment that utilizes a heater.
Figure 44:
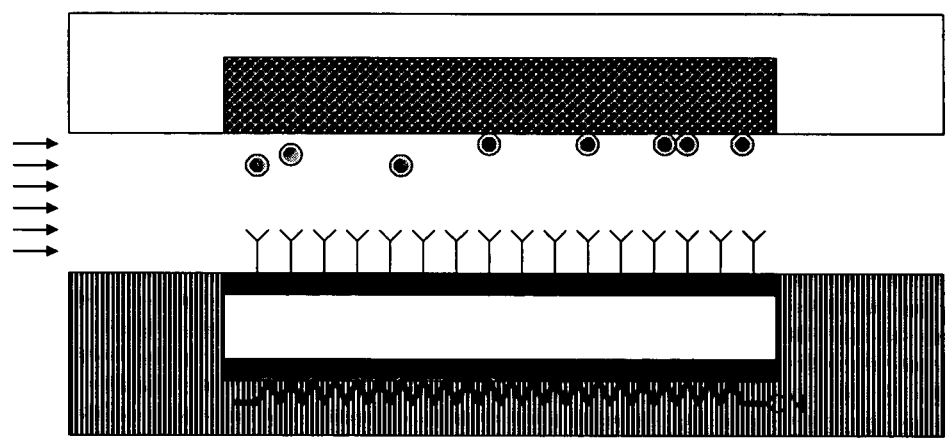

Another embodiment of the pyroelectric sensor involves the use of a heater 330. The energy required for most binding events is temperature-dependent. Therefore, a heater 330 of known and well characterized behavior may be used to release any analyte bound to the analyte interactant on the surface thereby creating a desorption effect, which can be used to modulate the heat input to the pyroelectric sensor. An example of this embodiment is shown in FIG. 44 via a two-stage storyboard.

Figure 45:
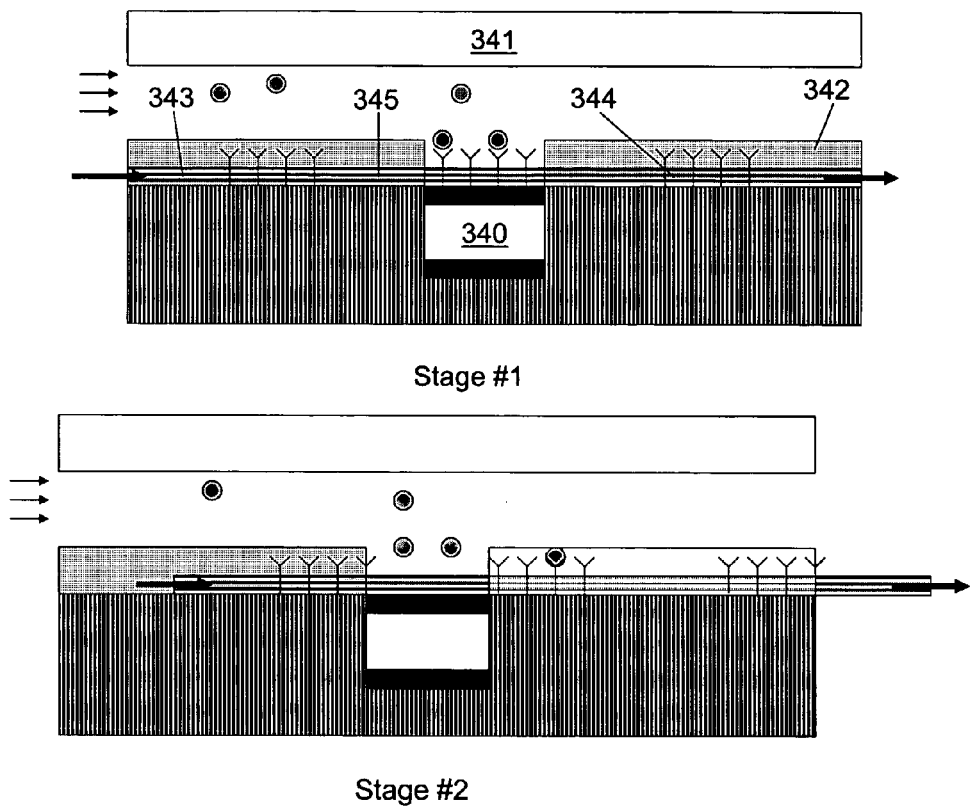
FIG. 45 is an embodiment that utilizes a test strip.

Another set of embodiments of the pyroelectric sensor utilize a chemical patterning technique. In these devices, the analyte interactant 344 is patterned in a discontinuous manner on a test strip 343. This test strip 343 is moved across the thermal detector 340 (e.g. the pyroelectric sensing element). When the analyte interactant (Stage 1) is exposed to the fluid, heat may be generated (if the analyte is present), and this heat will be measured by the detector 340. When the portion of the test strip without analyte interactant 345 is exposed to the fluid, there will be no heat generated (or solely noise, interfering signals, non-specific adsorption will be measured). This embodiment is described in FIG. 45 via a two-stage storyboard.

In some cases, the test strip itself may be conductive (e.g. a metallic foil). This way, any heat that is generated by the interaction of the analyte with the immobilized analyte interactant will be conducted efficiently to the thermal detector.

Alternatively, the test strip may be or comprise a pyroelectric ribbon with patterned analyte interactant. If it is a pyroelectric ribbon, the ribbon may be passed over a second thermal detector or it may simply be passed over electrical contacts (e.g. electrical connectors that make contact with the pyroelectric ribbon).

In devices suitable for consumer applications and the like, it is often desirable to have disposable components. Test strips may also bypass the problem of replacing the analyte interactant.

In such cases, it is possible that the user would input the test strip. An internal device component (e.g. gear with gear belt) could drive the test strip across the thermal sensor. Of course, there are a variety of other mechanisms by which the test strip could be moved across the sensor in the desired fashion.

Figure 46:
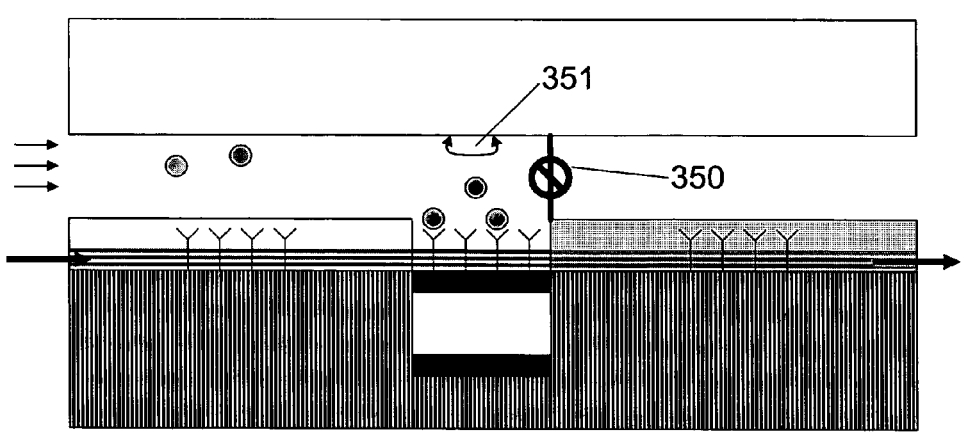
FIG. 46 is an embodiment that utilizes a test strip with a control valve and mixer.

If there is concern that the analyte will have insufficient time to diffuse to the test strip, a control valve 350 such as shown in FIG. 46 may be used. If desirable, a mixer 351 may also be used to facilitate mass transfer to the analyte interactant.

Figure 47:
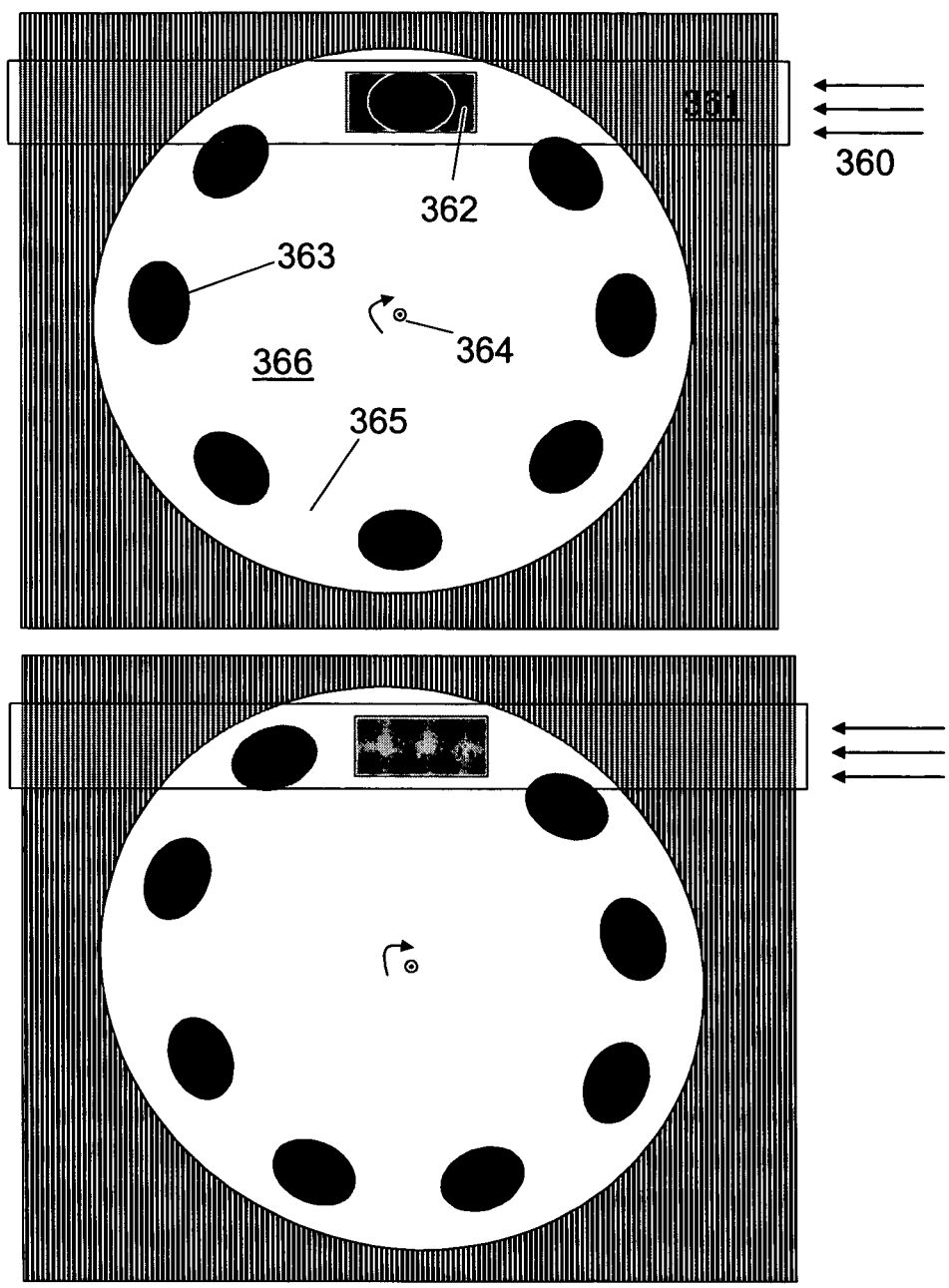
FIG. 47 is an embodiment that utilizes a circular test strip.

The test strip is not limited to any particular geometry. FIG. 47 shows an example of a test strip that is circular. In this embodiment, the analyte 360 enters a conduit 361. The conduit 361 is open to the test strip 366 in a zone 362. The test strip 366 rotates via some rotational mechanism 364 such that the part of the test strip that is present in the zone alternates between depositions of analyte interactant 363 and some non-interacting reference species 365.

Figure 48:
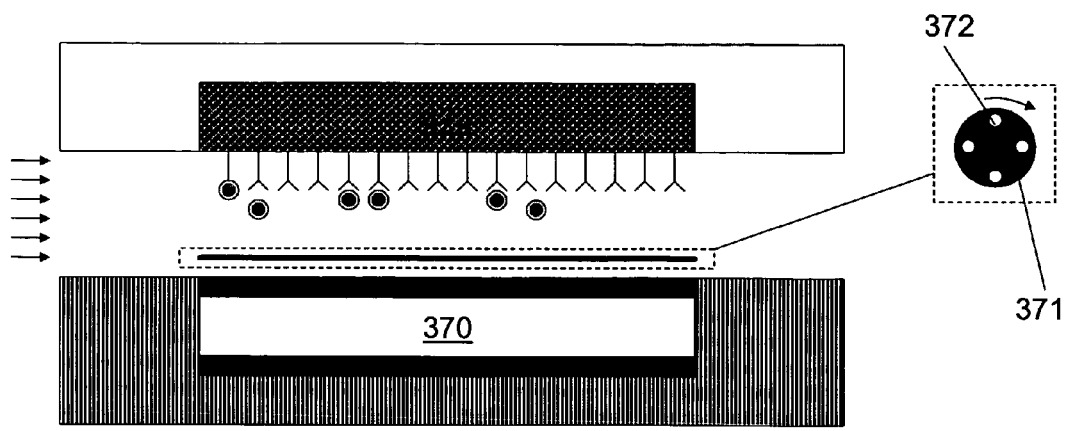
FIG. 48 is an embodiment that utilizes a mechanical chopper.

Another embodiment utilizes a mechanical chopper. This mechanical chopper can be of any particular shape. In FIG. 48, it is shown in a circular design. The mechanical chopper 371 will have "holes" 372 that allow for heat to pass through. An example of such an embodiment is shown in FIG. 48. In this embodiment, heat generated from an interaction between the analyte and analyte interactant, which is immobilized on a surface 373 is measured by a thermal detector 370 and the temperature signal is modulated via a mechanical chopper 371.

Figure 49:
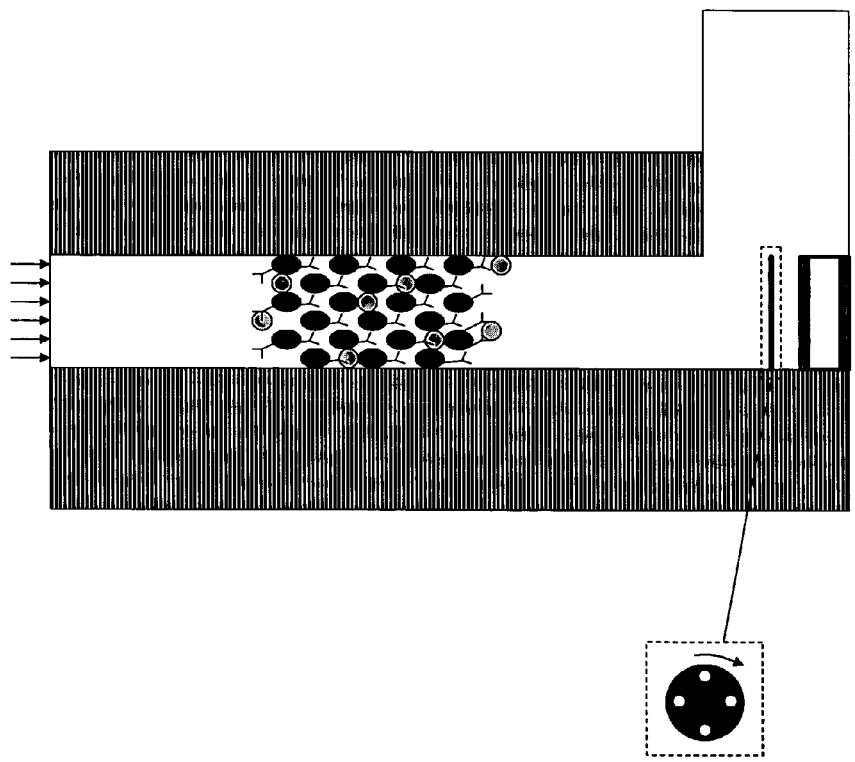
FIG. 49 is an embodiment that utilizes a mechanical chopper to detect thermal energy from a packed bed.

This mechanical chopper can be used in combination with a packed bed as well. An embodiment that utilizes this principle is shown in FIG. 49.

The enthalpic process occurs due to the interaction of the analyte and the reactive analyte interactant substance(s). The analyte interactant can produce or consume heat by any of a variety of ways, including but not limited to chemical reaction, catalysis, adsorption, absorption, binding effect, aptamer interaction, physical entrapment, a phase change, or any combination thereof. Biochemical reactions such as DNA and RNA hybridization, protein interaction, antibody-antigen reactions also can be used to instigate the enthalpic process in this system.

Aptamers are specific RNA or DNA oligonucleotides or proteins which can adopt a vast number of three dimensional shapes. Due to this property, aptamers can be produced to bind tightly to a specific molecular target. Because an extraordinary diversity of molecular shapes exist within the universe of all possible nucleotide sequences, aptamers may be obtained for a wide array of molecular targets, including most proteins, carbohydrates, lipids, nucleotides, other small molecules or complex structures such as viruses. Aptamers are generally produced through an in vitro evolutionary process called "systematic evolution of ligands by exponential enrichment" (SELEX). The method is an iterative process based on selection and amplification of the anticipated tight binding aptamer. The start library for selection of aptamers contains single stranded DNA oligonucleotides with a central region of randomized sequences (up to 1015 different sequences) which are flanked by constant regions for subsequent transcription, reverse transcription and DNA amplification. The start library is amplified by PCR and transcribed to an RNA start pool by T7 transcription. Target specific RNA is selected from the pool by allowing the pool to interact with the target molecule, only tight binding RNA molecules with high affinity are removed from the reaction cycle, the tight binding RNA molecules are reverse transcribed to cDNA and amplified to double stranded DNA by PCR. These enriched binding sequences are transcribed back to RNA which is the source for the next selection and amplification cycle. Such selection cycles are usually repeated 5-12 times in order to obtain only sequences with highest binding affinities against the target molecule.

Interactants can be or comprise adsorbents including but not limited to activated carbon, silica gel, and platinum black. Preferably, the adsorbent can be impregnated with another species that reacts with the analyte following the adsorption. While analyte interactants may be or comprise adsorbents or absorbents, as may be appreciated, they are not limited to them.

Interactants also can be or comprise chemicals or chemical reactants. Suitable chemicals that interact with acetone include but are not limited to halogenated compounds, sodium hypochlorite, hypochlorous acid, sodium monochloroisocyanurate, sodium dichloroisocyanurate, monochloroisocyanuric acid, dichloroisocyanuric acid, and trichloroisocyanuric acid. Alcohol can interact with a chemicals such as chromium trioxide ($CrO_3$) or enzymes such as alcohol dehydrogenase, alcohol oxidase, or acetoalcohol oxidase. Other reactants may be or comprise chloroform, chloroform in the presence of a base, and nitrosyl chloride.

Optionally, the interactant may not directly interact with the analyte, but a byproduct of the interactant and some other compound in the gas can produce a different interactant with which the analyte reactants. A possible reason for selecting such an interactant is for stability; thus, if the true analyte-interacting species is unstable under the particular operating conditions, then it may be desirable to select a more stable interactant that, upon exposure to the analyte or some other substance present in the gas containing the analyte, produces a different analyte interactant. For example, trichloroisocyanuric acid can react with water to form hypochlorous acid, which engages in an enthalpic reaction with acetone.

Vapor phase reactions are sometimes limited because reactions in aqueous solution typically involve acid or base catalysis. Therefore, in the vapor phase, the presence of a catalyst or an activating agent, such as a protonating agent, may be critical to allow the interactant and analyte to interact.

Optionally, analyte interactants also can be or comprise hydrogenation reagents. For acetone, Raney nickel and platinum catalysts are suitable interactants.

The analyte can also interact with materials from living systems or living systems themselves. Examples include but are not limited to microorganisms, cells, cellular organelles and genetically modified versions thereof. These living systems engage in metabolic processes to sustain life which involve energy exchange and therefore heat consumption or generation. Some chemical analytes such as toxins or pathogens kill or damage cells or impair organelle function. If the living material is immobilized on the sensing junctions of a thermopile, therefore, the change in heat generated or consumed is related to the number of living cells which can be related to the presence of a toxin or pathogen.

Optionally, the interactant may be selected such that the interaction with the analyte involves interaction with other substances in the gas, such as water, oxygen, or another analyte.

While not wishing to be limited to any particular mechanism or theory of operation, the thermal energy change sensed at the thermopile device in some cases may comprise heats of condensation. "Phase change agents" can perform a number of functions relevant to latent heat energy. For example, they can facilitate evaporation and/or condensation. With regard to condensation, they can; alter the surface area such that there is more or less condensation over the sensing junctions than the reference junctions; and promote increased (or decreased) condensation based on the phase change agent's properties, for example, increasing condensation may occur over phase change agents that have a greater polarity. To illustrate this further, a powder is placed on the sensing junctions of thermopile device 8 in sensor 2, thus effectively increasing the surface area over the sensing junctions. Breath containing acetone is passed through a moisture filter and then over the thermal sensor 5. The acetone condenses from the breath onto the surface and this condensation causes heat to be generated over the sensing junctions. For a sensor that is operating at standard temperature and pressure ("STP"), the analytes that condense are liquids at STP. Typical breath constituents include: carbon dioxide, oxygen, nitrogen, and water. Apart from water, none of these compounds normally will condense onto a surface under these conditions.

Candidate analyte interactants that may be useful in presently preferred embodiments and method implementations according to various aspects of the invention include organometallic vapochromic materials, such as [Au2Ag2(C6F5)4 (phen)2]n. These types of materials are powders at room temperature, which make them easy to deposit, and react with volatile organic compounds, such as acetone, in the gas-phase. These materials are designed to change color upon exposure to a particular analyte, which color-change causes a change in thermal energy.

The interactant may also be regenerative. Examples of regenerative interactants may include interactants that are true catalysts. Or, regenerative interactants may be interactants that can be regenerated (after they are consumed or partially consumed) by use of a refilling gas stream. For instance, particularly for living or polymeric interactants, interactants may become more reactive when exposed to water. In such instances, water may be used to regenerate the immobilized analyte interactant after it has been consumed or partially consumed by exposure to the analyte. Referring once more to polymeric interactants, while analyte interactants may be or comprise polymers, they are not limited to them.

The interactant may be immobilized on the sensing junctions directly. If, however, the interactant can cause corrosion or other negative impacts to the thermopile materials which will affect the longevity of the device, other embodiments may be better suited. Preferably, the interactant is immobilized on the side of the substrate opposite the thermopile in such a way that the heat will be transferred preferentially to the sensing junctions. In thin isotropic materials, this is achieved by immobilizing the chemical directly over the sensing junctions.

Optionally, and advantageously, the substrate can be folded so as to allow for creation of a catheter-type device.

Figure 3:
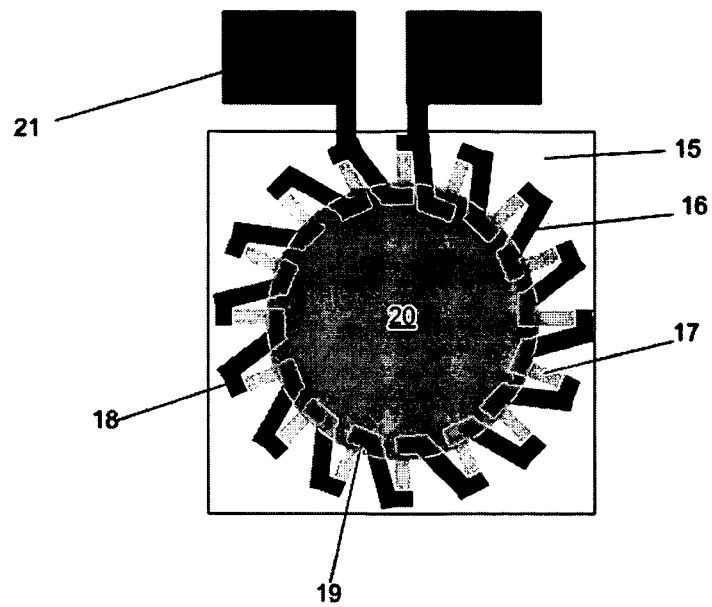
FIG. 3 is a schematic showing a circular thermopile.

The thermopile device configurations shown in FIGS. 1 and 2 are merely illustrative and are not necessarily limiting. FIG. 3, for example, shows a schematic showing a circular thermopile. Thermopile conductors will be deposited onto a substrate 15 on which a first conductor material 16 and a second conductor material 17 are deposited to form reference junctions 18 and sensing junctions 19. The interactant 20 would be deposited proximate to the sensing junctions 19. The voltage can be measured by use of the contact pads 21.

Laboratory prototype thermopiles were constructed with the geometry illustrated in FIG. 2. Bismuth metal was first evaporated onto a polyimide Kapton® thin film substrate through a mask. Once the bismuth deposition was complete, the substrate-mask combination was removed from the metal evaporator. The bismuth mask was removed and an antimony mask clamped to the substrate in such a manner that the antimony deposition would complement the bismuth deposition layer to form the thermopile. Once the antimony deposition was complete, a thin layer of bismuth was deposited on top of the antimony. It has been determined empirically that the thermopile yield is improved significantly. Nevertheless, it must be noted that certain commercially available thermopiles demonstrate less background noise than the prototypes described herein.

To make electrical contact to the thermopile contact pads 12, thin copper wire was attached through the use of a silver bearing epoxy paint.

Figure 4:
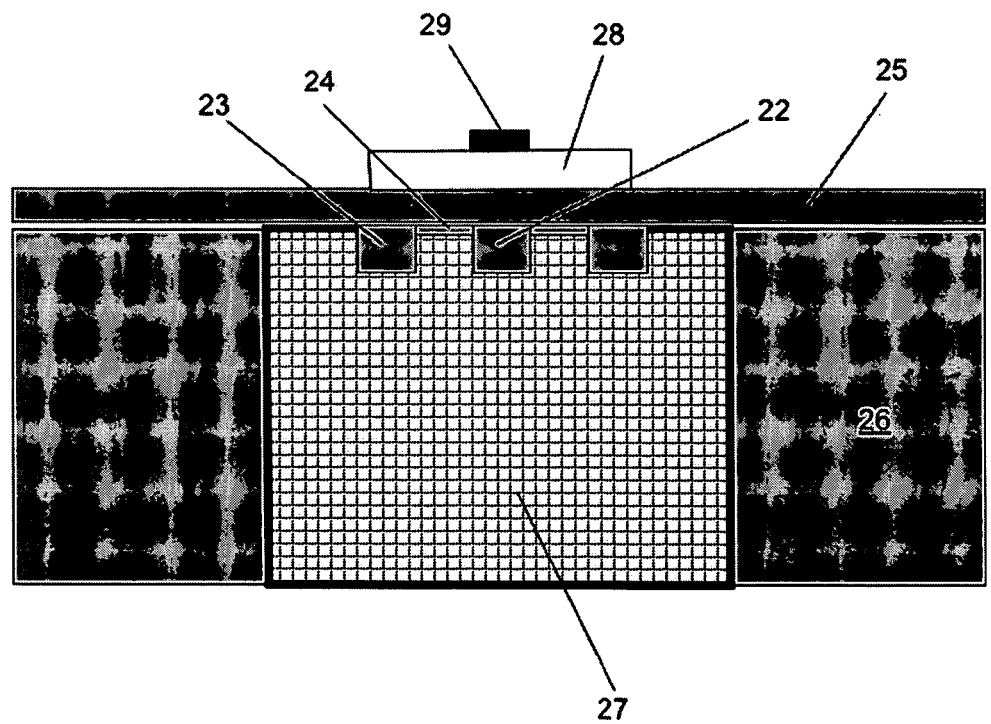
FIG. 4 shows a side cross-section of a thermopile sensor as it was installed in a housing.

FIG. 4 shows a side cross-section of a thermopile sensor as it was installed in a housing. Illustrated are sensing junctions 22, reference junctions 23, and thermopile conductor legs 24 connecting the junctions deposited on deposited on a substrate 25 as described above. For the prototypes, the substrate was placed on a plastic annulus 26 approximately 25 mm in diameter with the metals facing inside the annulus into cylindrical region 27 and the substrate 25 facing the external environment. The cylindrical region 27 was filled with polyurethane insulation. On the other side of the substrate, silicone grease 28 (not shown to scale) was placed such that it covers the area over the entire thermopile. An interactant 29 was placed over the sensing junctions 22 of the thermopile. The copper wires (not shown) protruded from beneath the substrate 25. The advantage of this approach is that the metal of the thermopile are not exposed to the external environment, but the thermal path to the interactant 29 is longer.

Figure 5:
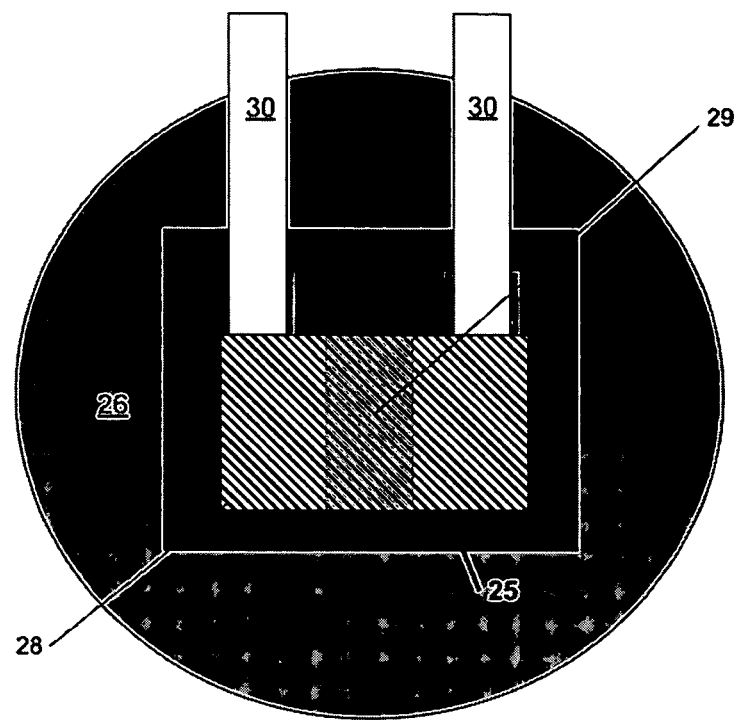
FIG. 5 illustrates the top view of the sensor illustrated in FIG. 4.

FIG. 5 illustrates the top view of the sensor illustrated in FIG. 4, showing the substrate 25 placed on a plastic annulus 26 with the metals facing the inner cylinder of the annulus. Copper wires 30 are electrically connected to the contact pads of the thermopile. The silicone grease 28 is placed over the entire thermopile and the reactant 29 is placed only over the sensing junctions.

For this type of sensor, the ideal chemical reactant is regenerative (not consumed), highly selective to the analyte of interest, and non-toxic, has a long shelf life, and engages in a highly exothermic or endothermic reaction with the analyte or analytes.

This setup has been tested with sodium hypochlorite, hypochlorous acid, and trichloroisocyanuric acid. In this case, the chemical reactants are not in direct contact with the thermopile metals 14. Rather, the chemicals are immobilized on the substrate 13 opposite the thermopile metals 14. The disadvantage of this configuration is that heat must be transferred through the substrate. However, the substrate is extremely thin and therefore the resistance to heat transfer is low. The advantage is that there is no effect of the interactant on the thermopile and also the interactant can be removed and replaced without impact to the thermopile.

Referring also to FIG. 2, the area of the substrate 13 surface that was vertically above the entire surface of the thermopile was coated with silicone vacuum grease to keep the thermal load on both the reference and sensing junctions approximately constant thereby allowing the time constant of the two sets of junctions to be equal. Initially, double-stick cellulose acetate tape was utilized instead of the silicone grease. However, it was determined empirically that acetone reacts with the adhesive portion of the tape, thereby causing a series of competing reactions. A precise volume of trichloroisocyanuric acid was dusted onto the silicone grease over only the portion of the substrate 13 which was vertically above the sensing junctions 10 in precise geometrical fashion by use of a rectangular mask.

Figure 23:
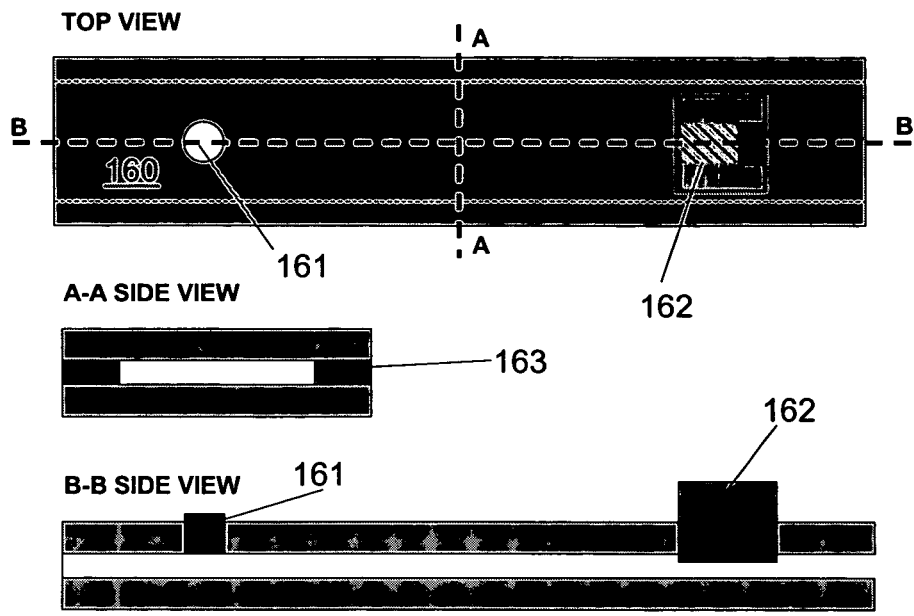
FIG. 23 shows a flow chamber.

Once a thermopile unit is created with the chemical immobilized and wires attached, it should be housed in a device that will allow for an interface with the breath or analyte of interest. In this embodiment, a laminar flow chamber was constructed (generally illustrated in FIG. 23). To decrease the chances of turbulent flow, sharp edges were removed from the system. A rectangular conduit was selected with a top and bottom piece. The height was made extremely small, again to minimize the chances of turbulent flow.

Two circular holes 161 and 162 of different diameters were drilled in the top plate of this conduit 160 through the top. One hole allowed the gas with the analyte to enter the chamber. The second hole tightly fit the thermopile sensing unit with the chemicals facing downward and into the slit. It is believed that this allowed air with the desired analyte to enter the flow chamber through the small hole, achieve fully developed laminar flow through the course of the conduit and interact with the chemical on the downward facing thermopile.

Figure 6:
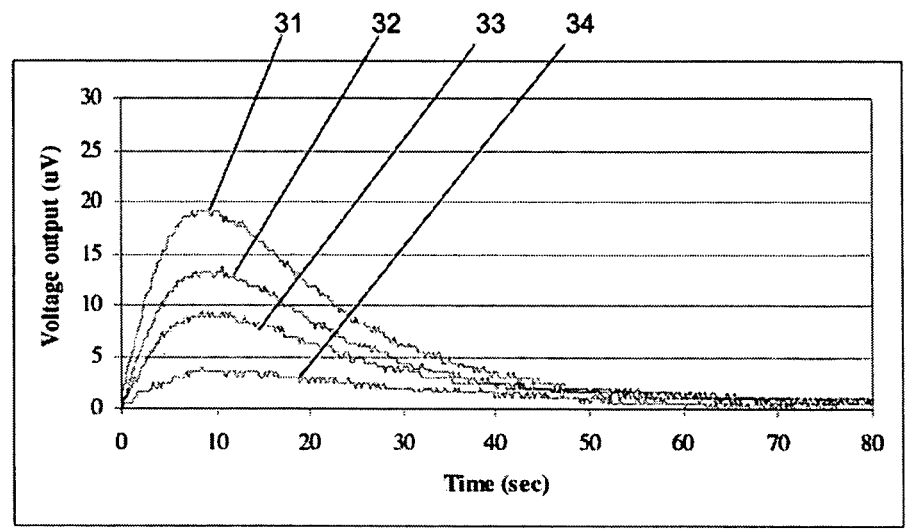
FIG. 6 shows the results of a test of the sensor illustrated in FIGS. 4 and 5 for four analyte concentrations.

FIG. 6 shows the results of a test with acetone in air reacting with a trichloroisocyanuric acid reactant. Curves 31, 32, 33, and 34 show the output voltage (in microvolts) as a function of time (in seconds) for an acetone concentration of 455, 325, 145, and 65 ppm respectively.

Figure 7:
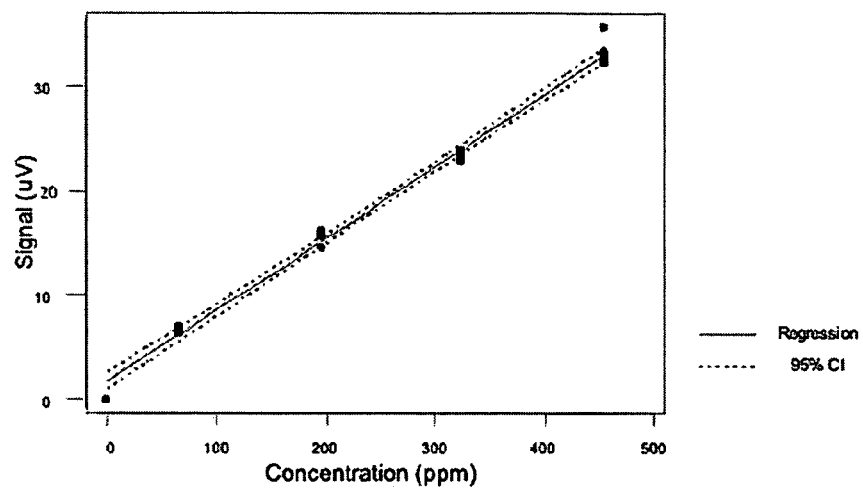
FIG. 7 summarizes sample test results by showing the peak sensor output voltage as a function of analyte concentration.

FIG. 7 shows the result of the same apparatus as a function of acetone concentration in ppm. Pulses of acetone of various concentrations were admitted to the conduit and the signal measured. The aspect of the raw data shown as the signal in FIG. 7 is the peak voltage output measured by the sensor. As may be seen, there is a very strong correlation between signal voltage and concentration. Thus, making a calibrated system should be quite practical.

Figure 8:
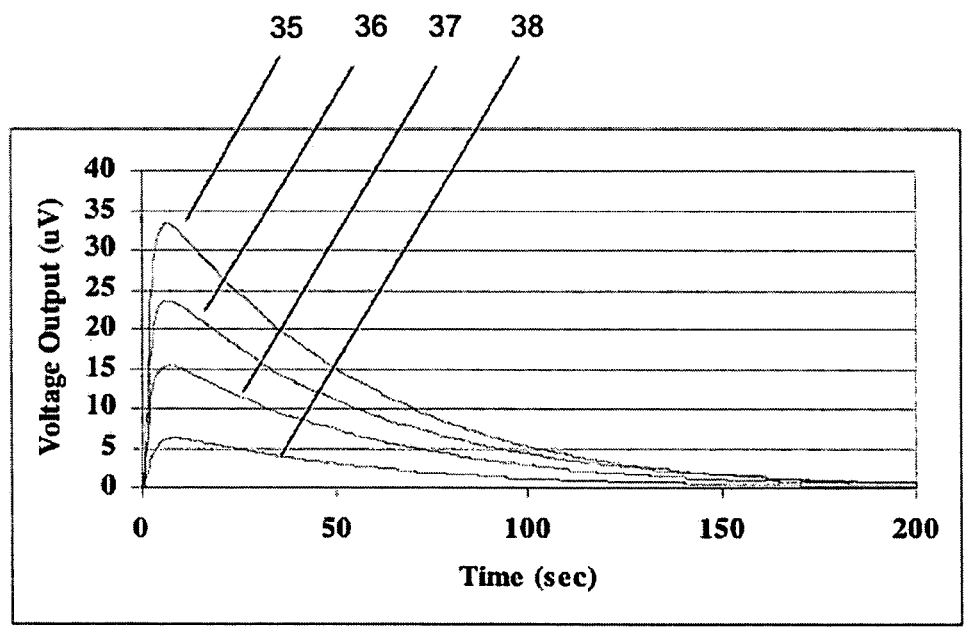
FIG. 8 shows theoretical curves for the same sensor and analyte concentrations as show in FIG. 6.

FIG. 8 shows theoretical curves generated by a mathematical model for the same sensor and analyte concentrations as show in FIG. 6. Similarly, curves 35, 36, 37, and 38 show the output voltage (in microvolts) as function of time for an acetone concentration of 455, 325, 145, and 65 ppm respectively.

This example discusses the sensor setup for the case when the analyte is brought into contact with the thermopile sensor principally via diffusion. In other words, the thermopile sensing unit would operate in a stagnant or low flow environment.

A large glass Petri dish was used to simulate this system. The thermopile was mounted as described herein above. This unit was adhered centrally to the base of the Petri dish. The electrical leads from the thermopile were vertically suspended. The top of the Petri dish was covered rigorously with two pieces of Parafilm®, allowing the leads to exit the dish. (Parafilm® is a flexible film commonly used for sealing or protecting items such as flasks, trays, etc. and is a product of the American Can Company.) This setup was immobilized.

Instead of introducing acetone by creating flow over the thermopile, liquid acetone was injected into the Petri dish. Thus, acetone was allowed to evaporate into the ambient above the dish. Once acetone molecules were in the vapor phase, they diffuse to the surface of the thermopile and begin to interact. This setup was tested with hypochlorous acid, sodium hypochlorite, trichloroisocyanuric acid, and sodium dichloroisocyanurate dihydrate.

Figure 9:
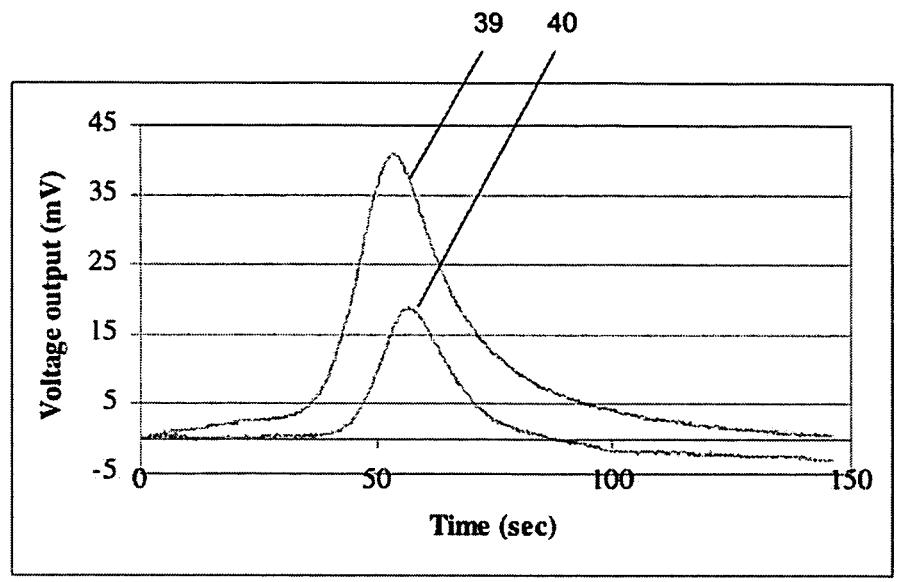
FIG. 9 shows the sensor response to analyte that was transferred only by diffusion.

FIG. 9 shows the experimental results generated by this embodiment. As shown, curve 40 has half the acetone concentration as curve 39. The acetone concentrations may be high for physiological applications. However, the significance is that the sensor is capable of measuring analytes that are transferred to the sensor by diffusion only. While it may appear that the process is slow due to the peak at 50 seconds, it is important to note that the analyte, in this case acetone, was injected in liquid form and had to evaporate and then diffuse to the surface of the device prior to any possible reaction.

Figure 10:
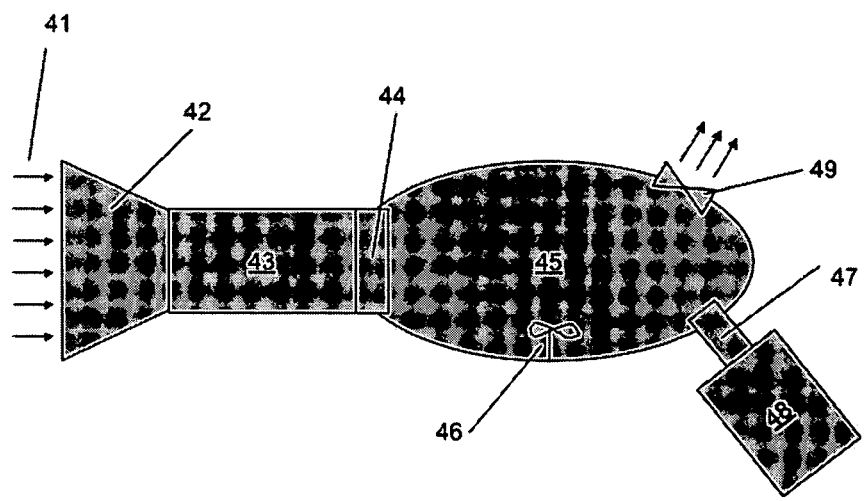
FIG. 10 shows a possible embodiment for use in a hospital environment using a patient gas mask.

FIG. 10 shows a possible embodiment for use in a hospital environment using a patient gas mask. Expired air 41 is generated either from the oral or nasal cavities. The breath is captured by a face mask 42 (which may be of standard gas mask design or some other) and is then directed through a polyethylene tube 43 where it is then filtered by a particle filter 44. The breath is directed by the tubing to a distendable volume 45 that is well-stirred by fan or other method 46. The flow of the breath through a channel 47 that leads to a chamber 48 containing the sensor can be controlled by a valve 49 that leads to the ambient environment.

The distendable volume 45 would allow for well-mixed fluid to enter the channel 47 in a regulated, laminar flow manner. As a result, variations in patient breath such as flow velocity patterns, interfering substances, temperature gradients, and particulate matter would be controlled, normalized, and mixed prior to introduction to the sensor inside chamber 48. This is useful, for instance, because the first volume of expired air is non-physiologically active (i.e. lung dead space).

The filter 44 is used because it may also be desirable to filter the breath before it enters volume 45. Different types of filters may be employed. First, a particle filter can be used. There are, of course, varying levels of particle size, shape, and type that can be considered. A simple particle filter, primarily to remove food residue, should suffice. Second, there are many filters which remove moisture from the breath. For instance, the entering breath can be directed to a channel wherein a water absorbent such as silica gel is immobilized and which will absorb all of the water. As may be appreciated, this may or may not be desirable depending on whether water is needed for the chemical reaction.

In this environment, the sensor could be used for continuous monitoring of patients. Suitable, well known, electronics could be used to communicate with nurses' stations, hospital computers or set of local alarms.

A very important analyte is ammonia. Breath ammonia is found in elevated concentration in patients with renal or liver failure. If ammonia were the analyte in the gas, ammonia can react with many different substances. As an example, ammonia reacts with hydrochloric acid to form ammonium chloride. The ammonium chloride will subsequently react with barium hydroxide to form barium chloride, ammonia, and water. This will allow for a two-step reaction sequence thereby increasing the total enthalpy of the reaction producing an amplification of the enthalpy.

It is important to note that this device can be used to measure the concentration of multiple analytes simultaneously. Thus, by use of multiple thermopiles, an entire screening can be performed with one breath.

Figure 11:
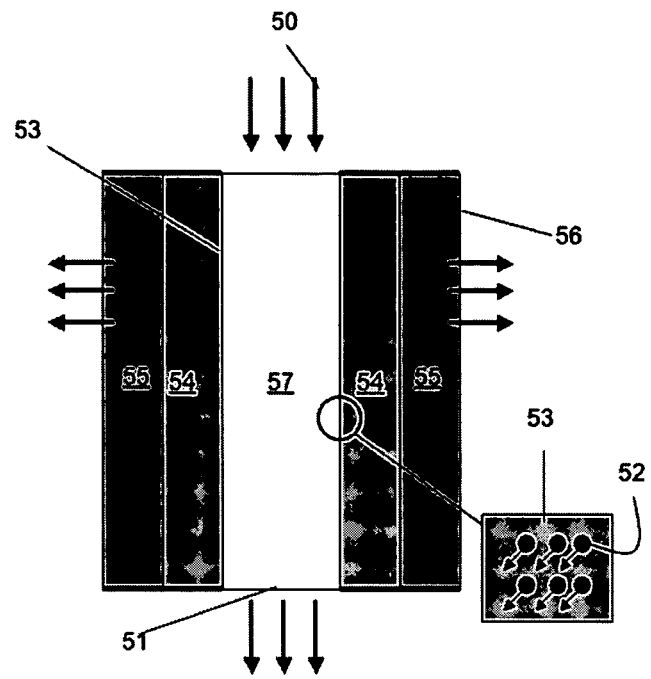
FIG. 11 shows a first possible chemical immobilization technique for chemical amplification.
Figure 13:
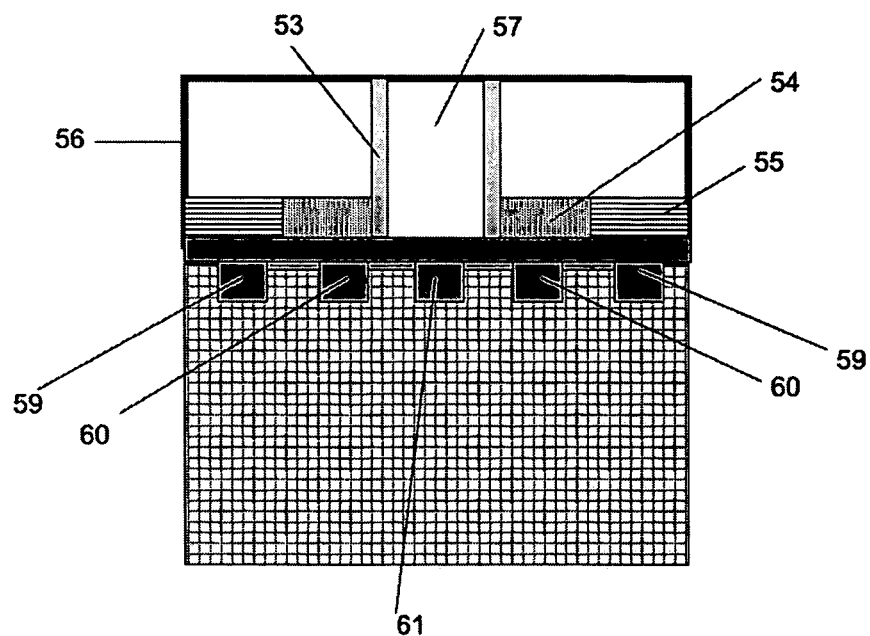
FIG. 13 depicts a side view of the technique shown in FIG. 11 and FIG. 12.

FIG. 11 shows a first possible chemical immobilization technique for chemical amplification. The gas containing the analyte 50 enters the conduit 57. Some of the gas exits at the end of the conduit. However, some of the gas passes through the pores 52 of the channel wall 53. Next to the channel wall, one interactant 54 is located and then a second interactant 55. This gas leaves the conduit through the outer semi-permeable conduit walls 56. Referring to FIG. 13, the thermopile consists of reference junctions 61 and sensing junctions 59 and 60. The sensing junctions can be single or multiple sets, depending upon the physical size of the junctions.

Figure 12:
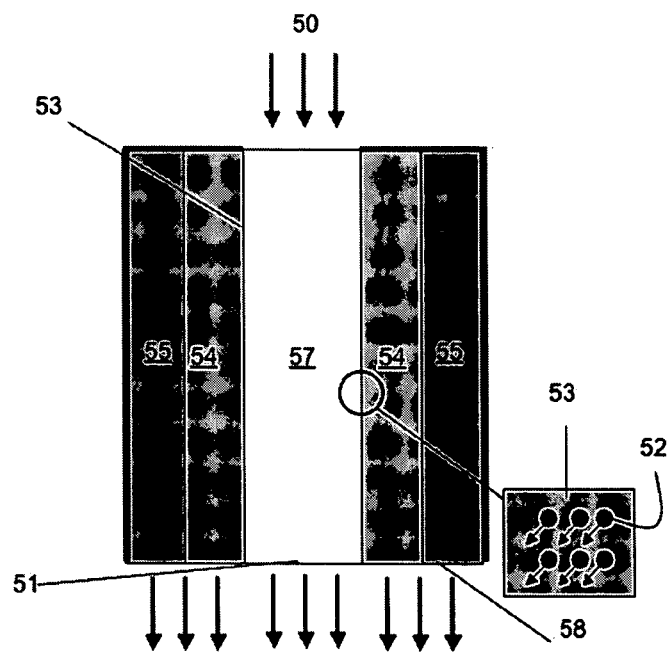
FIG. 12 shows a second possible chemical immobilization technique for chemical amplification.

FIG. 12 shows a second possible method of immobilizing the chemical. In this case, the wall 56 is impermeable and all gases flow through the conduits.

Figure 14:
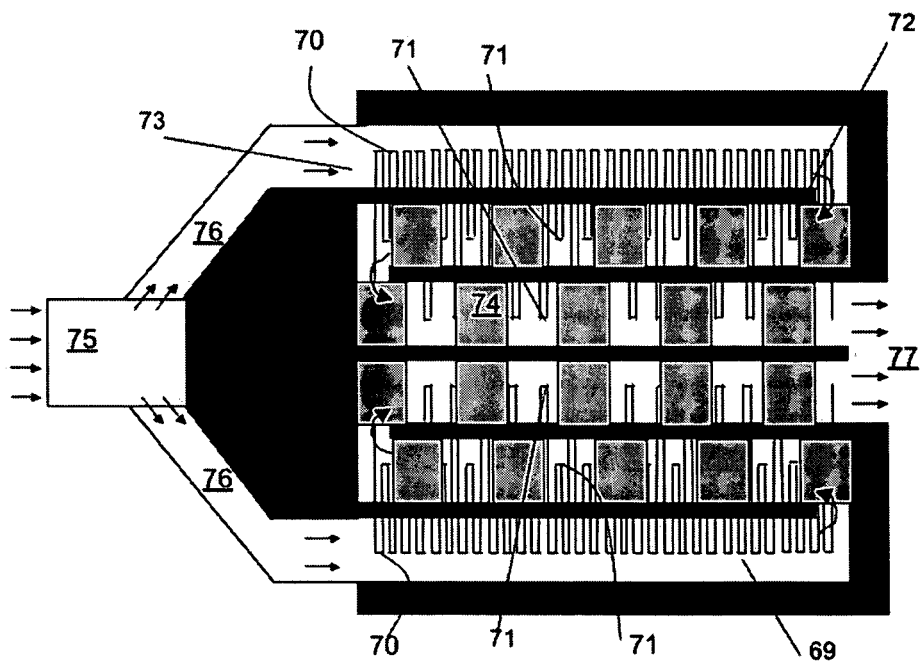
FIG. 14 shows the top view of a possible embodiment of an optimized chemical sensor.
Figure 15:
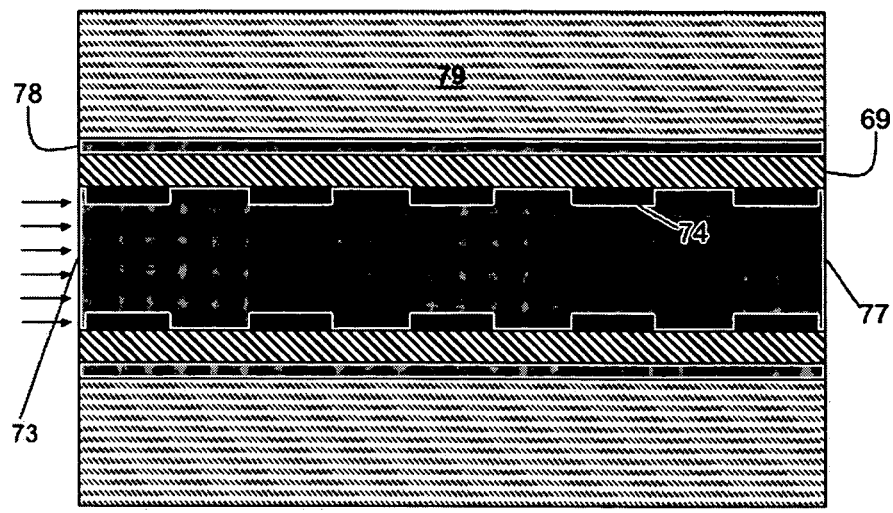
FIG. 15 depicts the side view of a possible embodiment of an optimized chemical sensor.

Reference will now be made to FIGS. 14 and 15. In operation, the fluid 75 enters the conduit through a mouthpiece. The fluid flow 75 is then divided between two tubes 76 both of which direct the fluid 75 into the reaction chamber, which is insulated. The fluid 75 first passes across a set of reference junctions 70. Then, the fluid 75 changes direction and begins to pass over the first set of sensing junctions 71 of the thermopile. The sensing junctions 71 are each coated with interactant 74. However, the sensing junctions 71 are separated from one another by the legs of the thermocouple, with further sensing junctions 71 in a subsequent channel. Therefore, the fluid 75 passes over a section of interactant 74 and then a section where interactant 74 is absent. Once again, the fluid 75 changes direction and passes over a second set of sensing junctions 71, which are distributed in the same way as described earlier. Finally, the fluid 75 exits the chamber at the opening 77 at the back-end.

FIG. 15 shows a cross section having the structure of FIG. 14. Interactant 74 is deposited on thin film substrate 69 on which is deposited sensor thermopile material 78. The device is surrounded by a thermal insulating structure 79. Fluid flow 73 carries the analyte past the interactants 74. As analyte is taken up by the interactant, its concentration drops in the layers next to the top and bottom. Diffusion from the center acts to replenish the depletion, but, depending on the reaction kinetics, chemistry mechanisms, flow regime, etc. this may not be enough to compensate. After passing the interactants 74, the concentration next to the top and bottom is not depleted, but is replenished by diffusion from the mid part of the flow. Based on theoretical considerations and considerations such as those described herein, the rate of uptake at a subsequent downstream interactant will be higher than if there were no replenishment zone. Thus, the uptake process is more efficient. Less total interactant in the device can be used for the same overall uptake of analyte.

The dimensions for this embodiment are provided. These dimensions, however, are merely illustrative of this particular embodiment. The mouthpiece should have dimensions of approximately 0.0212 m, the reaction chamber will be a conduit with a square-shaped cross-section of dimensions 0.0762×0.0762 $m^2$. Each channel is 0.0106 m wide and the channel barriers are 0.00254 m each. There are six channels and five channel barriers. The chemical (analyte interactant) is immobilized for lengths of 0.001 m with gaps between chemical of 0.001 m distance. The chemical is immobilized with appropriate particle size to engage in a reaction with a thickness of about 0.001 m. The channel height is 0.0206 m. The thickness of the thermopile metals can vary, but as in the previous examples, the metals are approximately 3 μm thick and the Kapton substrate is approximately 50 μm.

Compared with the chemistry and analyte of the working prototype with illustrative output as shown in FIG. 6, this device is expected to increase the signal generated by a factor of approximately 100 times at least.

Use of channel separators over the thermopile itself may be useful in nanotechnology or microfluidics applications. Certain embodiments lend themselves well to miniaturizing the device by miniaturizing the sensor. In other embodiments, however, it may be desirable to miniaturize the channels through which the analyte flows but maintain the sensor in a current physical size. FIG. 14 shows one embodiment that employs channel separators 72.

As illustrated, the replenishment zone relies on diffusion from the bulk stream. However, the replenishment of the outer layers could be augmented by providing mixing. This happens to some extend as the fluid makes a turn in the serpentine path in FIG. 14. Also, obstructions could be placed in the center of the conduit after each interaction zone. They could, for example, be round wires stretched across the center of the conduit. Small flat plates may create more turbulence and better mixing.

In addition to passive measure, one could use mechanical agitation. This could be provided with piezoelectric elements or by shaking the entire device.

The surface concentration of the analyte is generally limited by the input concentration of analyte (while this is generally true, there may be instances where this may not be the case). Thus the surface concentration of analyte can vary from zero to the input concentration. The flux to the surface, however, tends to decrease as a function of distance along the surface unless the interaction region is interrupted. Theoretically, if the interaction regions are made vanishingly small and large in number, such an embodiment uses the least amount or interactant for any given signal. Normally, it is not necessary to react all of the analyte, just enough to get a strong signal.

This use of one or more replenish zone between interactant zones (a.k.a. interrupters to the concentration boundary layer) has quite general utility. Dilute solutions of almost all analytes in almost all fluids and/or gases will diffuse based on a concentration gradient. As such, embodiments and methods involving the replenish zone can be applied to fluids broadly, which includes not only gases but liquids as well. For example, a thermopile coated with an interactant (e.g. an enzyme) that is patterned using the replenish zone may operate in the blood stream, cell culture media, or water treatment plants.

Furthermore, the use of one or more replenish zones between interactant zones may be applied broadly to embodiments which employ different sensors and/or sensing methods. Most sensors operate based on the interaction of the analyte with an analyte interactant. As discussed herein, the amount of "reaction" that takes place may be enhanced by certain modes of patterning the interactant, such as the use of a replenishment zone. Thus, any sensor or combination of sensors that quantify the amount of analyte present in a fluid (e.g. liquid, gas, etc) may benefit from the use of a replenishment zone. For example, if the reaction between the one or more analyte and with the one or more analyte interactants produces heat, then a thermal sensor such as a thermopile, pyroelectric device, or a thermistor may be well suited for the application. However, the use of a replenish zone is not limited to heat measurement. Other outputs of reactions that produce a reaction that can be sensed would benefit from this design. For instance, if the reaction produces electromagnetic radiation (e.g., light, infrared radiation), a remote sensor (e.g. a camera, IR detector, etc) could be used.

Figure 37:
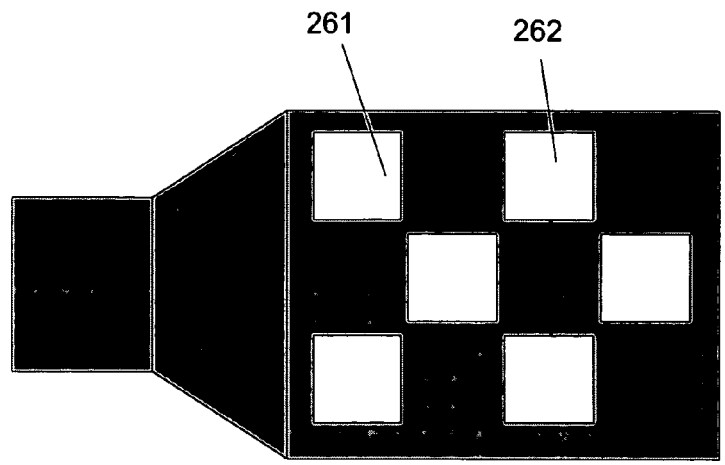
FIG. 37 is an embodiment of the invention that utilizes one or more sensors.

Referring now to FIG. 37, the sensors 261 and 262 that employ replenish zones or use the concentration boundary layer interruption methods are not limited to thermopiles or thermocouples. Examples of sensors comprise one or more of the following: thermistor, thermocouple, pyroelectric, thermopile, ion sensor, radiation sensor, electrochemical sensor, piezoelectric sensor, optical sensor, etc. Sensor 261 may be or comprise an electrochemical sensor. Sensor 262 may be or comprise a thermopile in one application and a piezoelectric sensor in a different application. In this manner, the specificity and sensitivity of the overall device may be improved.

There are other ways by which the specificity and/or sensitivity of thermal sensors can be enhanced. One approach is to increase the amount of heat that is produced either for a particular binding event or at any point in time.

Figure 50:
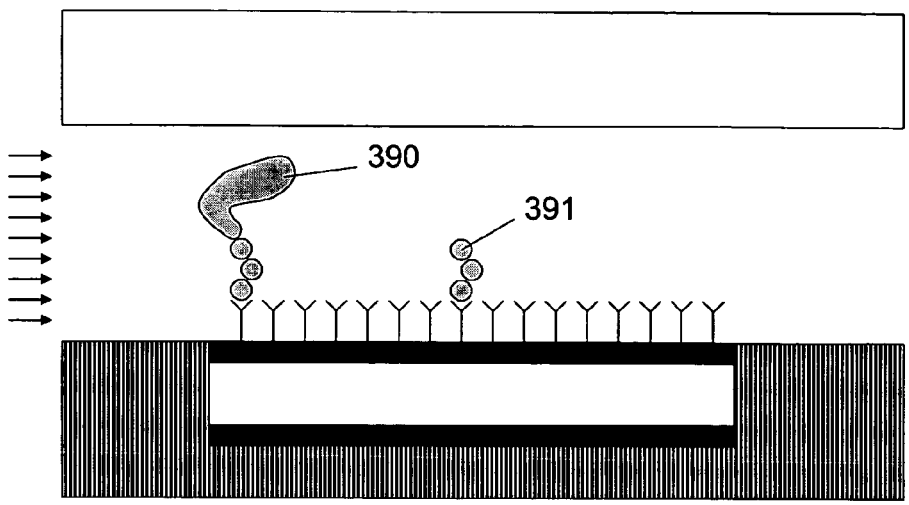
FIG. 50 is an embodiment that utilizes mass discrimination principles.

Most pyroelectric materials are also piezoelectric in nature. Therefore, it is possible to combine these two methods of detection into one sensing unit. This may enhance the specificity/selectivity of the sensor. This is particularly relevant if the analyte is a biological material (e.g., glycoproteins, cell receptors, etc) that is being detected from a body fluid (e.g. blood, spinal fluid, synovial fluid, urine, etc). For instance, if one is attempting to detect glycoproteins via the sugar moiety, it may be necessary to discriminate between sugar moieties that are actually bound to the protein versus free flowing sugar moieties. In this instance, a mass transducer, such as a piezoelectric sensor, may be used to discriminate based on the mass of the binding agent. This is exemplified in FIG. 50 where 390 is a glycoprotein and 391 is a free flowing sugar moiety.

Another way to increase the specificity of the thermal sensor is by using a multiple-binding event. Basically, the analyte is confirmed if two binding events take place. These binding events could be detected by two different sensors (e.g., both or nothing) or by the same sensor (e.g. increased heat). The use of the second binding site may be helpful in discriminating between same-species interfering substances.

Figure 51:
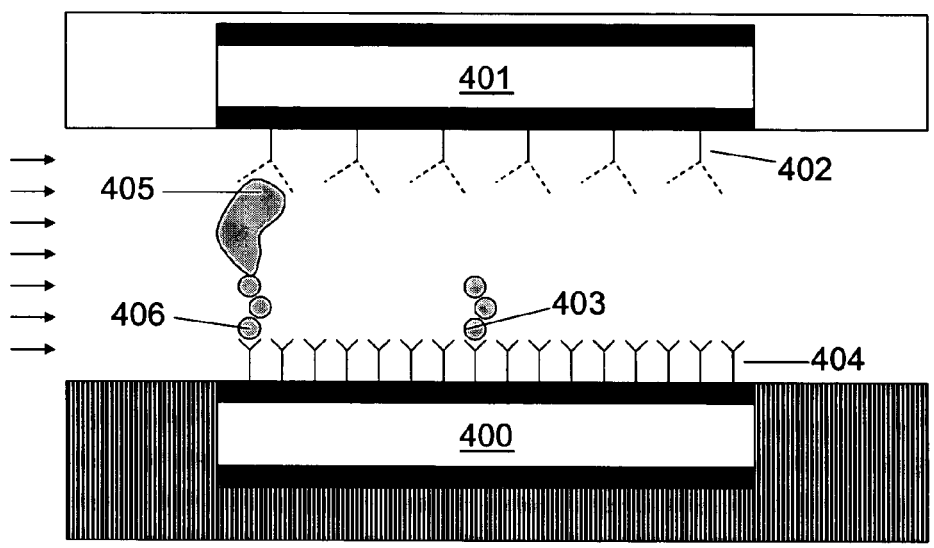
FIG. 51 is an embodiment with two sensors for enhanced specificity.

FIG. 51 shows an embodiment in which at least two thermal sensors (400 and 401) are used. In this embodiment, there are two analyte interactants (402 and 404). Two analytes are shown in the figure. The first analyte has the two binding sites (405 and 406) necessary for interaction with the two analyte interactants (402 and 404). The second analyte has only one 403 of the binding sites. In this embodiment, the sensors 401 and 402 can discriminate between the first analyte and the second analyte, which may be important if one of them is an interfering substance.

Figure 52:
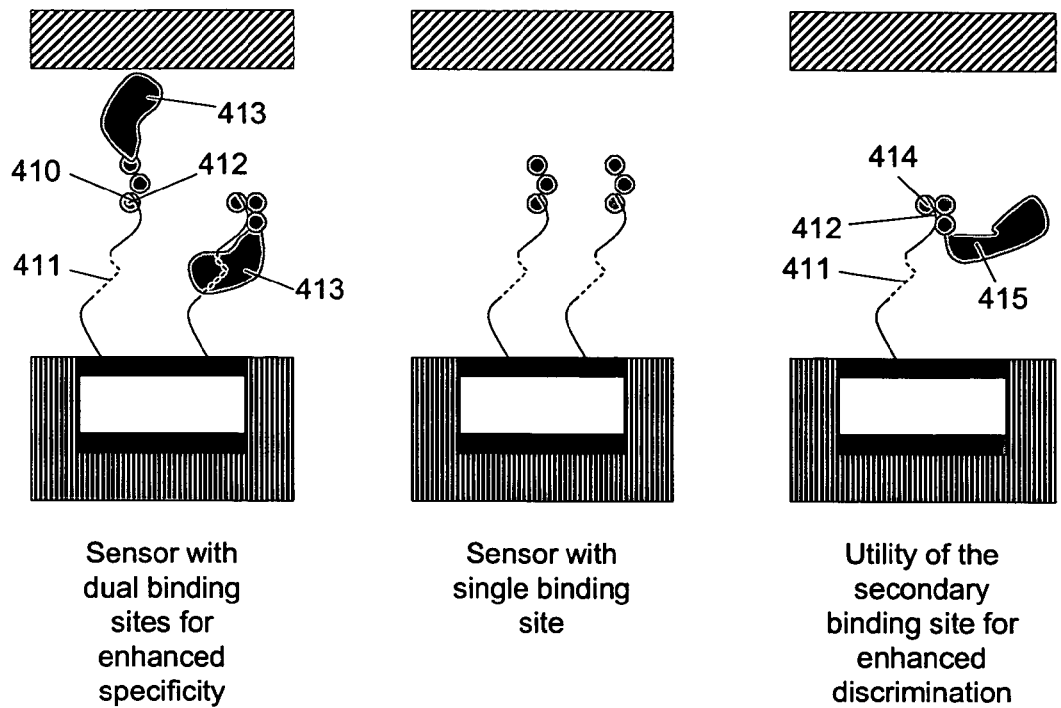
FIG. 52 is an embodiment with multiple binding sites.

FIG. 52 shows an embodiment in which two binding sites are used to discriminate between different chemicals/molecules (the second binding site is designated by a dashed line). The analyte interactant has two different interactant binding sites (410 and 411). The analyte may be or comprise a molecule with different functional groups or analyte binding sites. One of the analyte binding sites 412 binds with the interactant binding site 410. The second analyte binding site 413 binds with the second interactant binding site 411. A potential interfering substance also has two binding sites 414 and 415. While one of the interfering substance's binding sites 414 does bind to one of the interactant binding sites 412, the second of the interfering substance's binding sites 415 does not bind to the second interactant binding site 411.

Figure 53:
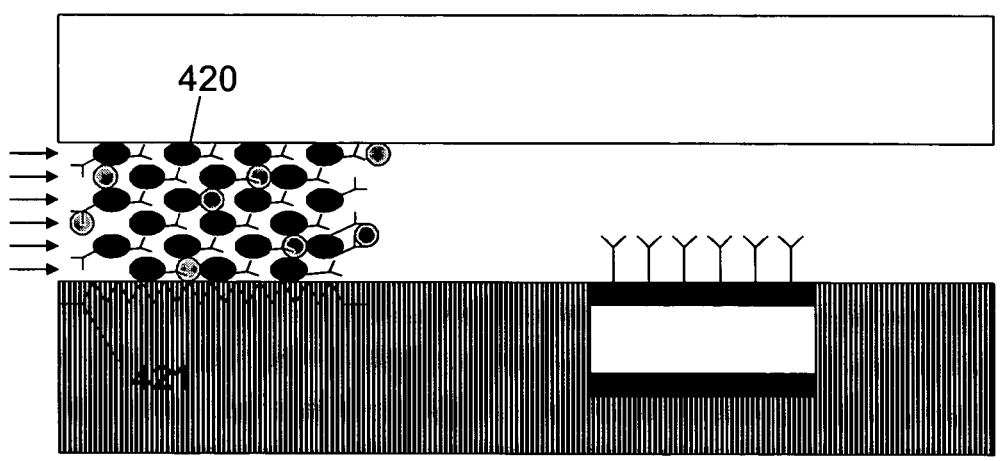
FIG. 53 is an embodiment that utilizes a concentrator.

An embodiment that aids in increasing sensitivity is shown in FIG. 53. In this embodiment, a "concentrator" is used. This concentrator 420 is designed to capture all of the analyte (e.g. activated carbon may be used to capture volatile organic compounds). Once the analyte is captured, it is "flushed out" from the concentrator via some mechanism such as a heater 421. In this way, the concentration of analyte in the "flushed" fluid is greater.

Chemical reactions in the liquid phase are generally better studied than those in the vapor phase. In aqueous solutions, hydrogen and hydroxide ions are often involved in acid or base-catalyzed reactions. One possible embodiment of the invention shown in FIG. 16 provides an apparatus and method by which the analyte in the gas may be condensed to liquid form.

Figure 16:
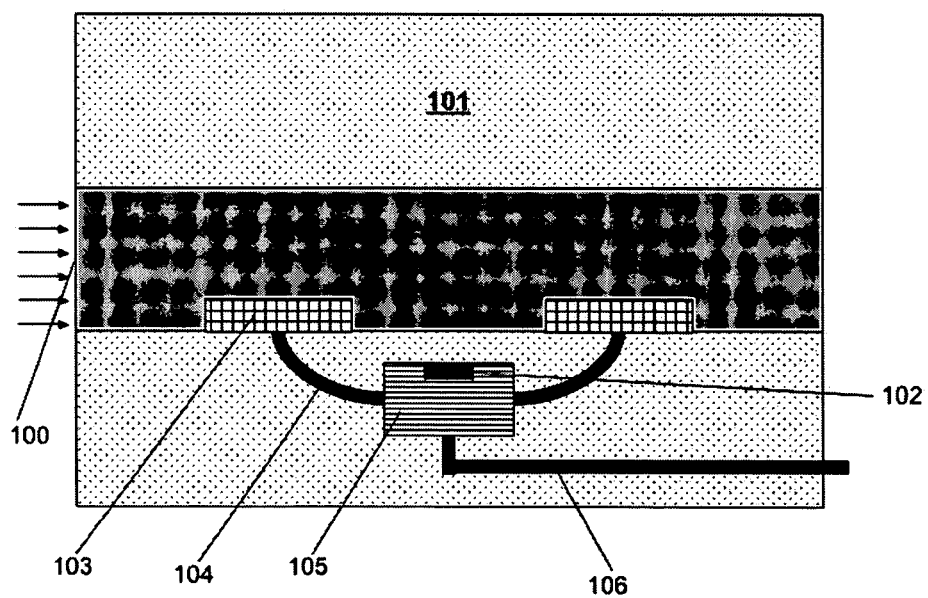
FIG. 16 shows a embodiment of a gas sensor using a condenser.

The sensor shown in FIG. 16 is designed to condense a gas to a liquid. In this embodiment, in medical applications, the breath would condense prior to exposure to the sensor. This embodiment takes advantage of the improved diffusivity of analytes in a gas as compared to in a liquid. Simultaneously, the heat loss in a liquid is far less than in a gas under similar physical conditions. This design also allows one to take advantage of the well-researched liquid-phase acetone reactions.

One of the problems that frequently arises with chemical sensors is chemical depletion. In other words, the chemical reactant is consumed over a period of time. One way to circumvent this problem is to use chemistries that have a long lifetime and/or are not consumed in the reaction (enzymes or catalysts). However, even if an enzyme is used instead of an inorganic chemical, enzyme deactivation or degradation remains a problem. Here two embodiments of the present invention are presented which specifically address the aforementioned problem.

Figure 17:
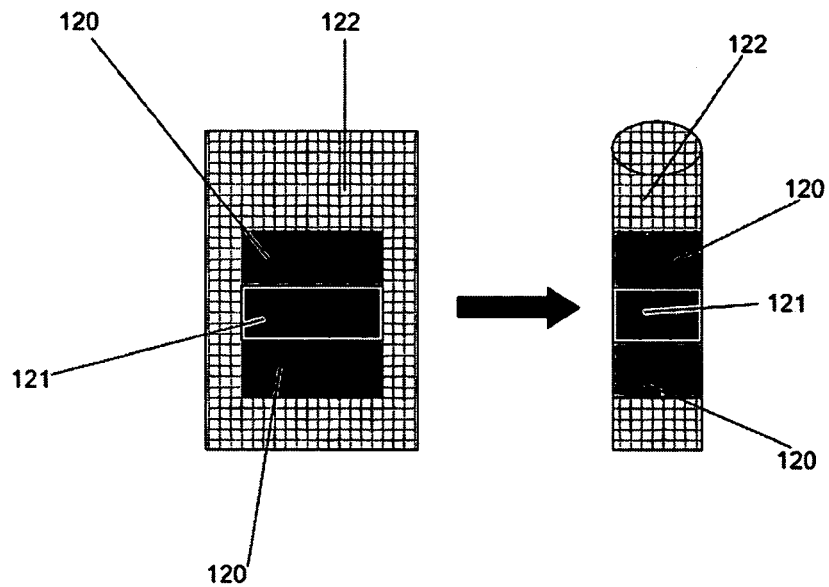
FIG. 17 depicts a method for creating a thermopile in a catheter style.

In one embodiment, the sensor is made "removable" from the overall breath collection chamber. This is done by fashioning the sensor as a probe or by fashioning the substrate such that it takes on a three-dimensional shape, for instance, of a catheter. FIG. 17 shows the thermopile where the sensing junctions are positioned in one area 120 and the reference junctions in another area 121. The substrate 122 is folded to form a cylindrical tube. If the substrate on which the thermopile is deposited is flexible, then the thermopile itself can be formed around, for example, a cylindrical insulator. In this way, the thermopile can be made into a catheter-style device.

Figure 18:
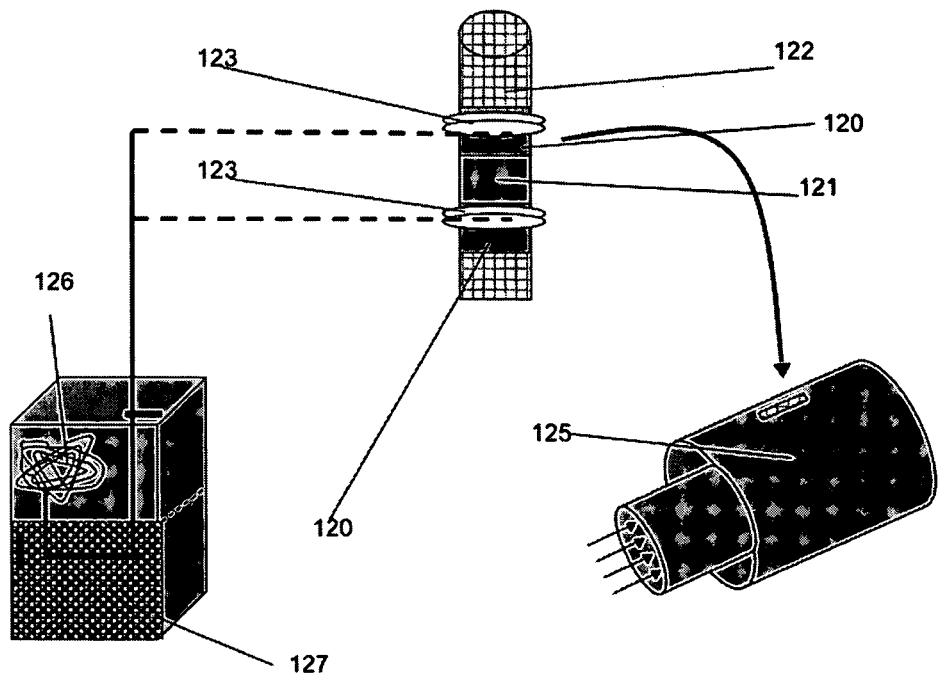
FIG. 18 shows a method for immobilizing chemical on the sensor described by FIG. 17.

In another embodiment, a thin absorbent material exposed to some interactant, for example hypochlorous acid, is wrapped around the sensing junctions of the thermopile. Optionally, the reference junctions may be wrapped with a non-exposed absorbent material. FIG. 18 shows a possible method by which chemical can be immobilized on the thermopile in, for example, the embodiment described in FIG. 17. A material 126 is exposed to a chemical interactant 127 and the interactant-coated threading material 123 is wrapped around the sensing junctions 120 and the reference junctions are either coated with unexposed material 126 or left uncoated. In another embodiment, the entire thermopile with material is placed in a chamber 125 wherein the analyte interacts with it.

Thermal sensors according to these aspects of the invention and as generally described herein can be designed, configured and used to measure the concentration of multiple analytes, preferably simultaneously. Thus, for example, by use of multiple thermopiles or pyroelectric sensors, an entire screening can be performed with one breath.

More than one interaction can also occur simultaneously or sequentially. This can occur if multiple interactants are immobilized on the sensing portion of the device. Alternatively, the product or intermediary, etc. of a first reaction may initiate a set of secondary reactions, which may or may not involve the analyte. In any case, the net enthalpy of these interactions dictates the response of the device. A non-zero net enthalpy causes a temperature change on the sensing junctions relative to the reference junctions, which temperature change can be quantified by measuring the output voltage.

Even if only one interaction occurs, the chemistry may be selected such that the products of the initial reaction act as reactants during secondary interactions with the analyte or other substances which can amplify temperature changes.

In other cases, measuring multiple analytes may be desirable. In the presently preferred embodiments, each thermopile within the array may be coated with a different material such that selectivity of several analytes is determined by the different interactions. The response of the individual thermopiles is determined by the individual thermopile voltage response which creates an overall profile. This profile or pattern will be characteristic of a specific analyte or analytes of similar chemical family and can therefore be used to identify at least one analyte. This can be adapted to pyroelectric sensors as well.

Thus, a single analyte interactant may be used to sense one or more analytes. This may be useful when a single analyte interactant senses a class of analytes. Or, multiple analyte interactants can be used to sense a single analyte very specifically. Or, multiple analyte interactants can be used to sense multiple analytes (e.g., for screening purposes).

Figure 21:
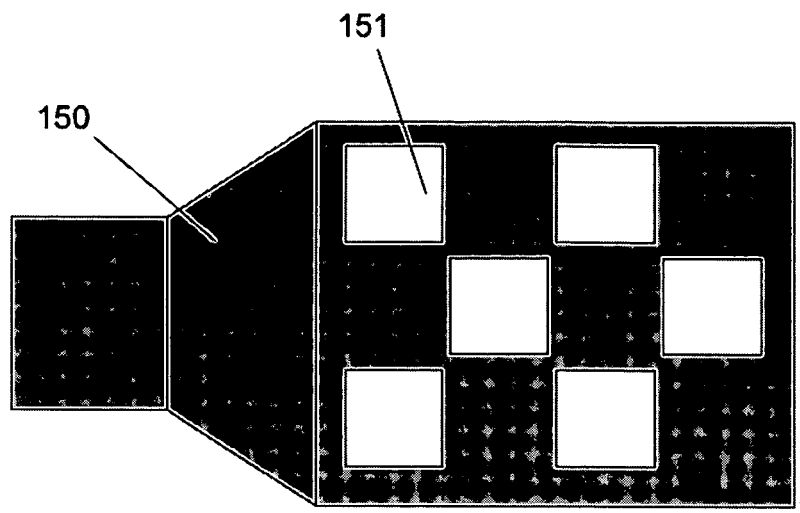
FIG. 21 shows a layout of a device using multiple thermopiles.
Figure 22:
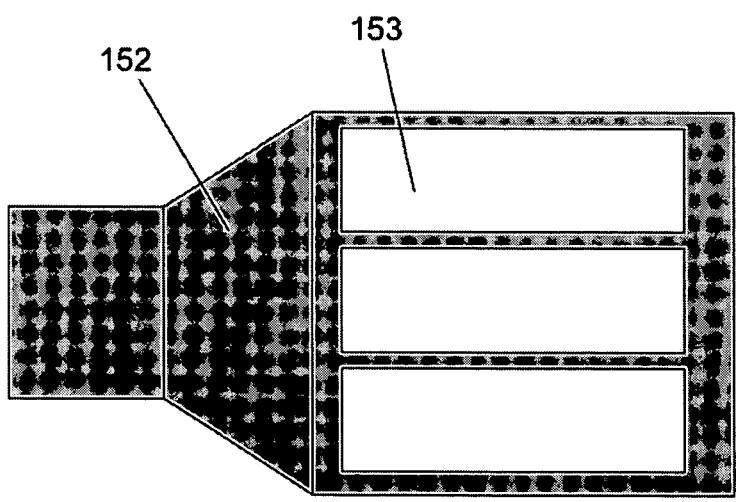
FIG. 22 shows a layout of a device using multiple thermopiles.

If multiple devices are used either to more selectively identify the analyte or to reduce the error of a single device, then there are some geometry considerations that may be important. For instance, the devices could all be placed side by side as close to the leading edge as possible. FIG. 22 shows a possible embodiment of a device 152 containing multiple sensors 153 where the sensors are placed side by side close to the leading edge of the device. If this is not possible or desirable under the circumstances, then the devices could be placed with gaps between them. The exact geometry can vary from one setup to the next. One may place the devices in a chess-board like pattern because the formation of the boundary layer is streamline-specific. FIG. 21 shows another setup of a device 150 where multiple sensors 151 are placed in a chess-board like fashion.

For most applications, it is desirable to minimize the time required to determine the concentration of the analyte. In some instances, this is motivated because the analyte of interest is of critical importance to patient care. In other instances, for example in breath analysis, the user can only breathe into the device for a finite period of time.

Additionally, under most circumstances, the analyte in the gas stream is the limiting reagent in the chemical reaction or enthalpic process. Therefore, given the limited availability of the analyte (both in terms of time and concentration), it is often desirable to maximize the amount of analyte that is involved in the enthalpic process and therefore available to generate or consume heat.

To maximize the surface analyte concentration, various parameters of the system must be optimized. The following provides a method for doing this.

First, one defines the physical setup and environment in which the sensor might be working. Typical considerations include the geometry (e.g., flat plate, rectangular slit, conduit), nature of the flow environment (e.g., highly controlled or unpredictable), and physical properties (e.g., diffusivity, heat transfer coefficient, reaction enthalpies).

Second, the surface flux of the analyte is determined. The chemical kinetics, flow regime, and various physical properties preferably are considered for this analysis. The nature of the flow is particularly important and can vary depending on the sensor design and geometry layout (e.g., straight or coiled flow path). Depending on the geometry, the entire length of the sensor may be exposed to the analyte during the time period designated for analysis. In other instances, however, such as pulsatile flow, certain parts of the sensor may be exposed to a bolus of fluid, which would create a time-varying flux.

Third, the surface analyte flux is maximized by selecting or optimizing parameters of the system. As with any optimization exercise, engineering tradeoffs must be made. For example, we may optimize the chemical patterning and balance the sensor placement with the conduit height.

This method can be employed in a wide variety of applications. A particular example is presented below to illustrate.

Step 1: Define Physical Setup and Environment in which the Sensor is Working

In this embodiment, the sensor is part of a rectangular hand-held acetone-measuring device that is intended for consumer use. The geometry of the device is generally described by FIG. 14. Because it is a hand-held device, the length and width are specified as 3" in dimension. There will be 5 channel separators and 6 channels, as shown in FIG. 14. The flow rate is likely to be variable with time and therefore the implications need to be studied. It is desirable to maximize the flux of acetone to the surface of the thermopile sensor where acetone engages in an assumed instantaneous reaction with an immobilized chemical.

The following dimensions are arbitrarily chosen (here, the term "arbitrary" indicates that the dimensions are not defined by mathematical computations, but rather by other factors such as human factors engineering, compatibility with standard connection pieces, etc). The mouthpiece has a diameter of approximately 0.0212 m, the reaction chamber will be a conduit with a square-shaped cross-section of dimensions $0.0762 \times 0.0762$ m$^2$. There are six channels and five channel barriers. Each channel is 0.0106 m wide and the channel barriers are 0.00254 m each. The thickness of the thermopile metals can vary, but as in the previous examples, the metals are approximately 3 µm thick and the Kapton substrate is approximately 50 µm.

Because acetone levels of physiological importance are extremely low concentrations, the physical properties of the acetone-air mixture are assumed to be equal to those of air and are further assumed constant: the kinematic viscosity, $v$, is $v = 1.69 \cdot 10^{-5}$ m$^2$/s, and the diffusivity of acetone in air, D, is $D = 8.5 \cdot 10^{-6}$ m$^2$/s, and the Prandtl number, Pr, is Pr=0.7.

To fully define the device according to FIG. 14, the following parameters need to be determined: (1) length of chemical deposit and length of gap between chemical deposits and (2) conduit height. In order to adequately select these parameters, we need to determine the flux of acetone to the surface.

Step 2: Determine the Flux of Acetone to the Surface

Assuming incompressible flow, constant physical properties, and negligible body forces, the concentration boundary layer thickness, $\delta_c$, is given by the following relationship:

$$\delta_c = \frac{\delta}{Sc^{1/3}}$$

where $\delta$ is the thickness of the hydrodynamic (velocity) boundary layer and Sc is the dimensionless Schmidt number that is used to create momentum and mass transfer analogies. The Schmidt number is given by:

$$Sc = \frac{v}{D}$$

where v is the kinematic viscosity and D is the diffusivity. The thickness of the hydrodynamic boundary layer is given by:

$$\delta = \frac{5x}{\sqrt{Re_x}}$$

where x is the distance from the entrance of the conduit and Re is the dimensionless Reynolds number which, given the rectangular slit geometry, is given by:

$$Re_x = \frac{u \cdot x}{v}$$

where u is the velocity of the gas and v is the kinematic viscosity. The velocity is, of course, equal to the flow rate divided by the cross-sectional area.

$$u = \frac{Q}{W \cdot h}$$

where Q is the flow rate of the gas stream, W is the width, and h is the height. Therefore, by combining the above equations, the thickness of the concentration boundary layer is given by:

$$\delta_c = \frac{5x}{Re^{1/2}Sc^{1/3}} = 5 \cdot v^{1/6} \cdot D^{1/3} \cdot Q^{-1/2} \cdot (x \cdot W \cdot h)^{1/2}$$

The units of the thickness are in meters. Assuming that mass transfer in the direction of flow is dominated by convection (and not diffusion) and assuming that the flow is uniform with respect to the width of the conduit, the diffusion is directed only unidirectional, from the bulk stream to the surface. The flux of molecules to the surface is given by Fick's Law:

$$N = -D\frac{dC}{dy} \sim D\frac{\Delta C}{\Delta y} \sim D\frac{C_{bulk} - C_{surface}}{\delta_c - 0}$$

where $C_{bulk}$ is the concentration of acetone in the bulk stream (mol/m$^3$). Assuming an instantaneous surface reaction, the concentration of analyte at the surface would be approximately equal to 0. Under this theoretical set of conditions, the above equation reduces to:

$$N \sim D\frac{C_{bulk}}{\delta_c}$$

the above equation can be modified to consider more complicated chemical kinetics and/or other conditions to determine the flux of analyte to the surface. Applying the relationship for the concentration boundary layer as computed above, the surface flux of analyte is given by:

$$N \sim \frac{1}{5} \cdot \frac{D^{2/3}}{v^{1/6}} \cdot \frac{C_{bulk} \cdot Q^{1/2}}{(x \cdot W \cdot h)^{1/2}}$$

Thus, the flux to the surface is directly proportional to the concentration and the square root of the flow rate. The flux is also inversely proportional to the distance from the leading edge.

We want to maximize N. From this equation we conclude that the surface flux is driven by geometric and flow parameters. It is important to note that the above methodology can be adapted to encompass more complicated scenarios including chemical kinetics, which would necessitate, for example, the incorporation of kinetic coefficients in the solution.

Step 3: Determining Parameter Values

Another consideration is the length of chemical deposition. In other words, if the chemical is immobilized in a discontinuous fashion, what is the ideal immobilization length?

If the chemical is distributed in a discontinuous fashion as described earlier in this specification, the amount of analyte that will be involved in the reaction increases tremendously. The surface flux of acetone is given below as:

$$N \sim \frac{1}{5} \cdot \frac{D^{2/3}}{v^{1/6}} \cdot \frac{C_{bulk} \cdot Q^{1/2}}{(x \cdot W \cdot h)^{1/2}}$$

While the chemical deposition on the conduit surface is continuous, the flux of analyte to the surface decreases as a function of distance from the leading edge. The maximum flux to the surface occurs at a point extremely close to the leading edge. However, as has been described in detail previously, if the growth of the concentration boundary layer is interrupted by a lack of chemical reagent or some type of flow interruption, the boundary layer will reform and a new leading edge will be created. Nevertheless, during this "interruption," there will be no flux to the surface and no reaction (and therefore no heat). Therefore, we must balance the diminished flux due to build-up of the boundary layer with the high and then lack of flux with the chemical patterning.

Figure 29:
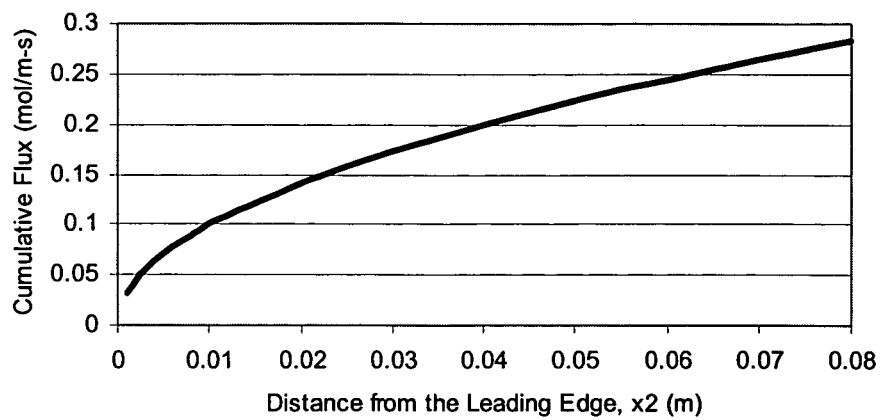
FIG. 29 is a graph showing the cumulative flux of analyte as a function of distance from the leading edge of a surface.

Accordingly, the question is: what is the ideal chemical deposit length and gap between deposits? The cumulative flux of acetone between the leading edge, x=0, and some distance, x=$x_2$, is given by:

$$\begin{aligned}N_{cum} &= \int N dx \\ &= \frac{1}{5} \cdot \frac{D^{2/3}}{v^{1/6}} \cdot \frac{C_{bulk} \cdot Q^{1/2}}{(W \cdot h)^{1/2}} \cdot \int_{x=0.001}^{x=x2} \frac{1}{x^{1/2}} dx \\ &= K \cdot x_2^{1/2}\end{aligned}$$

where K is a lumped constant consisting of the other parameters, which, for this aspect of the problem are assumed to be constant. Assuming K to be K=1 for the sake of simplicity, FIG. 29 shows the nature of the relationship between the cumulative flux and distance from the leading edge. Therefore, the rate of increase of the cumulative flux decreases as the distance from the leading edge increases. For an interrupted pattern to be effective, the cumulative flux over a distance must be more than half of the cumulative flux over four times that distance. Written mathematically, $$N_{cum}(x_{ideal}) > \frac{1}{2} \cdot N_{cum}(4 \cdot x_{ideal})$$

Using the above relationship, if, for example, $x_{ideal}=0.01$, there will be two distances between $0<x<0.02$ m and $0.04<x<0.06$ m where chemical will be patterned. During $0.02<x<0.04$ m, the chemical boundary layer will be depleted. With this patterned method, the cumulative flux over the entire 0.0762 m length will be:

$$N_{cum} = 0.381 \frac{mol}{m \cdot s}$$

versus $$N_{cum} = 0.276 \frac{mol}{m \cdot s}$$

if the entire 0.0762 m length were coated with chemical. This is 38% more efficient.

However, if $x_{ideal}=0.005$, the cumulative flux over the entire 0.0762 m length will be:

$$N_{cum} = 0.539 \frac{mol}{m \cdot s}$$

versus $$N_{cum} = 0.276 \frac{mol}{m \cdot s}$$

if the entire 0.0762 m length were coated with chemical. This is almost 95% more efficient. This can be seen in Table 2, below.

TABLE 2

| RANGE (M) | | CHEMICAL | FLUX |
|---|---|---|---|
| 0 | 0.005 | Yes | 0.07 |
| 0.005 | 0.01 | No | 0 |
| 0.01 | 0.015 | Yes | 0.07 |
| 0.015 | 0.02 | No | 0 |
| 0.02 | 0.025 | Yes | 0.07 |
| 0.025 | 0.03 | No | 0 |
| 0.03 | 0.035 | Yes | 0.07 |
| 0.035 | 0.04 | No | 0 |
| 0.04 | 0.045 | Yes | 0.07 |
| 0.045 | 0.05 | No | 0 |
| 0.05 | 0.055 | Yes | 0.07 |
| 0.055 | 0.06 | No | 0 |
| 0.06 | 0.065 | Yes | 0.07 |
| 0.065 | 0.07 | No | 0 |
| 0.07 | 0.075 | Yes | 0.07 |
| 0.075 | 0.08 | No | 0 |
| | | TOTAL | 0.56 |

Practically, it may be difficult to pattern the chemical in this discontinuous fashion, depending on the application. However, clearly, if it is possible, it is advantageous to do so as there is twice as much analyte diffusing to the surface with 50% of the reacting chemical immobilized on the sensor.

To operate in an environment where the flux is maximized and therefore possibly prior to the fully-developed flow regime, the hydrodynamic boundary layer thickness must be less than half of the conduit height. Therefore, the concentration boundary layer is confined by the height:

$$\delta = \frac{5x}{\sqrt{Re_x}} = 5 \cdot v^{1/2} \cdot x^{1/2} \cdot \left(\frac{W \cdot h}{Q}\right)^{1/2} < \frac{h}{2}$$

Figure 30:
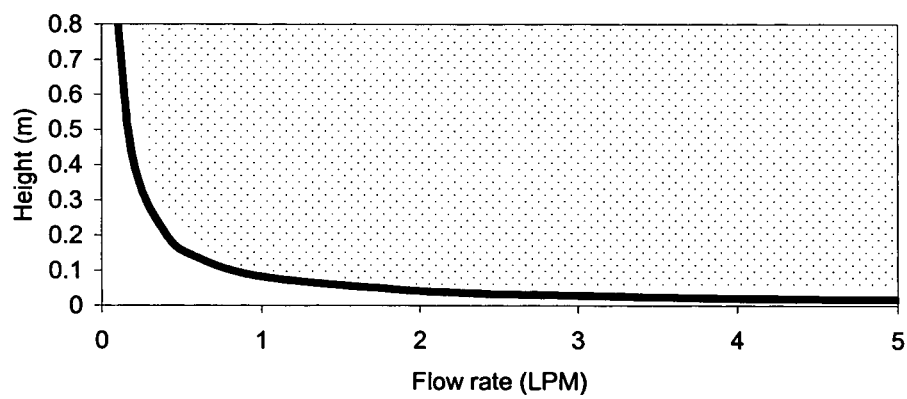
FIG. 30 is a graph illustrating a method for selecting conduit height.

The maximum length, x, is 0.0762 m. The conduit width, W, as previously stated is W=0.0106 m. Therefore, this inequality can be shown in FIG. 30. The entry length, Le, is the length required before the flow is fully developed, which means that the velocity profile does not change from one point to the next along the length of the conduit. To be in the non-fully developed region and assuming a rectangular slit geometry, the thermopile would be placed within the entrance length, which would be:

$$Le \approx 0.04 \cdot h \cdot Re_D \approx \frac{0.08}{v} \cdot Q \cdot \frac{h}{W+h} > 0.0762m$$

Note that $$Re_D = \frac{u \cdot D_h}{v}$$

where $D_h$ is the hydraulic diameter.

Figure 31:
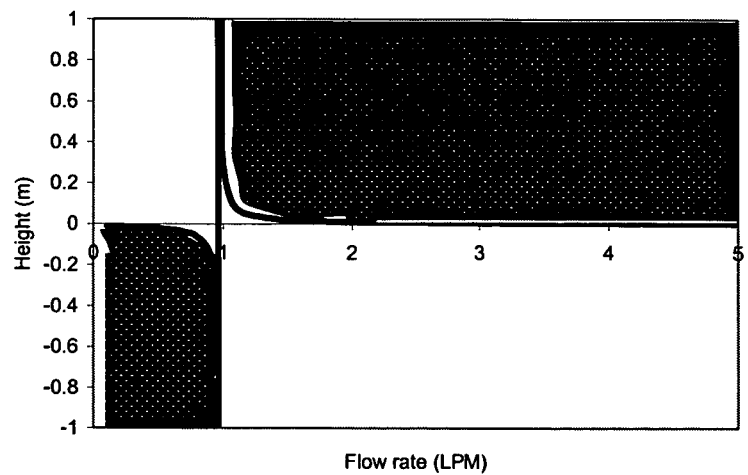
FIG. 31 is another graph illustrating a method for selecting conduit height.

The entry length must be at least 3", which was stated in the problem statement as the maximum length of the device. FIG. 31 is a graph of this inequality. Since heights obviously cannot assume negative values, a flow rate greater than approximately 1 LPM is needed to ascertain that the entry length is not achieved within the 0.0762 m (3") length of the device.

Figure 32:
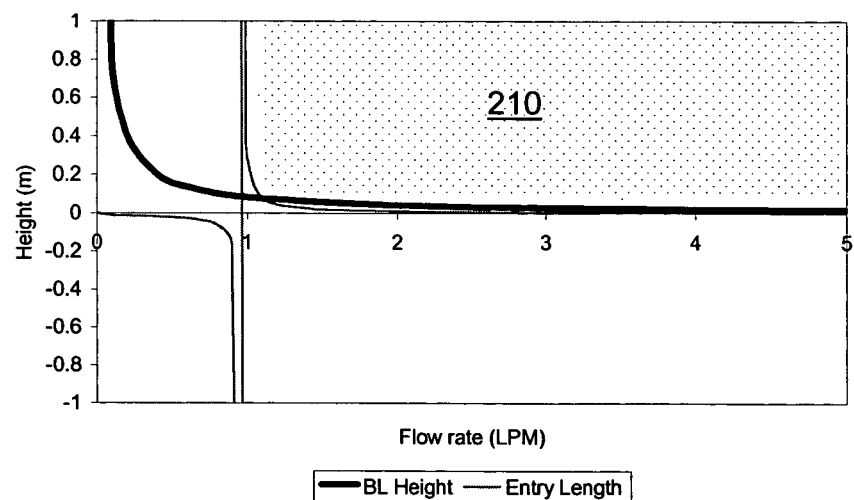
FIG. 32 is another graph illustrating a method for selecting conduit height.

Combining the above two constraints, we obtain the relationship shown in FIG. 32, where the shaded region is the solution to the set of two inequalities.

Looking at the equation of the analyte flux to the surface, as the height of the conduit increases, the flux decreases. Therefore, the height should be kept at the smallest possible value, while still conforming to the above constraints shown graphically in FIG. 32.

Turning to another method according to the invention, while the preferred embodiments may be used in highly controlled environments, it is also possible that the device be used in situations where user variability is a concern. One variable that one may account for is the flow rate of the user.

As we have seen in the previous model, as the flow rate increases, the analyte flux to the surface increases. However, as the flow rate increases, the amount of heat that is dissipated to the environment also increases. Therefore, as the flow rate increases, it is desirable to balance the increase in heat generated with the increase in heat dissipated.

This model serves to investigate the impact of flow rate on the signal and attempts to identify particular signal features that may be independent of flow rate.

Assuming that the thicknesses of the chemical on the thermopile and the thermopile substrate are low and/or that their thermal conductivity is high, the temperature at the surface of the chemical is equal to the temperature of the thermopile. With this assumption, an energy balance of the thermopile yields:

$$\rho c V \frac{dT}{dt} = Q_{rxn} - hA(T - T_{bulk})$$

where $Q_{rxn}$ is the heat generated by the chemical reaction, $\rho$ is the density of the thermopile metals, c is the heat capacity of the thermopile metals, V is the volume of the metals, h is the heat transfer coefficient, and A is the cross-sectional area of the thermopile, which is the length multiplied by the width.

While the heat generation term may be sum of heats generated by a series of reactions, for this example, we assume that it is the heat generated by the acetone-interactant reaction only. Therefore, $$Q_{rxn} = N \cdot \Delta H = \left[ \frac{1}{5} \cdot \frac{D^{2/3}}{v^{1/6}} \cdot \frac{C_{bulk} \cdot Q^{1/2}}{(x \cdot W \cdot h)^{1/2}} \right] \cdot \Delta H$$

And, the heat transfer coefficient is commonly correlated using the Nusselt number:

$$Nu = \frac{h_L \cdot L}{k} = 0.332 \cdot Re_L^{1/2} \cdot Pr^{1/3}$$

where k is the thermal conductivity, L is the length over which it is desirable to compute the average heat transfer coefficient, and Pr is the Prandtl number, which is equal to the kinematic viscosity divided by the thermal diffusivity. Rearranging terms, $$h_L = 0.664 \cdot k \cdot Pr^{1/3} \cdot \sqrt{\frac{u}{v \cdot L}}$$

Substituting the flow rate for the velocity, we get:

$$h_L = 0.664 \cdot k \cdot Pr^{1/3} \cdot \sqrt{\frac{Q}{v \cdot L \cdot W \cdot h}}$$

$$= 0.664 \cdot k \cdot \frac{Pr^{1/3}}{v^{1/2}} \cdot Q^{1/2} \cdot \sqrt{\frac{1}{L \cdot W \cdot h}}$$

Accordingly, $$\rho c V \frac{dT}{dt} = \left[ \frac{1}{5} \cdot \frac{D^{2/3}}{v^{1/6}} \cdot \frac{C_{bulk} \cdot Q^{1/2}}{(x \cdot W \cdot h)^{1/2}} \right] \cdot \Delta H - 0.664 \cdot k \cdot$$

$$\frac{Pr^{1/3}}{v^{1/2}} \cdot Q^{1/2} \cdot \sqrt{\frac{1}{L \cdot W \cdot h}} (L \cdot W) \cdot (T - T_{bulk})$$

We are performing this analysis to gain an understanding of the optimal flow rate range. Therefore, we lump the parameters together as follows:

$$\frac{dT}{dt} = K_1 \cdot \sqrt{Q} - K_2 \cdot \sqrt{Q} \cdot (T - K_3)$$

The solution to this differential equation is of the form:

$$T = \frac{1}{K_2} \cdot \left( K_1 + K_2 K_3 + e^{-(t+d)(K_2 \sqrt{Q})} \right)$$

where d is the integration constant.

This solution yields multiple conclusions. First, if we assume that the temperature of the reference junctions is constant or unaffected by the heat generated by the interactant-analyte enthalpic process, the temperature signature aforedescribed is actually of the same form as the temperature difference, which the thermopile converts to the output voltage.

From this response, we see that the temperature signature varies as a function of flow rate. Generally, as the flow rate increases, the temperature of the thermopile sensing junction decreases. Therefore, if a continuous signal is being measured, it is desirable to maintain low flow rates over the sensor.

However, at steady state or at maxima or minima (situations where $dT/dt=0$), the temperature response is independent of flow rate. Therefore, if the flow rate is controlled such that convection does not dominate over diffusive mass transport to the surface, it may be desirable to select signal features, such as the maximum, minimum, or steady state response, when attempting to determine concentration levels.

Moreover, if the concentration level is determined from the maximum, minimum, or steady state value, it will be possible to plug this value into the equation and, using other values, compute the flow rate of the air stream.

This model is limited in some circumstances by the fact that the flow rate was assumed to be constant with time. If the flow rate was in fact changing as a function of time, as one skilled in the art would appreciate, the solution to the above differential equation would need to be modified.

As may be appreciated, under certain circumstances, to determine the concentration of the one or more analytes, it may be desirable to process the signal from the thermal sensor considering other factors, such as flow rate and temperature. This can be done in various ways. For example, the overall device may include a temperature measurement unit and a flow measurement unit which, like the thermal sensor, are coupled to a processor. Or, the signal itself may be processed using an algorithm, where certain signal features aid in determining the flow rate and/or temperature, and these parameters may, in turn, aid in interpreting an aspect of the signal so as to determine the overall concentration.

Packed beds may also be used with thermal sensors so as those that have been described herein. In the embodiment shown in FIG. 39, the analyte interactant 284 is immobilized within a packed bed 283 which is placed over the thermal detector 281 (e.g. the pyroelectric detector, thermopile, etc). The analyte 282 passes through the packed bed 283 and binds to the analyte interactant 284 in an enthalpic process which is measured by the thermal detector 281.

Under certain circumstances, use of a packed bed embodiment may be desirable. For example, if the flow rate is high, convection may dominate over diffusion to the surface, which could limit the efficacy of surface reactions. If the length of the packed bed is appropriately determined based on residence times, etc, it can ensure that all of the analyte has had an opportunity to interact with the analyte interactant within the packed bed. As a second example, if the concentration of analyte is high, a packed bed will increase the surface area for an interaction to occur.

The packed bed may be any material that can be linked to the analyte interactant. Examples may be or comprise microspheres or nanoparticles, which could be made of, for example, polymeric materials, silica, or metallic compounds.

Depending on the packing structure of the bed, the packed bed may serve as a filter based on size exclusion principles.

Figure 39:
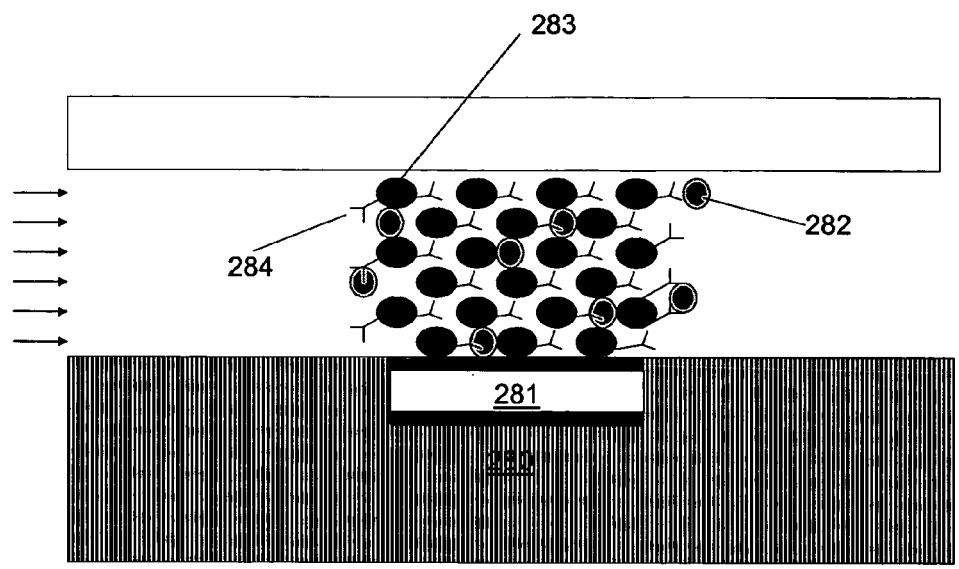
FIG. 39 is an embodiment of a thermal sensor with analyte interactant contained within a packed bed.
Figure 40:
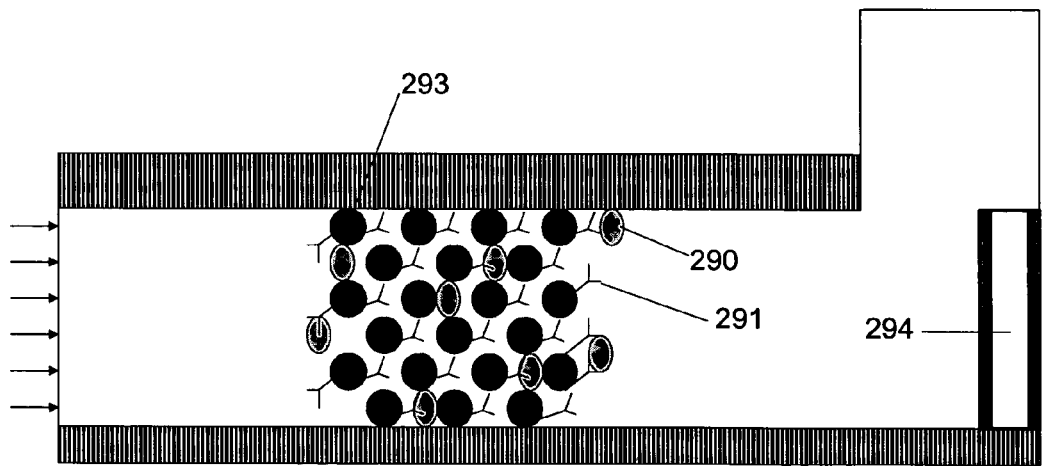
FIG. 40 is an embodiment of a thermal sensor that measures radiated heat from an enthalpic interaction.

In the embodiments generally described by FIG. 38 and FIG. 39, the predominant mode of heat transfer to the thermal detector is conduction. However, thermal detectors can also measure heat transferred via radiation. FIG. 40 exemplifies an embodiment that utilizes a thermal detector 294 to measure radiated heat that is generated from an enthalpic interaction between an analyte 290 and an analyte interactant 291.

Turning to the subject of temperature compensation, ideally speaking, an ideally designed and manufactured thermopile should exhibit common mode rejection and therefore any thermal changes in the environment should be simultaneously and equally experienced by the reference and sensing junctions thereby producing an output voltage of zero. However, under certain circumstances, the thermopile may register a non-zero voltage due to environmental conditions. Some of these conditions are described as follows: (a) the junctions are not perfectly balanced and therefore the thermopile does not have a common mode rejection ratio equal to one, and/or (b) there are major temperature fluctuations in the environment. To solve either of these or related problems, a temperature compensating unit may be used. One example of this temperature compensating unit is a "reference thermopile," which would serve to quantify any type of imbalance between the sensing and reference junctions.

Figure 35:
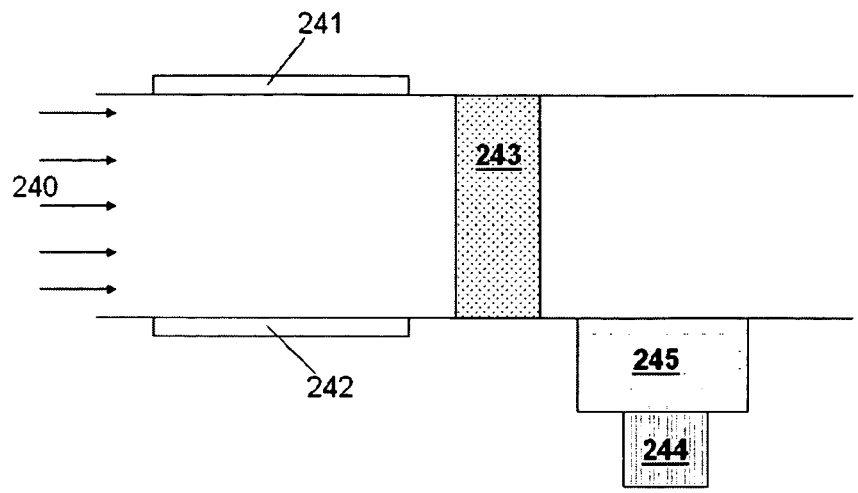
FIG. 35 is an embodiment of the invention that utilizes a temperature compensating unit.

FIG. 35 shows an embodiment according to another aspect of the invention that utilizes a temperature compensating unit. The gas containing the analyte 240 passes through a conduit where the top contains an interactant 242 that is specific for an interfering substance and the bottom contains an interactant 241 that is specific for a second interfering substance. The gas then comes in contact with a temperature compensating unit 243 which is coupled to the microprocessor 244. The microprocessor interprets the signal from the sensor 245 considering the signal from the temperature compensating unit. Based on both of these inputs, the microprocessor then produces an output that is descriptive of the concentration of the analyte.

Figure 33:
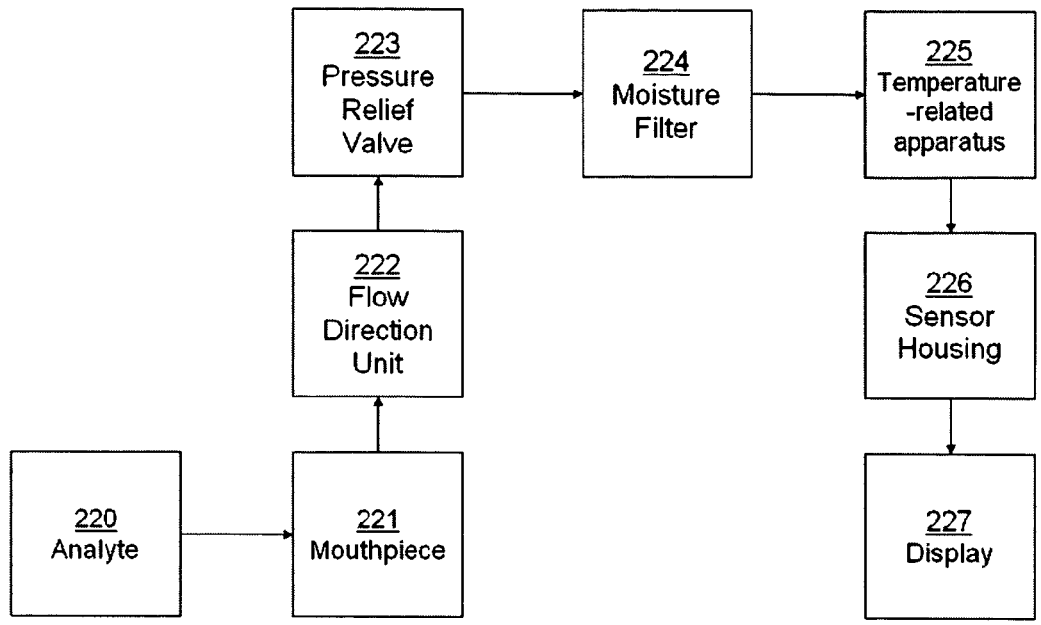
FIG. 33 is a functional block diagram illustrating the configuration of an embodiment of one aspect of the invention.

In some instances, it is desirable to regulate the flow rate of the gas, strip the air of any moisture or water droplets, and account for temperature when considering the signal response. FIG. 33 shows a block diagram of a preferred embodiment of the invention when exposed to an analyte of interest. The user exhales a gas containing the analyte 220 into a disposable mouthpiece 221 which passes through a flow direction unit 222. The flow direction unit serves either or both of the following functions: (a) ensures that only a deep lung sample of air is allowed to pass through the remaining components and (b) ensures that flow is in one-direction only. Next, the gas passes through a pressure relief valve 223 which may contain some sort of continuous feedback, such as a whistle, to make certain that the user is blowing hard enough into the device. For example, the whistle may sound if the user is generating greater than 2 psi. The gas then passes through a moisture filter 224 which may have an inherent pressure drop thus serving to decrease the flow rate of the gas, which may be advantageous. Drierite could be used as the moisture filtration material. For example, in some embodiments, a flow rate of around 100 mL/min is preferable. If necessary or desirable, the gas may pass through a temperature-related apparatus 225. This apparatus can do any of the following functions: (a) serve to account for imbalances between the reference and sensing junctions of the thermopile, (b) measure the absolute temperature of the incoming gas stream, and/or (c) bring the temperature of the incoming gas stream to approximately the same temperature as the device itself. The gas then passes through the sensor housing 226 where it contacts the sensor. The output of the sensor is in some fashion presented on a display 227.

Figure 34:
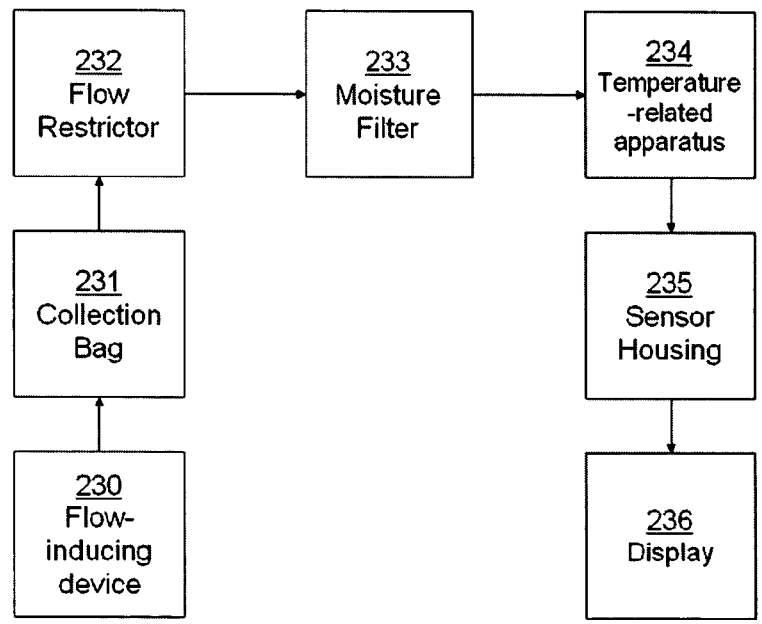
FIG. 34 is another functional block diagram illustrating the configuration of an embodiment of one aspect of the invention.

In some instances, it may be necessary or desirable to collect a breath sample in some type of collection bag, such as a Tedlar bag. This may be important for calibration purposes. FIG. 34 presents an embodiment according to another aspect of the invention that is amenable to use with a collection bag. Some type of flow-inducing device 230, which may be as simple as a book placed atop the collection bag 231, causes the gas containing the analyte contained within the collection bag to pass through a flow restrictor 232, a moisture filter 233, a temperature-related apparatus 234, and then the sensor housing 235. The output of the sensor is in some fashion presented on a display 236.

Figure 24:
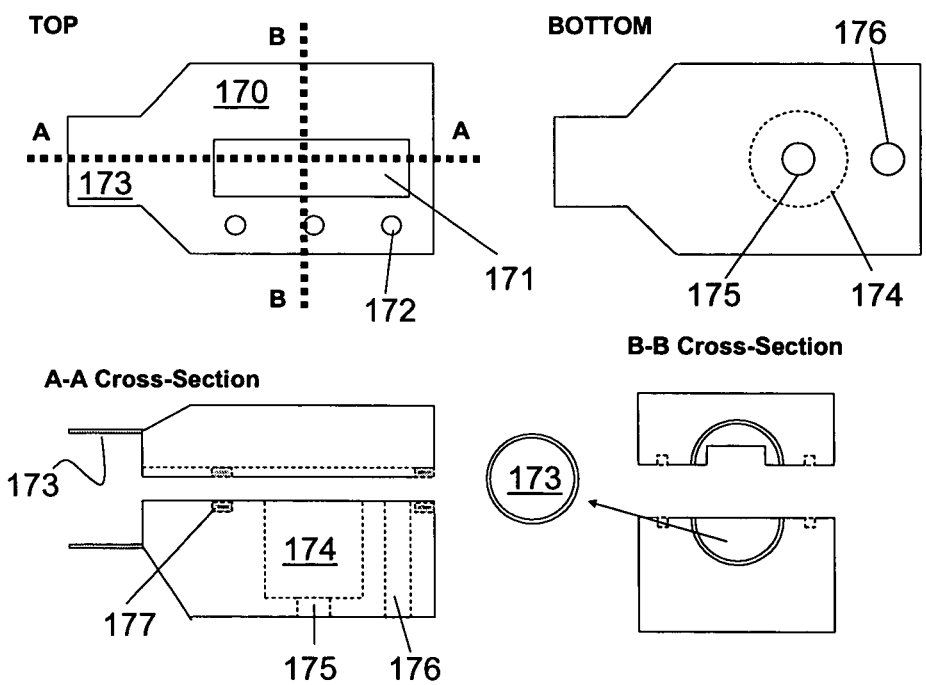
FIG. 24 shows another embodiment of a flow chamber.
Figure 25:
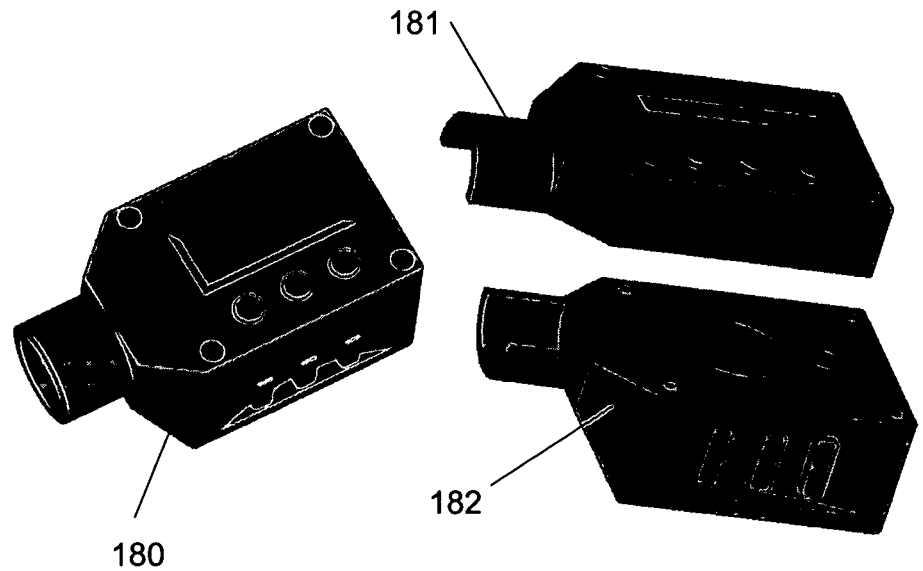
FIG. 25 shows a three dimensional construction of sensor housing.
Figure 27:
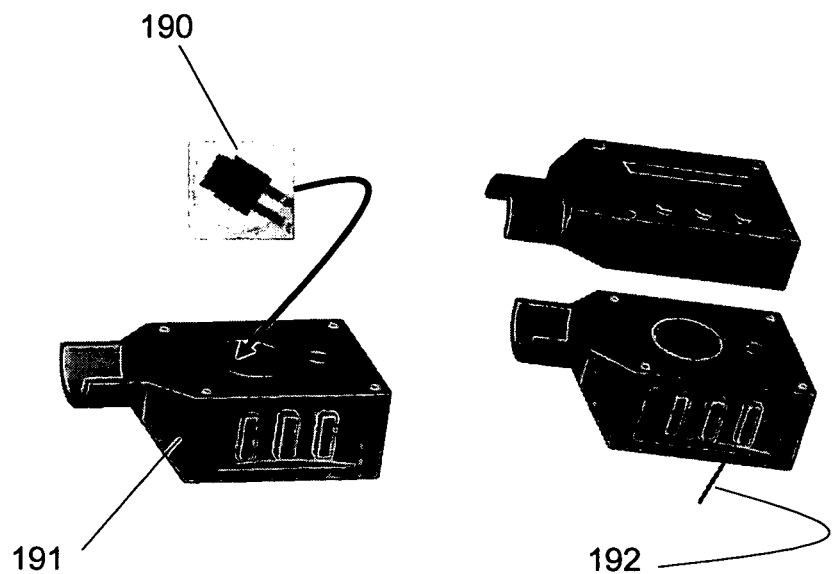
FIG. 27 shows placement of the thermopile within the sensor housing.
Figure 28:
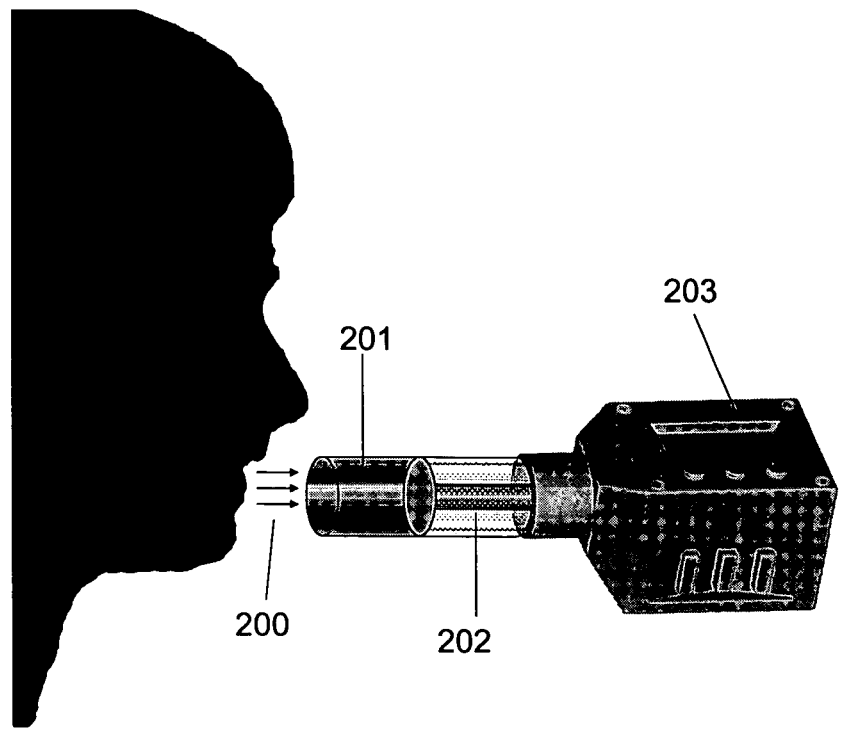
FIG. 28 shows a user blowing into a sensor according to a preferred embodiment of the invention that utilizes filters.

FIG. 24 shows an illustrative example of a device encasement, the top piece of which comprises a mouthpiece 173, a display 171, buttons 172 and surface. The top piece is attached to the bottom piece via two fasteners 177, which may include magnets, screws, or the like. The thermal sensor may be placed in a cavity 174 with leads exiting the device through one or two holes 175 or 176. The exiting leads may or may not be desirable, depending on the application. FIG. 25 shows a perspective diagram of the encasement shown in FIG. 24. FIG. 27 shows how the thermal sensor of this embodiment 190 may be placed into the bottom piece of the encasement 191. FIG. 28 shows that the embodiment of FIG. 24 may be used in conjunction with filters 201 and/or restrictors 202.

Figure 36:
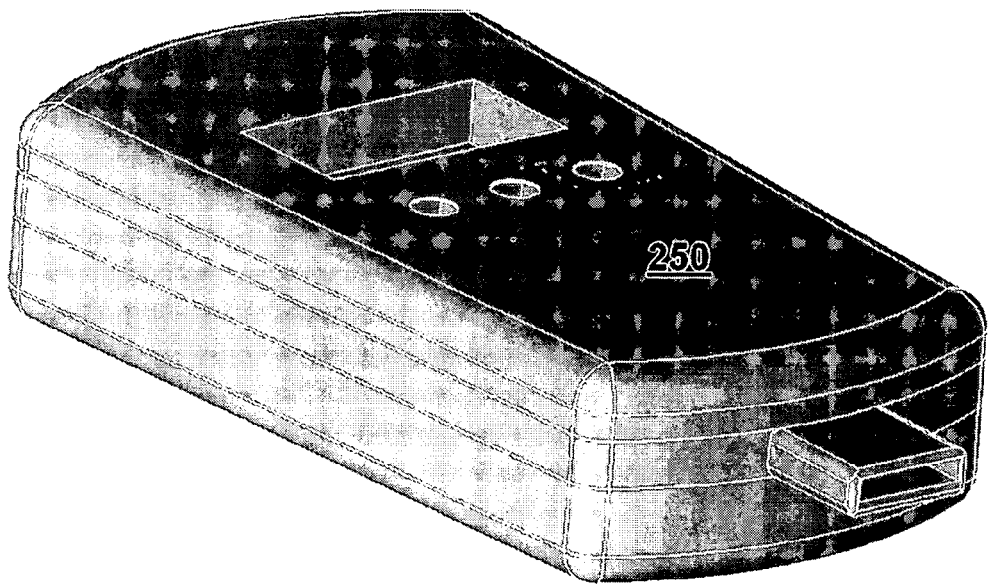
FIG. 36 is a perspective diagram of an embodiment of the invention.

FIG. 36 shows another example of a device encasement 250.

EXAMPLE 1

Figure 54:
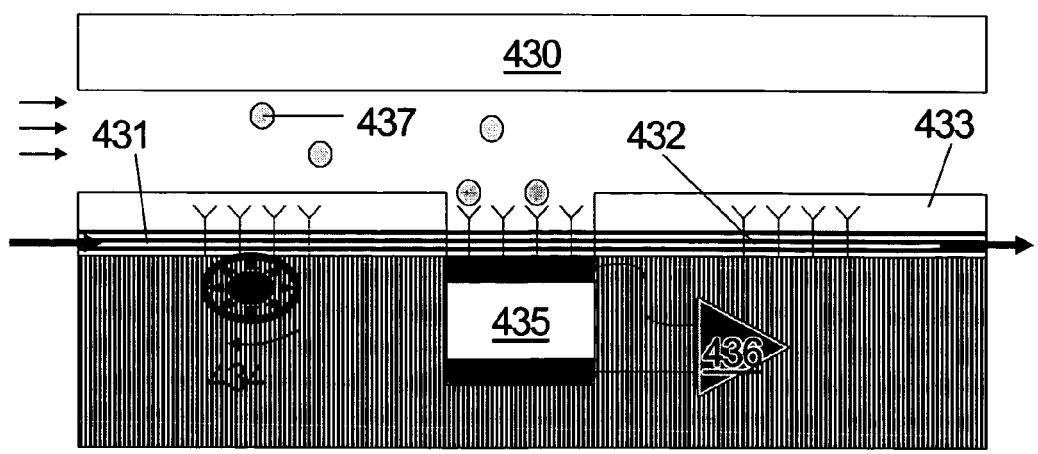
FIG. 54 is an embodiment of a pyroelectric sensor.

FIG. 54 shows an embodiment that utilizes a pyroelectric detector 435. The analyte 437 passes through a conduit and interacts with an analyte interactant 432 which is immobilized on a test strip 431. The test strip 431 is passed through the conduit by a mechanism 434, such as a gear, motor, etc, and is guided by a strip director 433. The output of the pyroelectric detector 435 is processed by a signal processing unit 436.

As a general matter, the response of thermal sensors is improved by use of thin-film materials. In some instances, if the expected signal is large, the magnitude of the signal is perhaps not an issue. However, the thermal time constant (i.e. the response time) is typically impacted if the heat capacity is high. Accordingly, under most circumstances, it is desirable to employ thin-film materials. With this type of test strip embodiment, to ensure good thermal contact, it is desirable if the test strip is in good mechanical contact with the sensor.

A specific example of this embodiment uses a 9 μm polyvinylidene fluoride (PVDF) film that is coated on both sides with NiAl to serve as electrodes. The film can be cut using a razor blade or ceramic scissors to a 1 cm×1 cm surface area. Electrical contact will be made via the electrodes to shielded wire. This film is immobilized onto a bottom piece of a flow chamber. Between the leading edge and the sensor, a cover piece will be mounted atop the bottom piece of the flow chamber that will serve as a test strip director. The bottom piece will have an opening under which a microgear and gear belt will be located to facilitate moving the test strip through the test strip director and over the sensor to allow for the desired interactions.

The test strip is not limited to a particular material. In this example, a polyester film such as Mylar is used. The Mylar will be cut into 1 cm×10 cm strips. The location of the analyte interactant will be noted using print-on demarcations. The analyte interactant will be patterned in an alternating fashion with a void space. In this way, when the analyte interactant is exposed to the fluid, heat may be generated (if the analyte is present), and this heat will be measured by the detector. When the portion of the test strip without analyte interactant is exposed to the fluid, there will be no heat generated (or solely noise, interfering signals, and non-specific adsorption will be measured and serve as a reference).

The flow chamber shown in FIG. 54 is, of course, only one example of such a flow chamber. In the event that the desired thermal contact between the test strip and the pyroelectric sensor cannot be made, it is possible to use pyroelectric ribbon as the test strip itself and pattern the analyte interactant directly onto the ribbon, which would require moving the ribbon through the sensor. Or, to provide mechanical rigidity, the entire bottom plate may be moved simultaneously with the test strip.

This embodiment may be used to measure glucose concentrations using, for example, glucose oxidase as the analyte interactant. Glucose oxidase (2 mg, Type VII, 137 units/mg) is mixed with a glutaraldehyde cross-linking agent (1 µL, 25%) and mixed for 15 seconds. This gel is applied evenly over the surface of the test strip and allowed to cure. A photomask with alternating blocked/unblocked portions is placed over the test strip and the exposed portions of the test strip are irradiated to inactivate the enzyme. In this manner, the thermal load of the test strip is constant throughout. It is possible, of course, to only coat the gel onto the desired parts of the test strip (instead of the entire strip) to avoid the irradiation step.

To test the performance of the sensor, solutions containing 10 mM pH 7.4 phosphate buffer solution with varying glucose concentrations (25, 50, 75, . . . , 250 mg/dL) can be prepared and stored in 1 L flasks. The fluid may be pumped from the flask and into the flow chamber using a fluid pump from a suitable source.

Depending on the embodiment and the knowledge of the chemistry, it may or may not be helpful to perform control experiments. If it is, examples of control experiments are provided. The first control experiment will measure the background noise of the pyroelectric sensor to flowing fluid. The second will measure the output of the pyroelectric sensor to the moving test strip in a flowing fluid. If an unexpected result occurs, this ought to be well-characterized and, in future experiments, subtracted from the test signals.

EXAMPLE 2

In this example, a thermal sensor for oligosaccharide detection is described. Oligosaccharides ("glycans") are associated with various pathologies, including cancer. These oligosaccharides may be found on the periphery of the cell on the glycocalyx. They also may be found free flowing in blood attached to biomolecules such as proteins. During disease states, the concentration of glycans may increase, the structure of the oligosaccharide may be modified or altered, or neoexpression of certain glycans may occur. Accordingly, measuring glycans can serve as tremendous biomarkers.

Although sugars are well-known as the "third language of life" (genomics, proteomics, glycomics), because glycoscience is an emerging field, it is important to understand why it is important to measure glycans. First, in some instances, glycans have served as biomarkers where other disease markers have not been identified or are limited (e.g. in multiple sclerosis). Second, many papers have shown that even when the protein concentration remains the same, "the structure of its carbohydrate chains also changes, in particular, the branching, the degree of sialylation, and the number of terminal [sugar residues]." Thus, even if the protein structure remains the same, the carbohydrate chains on a given biomolecules or cell may be altered and indicate pathology.

Oftentimes, particularly for measurement of biological analytes, it is desirable to employ an aptamer as the analyte interactant. This example provides an example method for selecting an aptamer for a glycoprotein known as $\alpha_1$-Acid glycoprotein (AGP), which is found under normal conditions in concentrations such as 0.2-1 mg/mL. AGP is an acute phase glycoprotein that is approximately 43 kDa in size and has five N-linked glycans on the surface of the protein. During pathology, such as cancer, these concentrations increase multiple-fold. Also, there are changes to the fucosylation and/or sialylation index of the carbohydrate chains.

SELEX is an iterative technique that aids in identifying high affinity analyte interactants (e.g. aptamers) to target molecules. The SELEX process can include a negative control step to aid in identifying an aptamer which not only binds to the target glycan with high affinity but also discriminates against known interfering substances. Also, if desirable, this process can be used to identify an aptamer that is cross-reactive between molecules with similar characteristics.

In this example, an aptamer library ($\sim 10^{17}$ oligonucleotides) with 80 base pairs is created. Thereafter, the standard SELEX process is used and the non-binding RNA sequences are filtered via elution using a nitrocellulose filter. Because of the application, the following modifications are made to the procedure. Once the aptamer library has been reduced ($\sim 5$ steps), a negative control step is performed against interfering substances where the eluted RNA sequences, instead of being discarded, are amplified for the remainder of the screenings against AGP. In this way, similar oligosaccharide structures on non-AGP protein structures will be minimized. The last $\sim 10^2$ RNA sequences that have been identified as high affinity aptamers will be saved for further analysis. However, the refinement will continue until we have identified a single aptamer candidate.

There are other forms of SELEX including, CE-SELEX, Toggle-SELEX, tailored-SELEX, and others. If glycans that are attached to transmembrane proteins of cells are desired to be measured, CE-SELEX may be the appropriate technique to use. Also, while aptamers are extremely robust molecules, under certain circumstances and for certain aptamers, they can be broken down by nucleases. There are aptamers that can be modified to increase their stability. For example, spiegelmers that mirror the sequence of the selected aptamers can be synthesized. Because most spiegelmers employ L-ribose instead of D-ribose, they are resistant to nuclease degradation. If spiegelmers do not help the potential aptamer-degradation problem, it may help to pre-treat the fluid containing the analyte by heating to deactivate enzymatic activity. Also, during the synthesis step, it may be desirable to biotinylate the aptamers so that it is not necessary to perform this step post-synthesis for immobilization purposes.

Affinity and specificity are different properties. High affinity does not necessary imply high specificity. In this regard, it is important to note that SELEX identifies high affinity ligands. The specificity of final aptamers may be improved by a negative control step in SELEX. Or, the final $\sim 100$ aptamer sequences identified via SELEX can be screened against interfering substances and the AGP to test for specificity. This can be done using an aptamer array.

These aptamers (biotinylated during synthesis) can be incubated separately with streptavidin agarose beads to form aptamer beads. The aptamer beads are then loaded into rectangular wells of a 10×10 chip.

For glycans, interfering substance (negative controls) can be determined by altering any of the following: (1) the terminal sugar linkage, (2) the terminal or near-terminal sugars themselves, and (3) a combination of these. For AGP, for example, (Fucα1,2)Galβ1 . . . -conjugated BSA and/or (NeuAcα2,4)Galβ1 . . . -conjugated BSA may be used as negative controls.

The AGP and the negative controls can be fluorescently tagged with an Alexa-Fluor label. It may be easier to tag the proteins than the aptamers because of the size differential but this depends on the structure. The AGP independently is contacted with the chip for a period of 4-6 hours and the fluorescence level is measured. The same procedure is repeated with the negative controls. Aptamers that bind to AGP exclusively or to a greater extent than the negative controls are selected. If no aptamers meet this criteria, a decision is made as to whether to reperform SELEX or attempt to filter out interfering substance before exposure to the sensor.

Of course, aptamers can be used in conjunction with a number of different sensors. If a pyroelectric sensor embodiment that utilizes a test strip is used, the following are examples for patterning the test strip. For example, in one test strip, the aptamer is covalently bonded to a gold-plated pyroelectric ribbon test strip. The aptamers will undergo a thiol-modification and the Au plated pyroelectric ribbon will be functionalized with sulfo-SMCC, which has an NHS ester group to covalently bond to amine-activated Au and a maleimide group to bind with the aptamer.

In a second example, a thin plastic such as Mylar that has been coated with streptavidin may be used as a test strip. The aptamers, which may be biotinylated during synthesis, bind to the streptavidin. It is usually important to completely saturate the streptavidin binding sites to minimize any errors from test strip to test strip.

In this example, the aptamers may be patterned to the test strip in a variety of different ways including using a copper metal mask. In this case, a copper metal mask will be micro-machined with holes in the locations where the aptamers are to be immobilized. This mask will be fastened to the test strip and the combination of the top portion of the test strip and mask is coated with streptavidin for surface treatment. Once the streptavidin has cured, the test strip is unclamped from the mask and the strip is immersed in a solution containing three times the necessary concentration of the aptamer. After sufficient time for binding to occur, the test strip is rinsed with an appropriate buffer solution. This procedure is repeated at least twice to ensure complete saturation of all reaction sites. If the difference in thermal load of the void-aptamer spots becomes an issue, it may be necessary to coat the non-aptamer binding surfaces with a non-binding aptamer so that surface make-up is similar through the test strip.

It is important to note that this technique may need to be modified for measuring multiple glycans or, in general, multiple analytes. Or, alternatively, if multiple aptamers are needed to specifically identify a single glycan, an array-based test strip may be developed. In this situation, instead of the test strip simply moving in one direction to allow for modulation, the test strip would be moved back and forth between the void spaces and the spaces containing an aptamer. To create this array, the automated robotic processes used in microarray technology may be employed to spot aptamer onto a surface. Depending on the number of aptamers to be patterned, the microwell technique described earlier may also be used. An array of sensors may also be necessary.

Turning again to the use of aptamers as analyte interactants, there are many benefits to using an aptamer. Aptamers can be stable and reusable and they may be easy to immobilize. Perhaps the greatest advantage, however, is that selectivity can be achieved. Because of the number of aptamers that can readily be synthesized, identifying one or more aptamers that will serve to identify the presence of a particular analyte can be achieved.

The following is an example of how an aptamer interactant may be used. The thermopile metals are deposited onto a substrate. The substrate, in this case on the side opposite the metals, is protected except for the area over the thermopile sensing junctions ("surface"). The non-protected surface is functionalized such that aptamers can bind directly to it or, alternatively, nanobeads containing the aptamer are deposited over this surface. When the analyte passes over the sensing junctions of the thermopile, the analyte binds to the aptamer. This binding phenomenon produces heat, which is measured by the thermopile.

To increase the amount of heat generated by the interaction of the analyte and the aptamer, the aptamer can be designed to have multiple binding sides. Additionally, if the aptamer is immobilized onto silica beads or nanobeads, this increases the effective number of molecules available for reaction per unit surface area, which in turn increases the amount of heat that is generated.

Typically the analyte is adsorbed onto the aptamer. Therefore, the analyte can be released in a short period of time by promoting desorption by, for example, increasing the temperature of the surface on which the aptamer is bound. In this way, the sensor with immobilized aptamer can be reused multiple times.

In the event that the analyte is too small to bind between within the aptamer, the analyte may be pre-treated within the overall device to selectively attach it to a larger molecule such as, for example, a fluorophore.

In certain instances, once the thermal sensor has been exposed to the gas containing the analyte, it may be necessary to purge the conduit of the gas. This may be necessary for a variety of reasons. For example, in breath analysis, especially if the breath has not been stripped of moisture or bacteria, it may be important to remove any residual water/interactants bacteria from the thermal sensor and/or the conduit so as to prevent corrosion or contamination.

Purging the conduit can also allow for reverse reactions or physical phenomena to occur, which may help to bring the overall system back to equilibrium. For example, if an adsorption interactant were selected, exposure to the analyte will promote adsorption, but exposure to a purging gas stream may help promote desorption.

Purging can also help promote reverse reactions. For example, consider the following reaction A+B←→C+D, where A is the analyte and B is the analyte interactant. If A is present in high concentrations (because, for example, a gas containing A is passed through the conduit), the net reaction will proceed in the forward direction. This will result in a build-up of C and D and a complete or partial consumption of B. If, then, A is removed from the system (either because there is no input to the conduit or because an input containing no A is input), the reverse reaction will proceed, which will result in replenishment of B.

In other instances, prior to exposure to the gas containing the analyte, it is advantageous for the analyte interactant to be exposed to a priming stream. For example, water may be passed through the conduit to allow water and the immobilized interactant to react, thereby forming a species that will interact with the analyte of interest. This is particularly desirable when an interactant is selected because it is stable, but perhaps needs to be activated to become truly reactive with the analyte.

It may also be desirable to utilize a priming stream to establish the temperature and flow regime. For example, if the overall device is placed in an environment where the environmental conditions are substantially different than those of its prior use, a priming stream may be helpful to calibrate the device.

Figure 26:
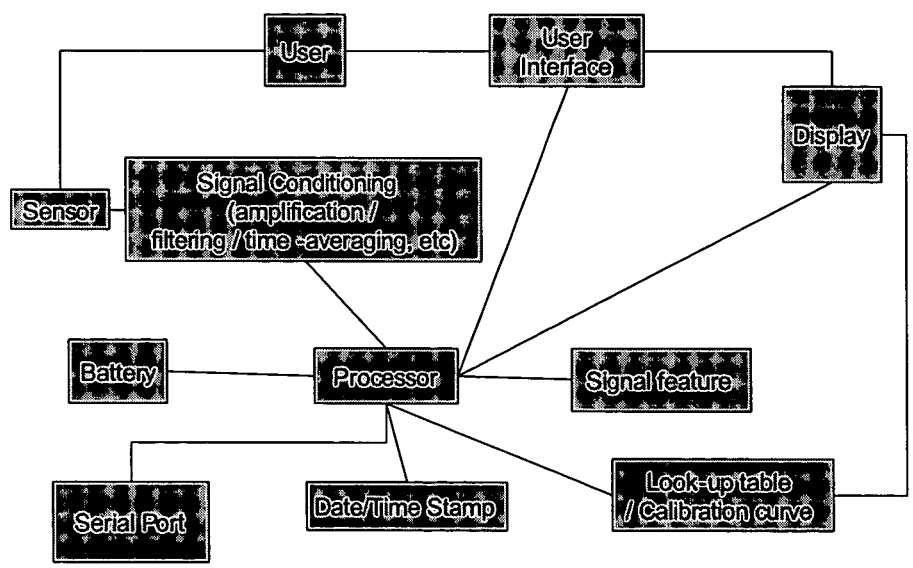
FIG. 26 is a flow diagram illustrating a preferred embodiment and its operation.

FIG. 26 shows a structure/function diagram of an embodiment.

In accordance with another aspect of the invention, a method for raw signal interpretation is provided. This method may be implemented in computer software. Depending on the application, different features of the signal from the thermal sensor may indicate the presence or concentration of the analyte. A new and useful method for processing this signal is as follows.

A baseline is calculated for a period of time such as 5 seconds. Following the computation of this baseline, the maximum and minimum values are stored. The absolute values of the maximum and minimum values received from the thermal sensor are compared. The greater value is called the peak value. The raw signal is defined as or set to be equal to the peak value minus the baseline. The raw signal then is converted into a displayable value, for example, based on a predetermined calibration chart or look-up table. This method can be illustrated as follows:

Once the "START TEST" button is pushed:
(1) Display "Wait . . . "
(2) Calculate BASELINE (average over first 5 seconds, approx 40 pts)
After 5 seconds:
(3) Display "Testing . . . "
(4) Store MAX and MIN
After 20 seconds:
(1) Compare abs(MAX) and abs(MIN); whichever is greater=PEAK;
Note that PEAK can only take on (+) values
(2) Compute: PEAK−BASELINE=RAW
(3) Access look-up table; convert RAW to VALUE
(4) Display "Your Value is: VALUE"
(5) Store DATE, TIME, and VALUE to memory Sensors according to the various aspects of the invention may be used in conjunction with supplementary or disposable/refillable components. For example, the sensor may be used with a software package that stores results of the sensor, a calibration unit, disposable/refillable cartridges of analyte interactant, or disposable filters.

Such sensors also may be used in conjunction with a calibration unit. This calibration chamber may be filled with a known quantity of air. Then a finite amount of analyte is injected into the calibration chamber and allowed to evaporate. The amount of analyte and the amount of air may be entered into a keypad or a spreadsheet to determine the concentration of the analyte. The calibration unit may then cause the calibration chamber to be exposed to the sensor. The output of the sensor may be evaluated in accordance with the concentration of the analyte so as to program the sensor.

Such sensors may also be used with disposable or refillable cartridges of analyte interactant. For instance, a test strip may be inserted into the device, said test strip containing some of the analyte interactant. These test strips may be used more than once or may be designed for single use only. Additionally, the test strips may contain multiple analyte interactants or single analyte interactants. Also, the test strips may contain interactants that complement interactants that are already on the sensor, e.g. to increase specificity and/or sensitivity.

Such sensors may be used with disposable filters. These filters may be or comprise bacterial filters, moisture filters, or filters for interfering substances.

The sensor 2 can be used in conjunction with a software package that could, via a USB cable or the like, store either the entire signal from the thermopile device or selected features therefrom. These values can be synthesized into a progress report, which may periodically be sent to a medical practitioner. Based on the progress report, the program can make suggestions for medication, lifestyle, or other changes.

Additional advantages and modifications will readily occur to those skilled in the art. For example, although the illustrative embodiments, method implementations and examples provided herein above were described primarily in terms of the conductivity or current state of the conduction paths, one also may monitor or control voltage states, power states, combinations of these, electro-optically, and the like. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

What is claimed is:

1. A hand-held apparatus for sensing an analyte in a breath, the apparatus comprising:
a fluid collecting device configured to collect the breath containing the analyte, wherein the fluid collecting device comprises a mouthpiece;
a fluid input in fluid communication with the fluid collecting device configured to input the breath containing the analyte into the fluid collecting device,
a test strip movably disposed in the fluid collecting device, the test strip comprising an analyte interactant disposed in a plurality of respective regions such that the test strip is usable on more than one occasion, the analyte interactant in fluid communication with the fluid collecting device when the test strip is inserted into the fluid collecting device, wherein the analyte interactant, when contacted by the analyte, reacts to cause a first change in thermal energy within the fluid collecting device;
a modulator that causes a second change in thermal energy;
a thermal sensing device comprising at least one pyroelectric device thermally coupled to the fluid collecting device to generate a first signal in response to at least one of the first change in thermal energy and the second change in thermal energy; and
a control device operatively coupled to the thermal sensing device and the modulator that generates a second signal, wherein the second signal comprises information useful in characterizing the analyte.

2. An apparatus as recited in claim 1, wherein the apparatus comprises a interactant that, when contacted by the analyte, undergoes a second reaction to second analyte cause a third change in thermal energy.

3. The apparatus of claim 1, wherein the plurality of respective regions are equally spaced from one another.

4. The apparatus of claim 1, wherein the plurality of respective regions are disposed discontinuously on the test strip in a pattern.

5. The apparatus of claim 1, wherein the plurality of respective regions upon which the analyte interactant is disposed consist of only the analyte interactant.

6. The apparatus of claim 1, wherein the analyte interactant disposed in each of the plurality of respective regions consists of a first analyte interactant.

7. The apparatus of claim 1, wherein a plurality of analyte interactants are respectively disposed in the plurality of respective regions.

8. The apparatus of claim 7, wherein the plurality of analyte interactants indicate a single analyte.

9. The apparatus of claim 7, wherein the plurality of analyte interactants indicate a plurality of respective analytes.

10. The apparatus of claim 7, wherein the plurality of analyte interactants indicates a single disease.

11. The apparatus of claim 7, wherein the plurality of analyte interactants indicate a plurality of respective diseases.

12. The apparatus of claim 1, wherein the test strip comprises a conductive surface.

13. The apparatus of claim 1, wherein the test strip comprises a pyroelectric ribbon comprising a patterned analyte interactant.

14. The apparatus of claim 1, wherein the test strip comprises a thin film.

15. The apparatus of claim 1, wherein the test strip is disposable.

16. The apparatus of claim 1, wherein the test strip is replenishable after use.

17. The apparatus of claim 1, wherein the analyte interactant is exposed to the analyte by a process of rotation of the test strip.

18. The apparatus of claim 1, wherein the analyte interactant is exposed to the analyte by a process of translation of the test strip.

19. The apparatus of claim 1, wherein the analyte interactant comprises an enzyme.

20. The apparatus of claim 1, wherein the analyte interactant comprises a polymer.

21. The apparatus of claim 1, wherein the apparatus further comprises a packed bed containing the analyte interactant and including microspheres or nanoparticles disposed therein.

22. The apparatus of claim 1, wherein the test strip comprises a disk or cartridge.

23. The apparatus of claim 1, wherein the apparatus is a self-contained apparatus that is portable or handheld.

24. A method for sensing an analyte in a breath, the method comprising:
  a. providing a hand-held thermoelectric sensor comprising:
    i. a thermal sensor comprising a pyroelectric device for measuring thermal energy,
    ii. an analyte interactant; and
    iii. a mouthpiece;
  b. causing the breath and the analyte within the breath to contact the analyte interactant so that the analyte interactant reacts with the analyte to cause a first change in thermal energy, wherein the analyte interactant is disposed on a test strip for insertion into and operation with the thermal sensor, and further wherein the analyte interactant is disposed in a plurality of respective regions such that the test strip is usable on more than one occasion; and
  c. measuring the temperature change using the pyroelectric device and a modulator, wherein the modulator causes a second change in thermal energy.

25. The method of claim 24, wherein the test strip comprises a disk or cartridge.

26. The method of claim 24, wherein the plurality of regions is equally spaced from one another.

27. The method of claim 24, wherein the plurality of regions is disposed discontinuously on the test strip in a pattern.

28. The method of claim 24, wherein the plurality of regions upon which the analyte interactant is disposed consist of only the analyte interactant.

29. The method of claim 24, wherein the analyte interactant disposed in each of the plurality of regions consists of a first analyte interactant.

30. The method of claim 24, wherein a plurality of analyte interactants is respectively disposed in the plurality of regions.

31. The method of claim 30, wherein the plurality of analyte interactants indicates a single analyte.

32. The method of claim 30, wherein the plurality of analyte interactants indicates a plurality of respective analytes.

33. The method of claim 30, wherein the plurality of analyte interactants indicates a single disease.

34. The method of claim 30, wherein the plurality of analyte interactants indicates a plurality of respective diseases.

35. The method of claim 24, wherein the test strip comprises a conductive surface.

36. The method of claim 24, wherein the test strip comprises a pyroelectric ribbon comprising a patterned analyte interactant.

37. The method of claim 24, wherein the test strip comprises a thin film.

38. The method of claim 24, wherein the test strip is disposable.

39. The method of claim 24, wherein the test strip is replenishable after use.

40. The method of claim 24, wherein the analyte interactant is exposed to the analyte by a process of rotation of the test strip.

41. The method of claim 24, wherein the analyte interactant is exposed to the analyte by a process of translation of the test strip.

42. The method of claim 24, wherein the analyte interactant comprises an enzyme.

43. The method of claim 24, wherein the analyte interactant comprises a polymer.

44. The method of claim 24, wherein the test strip comprises a packed bed containing the analyte interactant and including microspheres or nanoparticles disposed therein.

* * * * *